(12) United States Patent
Ihara et al.

(10) Patent No.: US 8,507,514 B2
(45) Date of Patent: Aug. 13, 2013

(54) HYDRAZIDE COMPOUND AND USE OF THE SAME IN PEST CONTROL

(75) Inventors: Hideki Ihara, Osaka (JP); Koji Kumamoto, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 70 days.

(21) Appl. No.: 13/148,130

(22) PCT Filed: Feb. 5, 2010

(86) PCT No.: PCT/JP2010/052109
§ 371 (c)(1),
(2), (4) Date: Aug. 5, 2011

(87) PCT Pub. No.: WO2010/090344
PCT Pub. Date: Aug. 12, 2010

(65) Prior Publication Data
US 2011/0294840 A1    Dec. 1, 2011

(30) Foreign Application Priority Data

Feb. 6, 2009 (JP) ................................ 2009-025839

(51) Int. Cl.
*A01N 43/80* (2006.01)
*C07D 207/18* (2006.01)
*C07D 231/06* (2006.01)
*C07D 261/04* (2006.01)
*C07D 263/08* (2006.01)
*C07D 277/08* (2006.01)
*C07D 413/12* (2006.01)

(52) U.S. Cl.
USPC ..... 514/275; 544/331; 546/272.1; 546/275.4; 548/238; 548/324.1; 548/379.4

(58) Field of Classification Search
None
See application file for complete search history.

(56) References Cited

U.S. PATENT DOCUMENTS

| | | | |
|---|---|---|---|
| 7,947,715 | B2 | 5/2011 | Mita et al. |
| 7,951,828 | B1 | 5/2011 | Mita et al. |
| 2007/0066617 | A1 | 3/2007 | Mita et al. |
| 2010/0144797 | A1 | 6/2010 | Mita et al. |
| 2010/0249191 | A1 | 9/2010 | Coqueron et al. |
| 2011/0166358 | A1 | 7/2011 | Iwata et al. |

FOREIGN PATENT DOCUMENTS

| | | |
|---|---|---|
| JP | 2007-16017 A | 1/2007 |
| JP | 2007-91708 A | 4/2007 |
| JP | 2007-106756 A | 4/2007 |
| JP | 2007-308471 A | 11/2007 |
| JP | 2008-44880 A | 2/2008 |
| JP | 2008-110971 A | 5/2008 |
| JP | 2008-133273 A | 6/2008 |
| JP | 2008-239611 A | 10/2008 |
| WO | WO 2005/051932 A1 | 6/2005 |
| WO | WO 2005/085216 A1 | 9/2005 |
| WO | WO 2007/026965 A1 | 3/2007 |
| WO | WO 2007/070606 A2 | 6/2007 |
| WO | WO 2007/075459 A2 | 7/2007 |
| WO | WO 2007/079162 A1 | 7/2007 |
| WO | WO 2007/105814 A1 | 9/2007 |
| WO | WO 2007/123853 A2 | 11/2007 |
| WO | WO 2007/123855 A2 | 11/2007 |
| WO | WO 2007/125984 A1 | 11/2007 |
| WO | WO 2008/108448 A1 | 9/2008 |
| WO | WO 2008/126665 A2 | 10/2008 |
| WO | WO 2008/128711 A1 | 10/2008 |
| WO | WO 2008/130651 A2 | 10/2008 |
| WO | WO 2008/150393 A1 | 12/2008 |
| WO | WO 2008/154528 A2 | 12/2008 |
| WO | WO 2010/032437 A1 | 3/2010 |

OTHER PUBLICATIONS

International Search Report issued in PCT/JP2010/052109, mailed Jul. 22, 2010.
International Preliminary Report on Patentability (PCT/IB/326 and PCT/IB/373) and Written Opinion of the International Searching Authority (PCT/ISA/237), mailed Aug. 18, 2011, in PCT/JP2010/052109.

*Primary Examiner* — Kamal Saeed
(74) *Attorney, Agent, or Firm* — Birch, Stewart, Kolasch & Birch, LLP

(57) ABSTRACT

There is provided a hydrazide compound having a controlling effect on pests represented by the formula (1): wherein, G is a 5-membered heterocyclic group, M is an oxygen atom or a sulfur atom, $Q^1$, $Q^2$, $Q^3$ and $Q^4$ is independently a nitrogen atom, etc., m is an integer of 0 to 5, $R^2$ is an optionally halogenated C1-C6 alkyl group, etc., $R^5$ and $R^6$ are independently an optionally substituted C1-C12 chain hydrocarbon group, etc., and $R^4$ is an optionally substituted C1-C12 chain hydrocarbon group, etc.

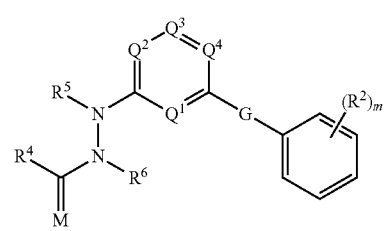

(1)

11 Claims, No Drawings

HYDRAZIDE COMPOUND AND USE OF THE SAME IN PEST CONTROL

TECHNICAL FIELD

The present invention relates to a hydrazide compound and use of the same in pest control.

BACKGROUND ART

Heretofore, compounds having control activity on pests have been found and developed as active ingredients of pest-controlling compositions.

A certain amide compound is known as an active ingredient of a pest-controlling composition (see, JP-A 2008-266293).

SUMMARY OF INVENTION

An object of the present invention is to provide a novel compound having control activity on pests.

The present inventors have intensively studied so as to find a compound having control activity on pests and as a result, found that a hydrazide compound represented by the formula (1) shown below has control activity on pests. Thus, the present invention has been completed.

The present invention provides:

[1] A hydrazide compound represented by the formula (1):

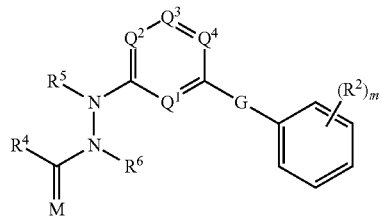

(1)

wherein,

G represents a 5-membered heterocyclic group represented by the following formula G-1, G-2 or G-3:

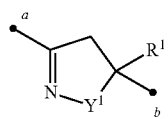

G-1

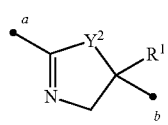

G-2

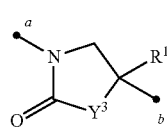

G-3 wherein a •—— and b •—— each represent a bond and the b •—— is linked to the moiety

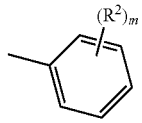

in formula (1), $R^1$ represents a C1-C4 haloakyl group, $Y^1$ represents an oxygen atom, a sulfur atom or an $NR^7$ group, $Y^2$ represents an oxygen atom, a sulfur atom, an $NR^7$ group or a methylene group, $Y^3$ represents an oxygen atom, a sulfur atom, an $NR^7$ group or a methylene group, $R^7$ represents a C1-C6 alkyl group, a C2-C6 alkenyl group, a C2-C6 alkynyl group, a C3-C6 cycloalkyl group, a C4-C7 cycloalkylalkyl group, a C2-C6 alkylcarbonyl group, a C2-C6 alkoxycarbonyl group, a C2-C6 alkylaminocarbonyl group, a C3-C9 dialkylaminocarbonyl group, a phenyl group, a cyano group, a formyl group or a hydrogen atom, M represents an oxygen atom or a sulfur atom, $Q^1$, $Q^2$, $Q^3$ and $Q^4$ independently represent a nitrogen atom or a $CR^3$ group, $R^3$ represents an optionally halogenated C1-C6 alkyl group, an optionally halogenated C1-C6 alkoxy group, a nitro group, a cyano group, a halogen atom or a hydrogen atom, m represents an integer of 0 to 5, $R^2$ represents an optionally halogenated C1-C6 alkyl group, an optionally halogenated C1-C6 alkoxy group, a C1-C6 alkylthio group, a C1-C6 alkylsulfinyl group, a C1-C6 alkylsulfonyl group, a nitro group, a cyano group or a halogen atom, provided that when m is an integer of 2 to 5, $R^2$'s may be the same or different from each other, $R^5$ and $R^6$ independently represent a C1-C12 chain hydrocarbon group optionally substituted with a group selected from Group E1, a benzoyl group optionally substituted with a group selected from Group E2, a C2-C6 alkylcarbonyl group, a C2-C6 alkoxycarbonyl group, a C3-C12 cycloalkyl group, a formyl group or a hydrogen atom, $R^4$ represents a C1-C12 chain hydrocarbon group optionally substituted with a group selected from Group E1, a C3-C12 cyclic hydrocarbon group optionally substituted with a group selected from Group E2, a 5- to 6-membered heterocyclic group optionally substituted with a group selected from Group E2, an $OR^8$ group, an $N(R^9)R^{10}$ group or a hydrogen atom, $R^8$ represents a C1-C12 chain hydrocarbon group optionally substituted with a group selected from Group E1, a C3-C12 cyclic hydrocarbon group optionally substituted with a group selected from Group E2, or a 5- to 6-membered heterocyclic group optionally substituted with a group selected from Group E2, $R^9$ represents a C1-C12 chain hydrocarbon group optionally substituted with a group selected from Group E1, or a C3-C12 cyclic hydrocarbon group optionally substituted with a group selected from Group E2, $R^{10}$ represents a C1-C12 chain hydrocarbon group optionally substituted with a group selected from Group E1, or a hydrogen atom, or $R^9$ and $R^{10}$ are combined at their ends to represent a C2-C9 alkanediyl group, Group E1 consists of a C3-C12 cyclic hydrocarbon group optionally substituted with a group selected from Group E2, a 5- to 6-membered heterocyclic group optionally substituted with a group selected from Group E2, a phenoxy group optionally substituted with a group selected from Group E2, a phenylamino group optionally substituted with a group selected from Group E2, a C2-C6 alkylcarbonyl group, a C2-C6 alkoxycarbonyl group, a C1-C6 alkoxy group, a C1-C6 alkylamino group, a C2-C12 dialkylamino group, a nitro group, a cyano group, a formyl group and a halogen atom, and Group E2 consists of an optionally halogenated C1-C6 alkyl group, an optionally halogenated C1-C6 alkoxy group, a C2-C6 alkylcarbonyl group, a C2-C6 alkoxycarbonyl group, a C1-C6 alkylamino group, a C2-C12 dialkylamino group, a nitro group, a cyano group, a formyl group and a halogen atom (hereinafter referred to as the compound of the present invention);

[2] A pest-controlling comprising the hydrazide compound according to [1] as an active ingredient;

[3] A method for controlling a pest which comprises applying an effective amount of the hydrazide compound according to [1] to the pest or a habitat of the pest; and

[4] A hydrazine compound represented by the formula (2):

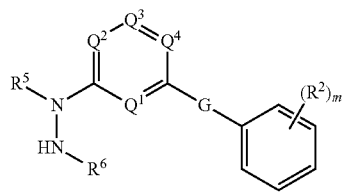

(2)

wherein,

G represents a 5-membered heterocyclic group represented by the following formula G-1, G-2 or G-3:

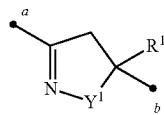

G-1

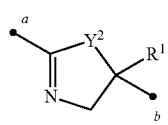

G-2

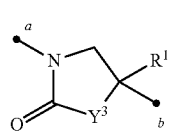

G-3 wherein a •—— and b •—— each represent a bond and the b •—— is linked to the moiety

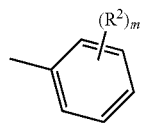

in formula (1), $R^1$ represents a C1-C4 haloakyl group, $Y^1$ represents an oxygen atom, a sulfur atom or an $NR^7$ group, $Y^2$ represents an oxygen atom, a sulfur atom, an $NR^7$ group or a methylene group, $Y^3$ represents an oxygen atom, a sulfur atom, an $NR^7$ group or a methylene group, $R^7$ represents a C1-C6 alkyl group, a C2-C6 alkenyl group, a C2-C6 alkynyl group, a C3-C6 cycloalkyl group, a C4-C7 cycloalkylalkyl group, a C2-C6 alkylcarbonyl group, a C2-C6 alkoxycarbonyl group, a C2-C6 alkylaminocarbonyl group, a C3-C9 dialkylaminocarbonyl group, a phenyl group, a cyano group, a formyl group or a hydrogen atom, $Q^1$, $Q^2$, $Q^3$ and $Q^4$ independently represent a nitrogen atom or a $CR^3$ group, $R^3$ represents an optionally halogenated C1-C6 alkyl group, an optionally halogenated C1-C6 alkoxy group, a nitro group, a cyano group, a halogen atom or a hydrogen atom, m represents an integer of 0 to 5, $R^2$ represents an optionally halogenated C1-C6 alkyl group, an optionally halogenated C1-C6 alkoxy group, a C1-C6 alkylthio group, a C1-C6 alkylsulfinyl group, a C1-C6 alkylsulfonyl group, a nitro group, a cyano group or a halogen atom, provided that when m is an integer of 2 to 5, $R^2$'s may be the same or different from each other, $R^5$ and $R^6$ independently represent a C1-C12 chain hydrocarbon group optionally substituted with a group selected from Group E1, a benzoyl group optionally substituted with a group selected from Group E2, a C2-C6 alkylcarbonyl group, a C2-C6 alkoxycarbonyl group, a C3-C12 cycloalkyl group, a formyl group or a hydrogen atom, Group E1 consists of a C3-C12 cyclic hydrocarbon group optionally substituted with a group selected from Group E2, a 5- to 6-membered heterocyclic group optionally substituted with a group selected from Group E2, a phenoxy group optionally substituted with a group selected from Group E2, a phenylamino group optionally substituted with a group selected from Group E2, a C2-C6 alkylcarbonyl group, a C2-C6 alkoxycarbonyl group, a C1-C6 alkoxy group, a C1-C6 alkylamino group, a C2-C12 dialkylamino group, a nitro group, a cyano group, a formyl group and a halogen atom, and Group E2 consists of an optionally halogenated C1-C6 alkyl group, an optionally halogenated C1-C6 alkoxy group, a C2-C6 alkylcarbonyl group, a C2-C6 alkoxycarbonyl group, a C1-C6 alkylamino group, a C2-C12 dialkylamino group, a nitro group, a cyano group, a formyl group and a halogen atom.

The compound of the present invention has control activity on pests and is therefore useful as an active ingredient of a pest-controlling composition.

MODE FOR CARRYING OUT THE INVENTION

As used herein, the halogen atom means a fluorine atom, a chlorine atom, a bromine atom or an iodine atom.

As used herein, for example, the expression "C2-C6" of a "C2-C6 alkylaminocarbonyl group" means the total number of carbon atoms constituting the alkylaminocarbonyl group is within a range from 2 to 6.

As used herein, examples of each substituent are shown below.

Examples of the 5-membered heterocyclic group represented by the formula G-1, G-2 or G-3 include the following 5-membered heterocyclic groups.

G-1:

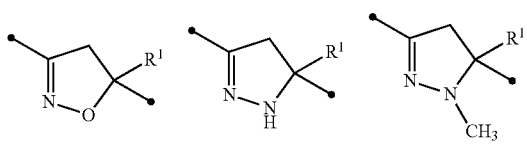

G-2:

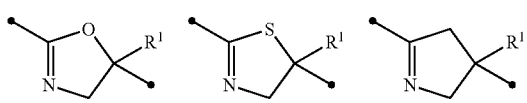

G-3:

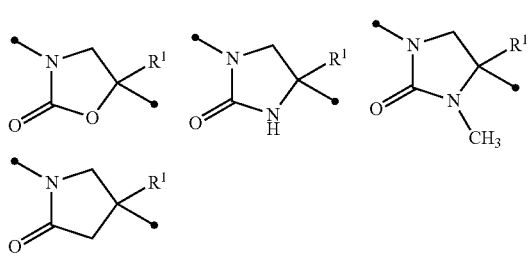

As used herein, examples of the "C1-C4 haloakyl group" include a fluoromethyl group, a difluoromethyl group, a dichloromethyl group, a trifluoromethyl group, a chlorofluoromethyl group, a bromofluoromethyl group, a chlorodifluoromethyl group, a bromodifluoromethyl group, a 1-fluoroethyl group, a 1,1-difluoroethyl group, a 1,1,2,2,2-pentafluoroethyl group, a 1,1,2,2,3,3,3-heptafluoropropyl group, and a 1,2,2,2-tetrafluoro-1-(trifluoromethyl)ethyl group.

Examples of the "C1-C6 alkyl group" include a methyl group, an ethyl group, a propyl group, an isopropyl group, a butyl group, an isobutyl group, a sec-butyl group, a tert-butyl group, a pentyl group, a 1-methylbutyl group, a 2-methylbutyl group, a 3-methylbutyl group, a 1-ethylpropyl group, 1,1-dimethylpropyl group, a 1,2-dimethylpropyl group, a 2,2-dimethylpropyl group, a hexyl group, a 1-methylpentyl group, a 2-methylpentyl group, a 1,1-dimethylbutyl group, and a 1,3-dimethylbutyl group.

Examples of the "C2-C6 alkenyl group" include a vinyl group, a 1-propenyl group, a 2-propenyl group, a 1-methyl-2-propenyl group, a 2-methyl-2-propenyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, and a 5-hexenyl group.

Examples of the "C2-C6 alkynyl group" include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, 4-hexynyl group, and a 5-hexynyl group.

Examples of the "C3-C6 cycloalkyl group" include a cyclopropyl group, a 1-methylcyclopropyl group, a 2-methylcyclopropyl group, a 2,2-dimethylcyclopropyl group, a cyclobutyl group, a cyclopentyl group, a 1-methylcyclopentyl group, a 2-methylcyclopentyl group, a 3-methylcyclopentyl group, and a cyclohexyl group.

Examples of the "C4-C7 cycloalkylalkyl group" include a cyclopropylmethyl group, a 1-cyclopropylethyl group, a 2-cyclopropylethyl group, a cyclobutylmethyl group, a cyclopentylmethyl group, and a cyclohexylmethyl group.

Examples of the "C2-C6 alkylcarbonyl group" include an acetyl group, a propionyl group, a butyroyl group, an isobutyroyl group, and a pivaloyl group.

Examples of the "C2-C6 alkoxycarbonyl group" include a methoxycarbonyl group, an ethoxycarbonyl group, an isopropyloxycarbonyl group, a butoxycarbonyl group, a tert-butoxycarbonyl group, and a pentyloxycarbonyl group.

Examples of the "C2-C6 alkylaminocarbonyl group" include an N-methylaminocarbonyl group, an N-ethylaminocarbonyl group, an N-propylaminocarbonyl group, an N-butylaminocarbonyl group, and an N-pentylaminocarbonyl group.

Examples of the "C3-C9 dialkylaminocarbonyl group" include an N,N-dimethylaminocarbonyl group, and an N,N-diethylaminocarbonyl group.

Examples of the "C1-C6 alkoxy group" include a methoxy group, an ethoxy group, a propoxy group, an isopropoxy group, a butoxy group, an isobutoxy group, a sec-butoxy group, a tert-butoxy group, a pentyloxy group, and a hexyloxy group.

Examples of the "optionally halogenated C1-C6 alkyl group" include C1-C6 alkyl groups, such as a methyl group, an ethyl group, a propyl group, an isopropyl group, a butyl group, an isobutyl group, a sec-butyl group, a tert-butyl group, a pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a hexyl group, a 1-methylpentyl group, a 2-methylpentyl group, a 1,1-dimethylbutyl group, and a 1,3-dimethylbutyl group; and
C1-C6 haloalkyl groups, such as a fluoromethyl group, a difluoromethyl group, a dichloromethyl group, a trifluoromethyl group, a chlorofluoromethyl group, a bromofluoromethyl group, a chlorodifluoromethyl group, a bromodifluoromethyl group, a 1-fluoroethyl group, a 1,1-difluoroethyl group, a 1,1,2,2,2-pentafluoroethyl group, a 1,1,2,2,3,3,3-heptafluoropropyl group, and a 1,2,2,2-tetrafluoro-1-(trifluoromethyl)ethyl group.

Examples of the "optionally halogenated C1-C6 alkoxy group" include C1-C6 alkoxy groups, such as a methoxy group, an ethoxy group, a propoxy group, an isopropoxy group, a butoxy group, an isobutoxy group, a sec-butoxy group, a tert-butoxy group, a pentyloxy group, and a hexyloxy group; and C1-C6 haloalkoxy groups, such as a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group, a 2-bromo-1,1,2-trifluoroethoxy group, a 1,1,2,2,2-pentafluoroethoxy group, a 2,2-dichloro-1,1,2-trifluoroethoxy group, a 2,2,2-trichloro-1,1-difluoroethoxy group, a 2-bromo-1,1,2,2-tetrafluoroethoxy group, a 2,2,3,3-tetrafluoropropyloxy group, a 1,1,2,3,3,3-hexafluoropropyloxy group, a 2,2,2-trifluoro-1-(trifluoromethyl)ethoxy group, a 1,1,2,2,3,3,3-heptafluoropropyloxy group, and a 2-bromo-1,1,2,3,3,3-hexafluoropropyloxy group.

Examples of the "C1-C6 alkylthio group" include a methylthio group, an ethylthio group, a propylthio group, an isopropylthio group, a butylthio group, a pentylthio group, and a hexylthio group.

Examples of the "C1-C6 alkylsulfinyl group" include a methanesulfinyl group, an ethylsulfinyl group, a propylsulfinyl group, an isopropylsulfinyl group, a butylsulfinyl group, a pentylsulfinyl group, and a hexylsulfinyl group.

Examples of the "C1-C6 alkylsulfonyl group" include a methanesulfonyl group, an ethylsulfony group, a propylsulfonyl group, an isopropylsulfonyl group, a butylsulfonyl group, pentylsulfonyl group, and a hexylsulfonyl group.

Examples of the "C3-C12 cycloalkyl group" include a cyclopropyl group, a 1-methylcyclopropyl group, 2-methylcyclopropyl group, a 2,2-dimethylcyclopropyl group, a 2,2,3,3-tetramethylcyclopropyl group, a cyclobutyl group, a cyclopentyl group, a 1-methylcyclopentyl group, a 2-methylcyclopentyl group, a 3-methylcyclopentyl group, a cyclohexyl group, a 1-methylcyclohexyl group, a 2-methylcyclohexyl group, a 3-methylcyclohexyl group, a 4-methylcyclohexyl group, a cycloheptyl group, and a cyclooctyl group.

Examples of the "C2-C9 alkanediyl group" include a 1,2-ethylene group, a 1,4-tetramethylene group, and a 1,5-pentamethylene group.

Examples of the C1-C12 chain hydrocarbon group as used herein include a C1-C12 alkyl group, a C2-C12 alkenyl group, and a C2-C12 alkynyl group.

Examples of the "C1-C12 chain hydrocarbon group optionally substituted with a group selected from Group E1" include C1-C12 alkyl groups, such as a methyl group, an ethyl group, a propyl group, an isopropyl group, a butyl group, an isobutyl group, a sec-butyl group, a tert-butyl group, a pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a hexyl group, a 1-methylpentyl group, a 2-methylpentyl group, a 1,1-dimethylbutyl group, a 1,3-dimethylbutyl group, a heptyl group, an octyl group, a nonyl group, a decyl group, a undecyl group, and a dodecyl group;

C2-C12 alkenyl groups, such as a vinyl group, a 1-methylvinyl group, a 1-phenylvinyl group, a 1-propenyl group, a 2-propenyl group, a 2-butenyl group, a 1-methyl-2-propenyl group, a 2-methyl-2-propenyl group, a 2-pentenyl group, a 2-methyl-2-butenyl group, a 3-methyl-2-butenyl group, a 2-ethyl-2-propenyl group, a 1,1-dimethyl-2-propenyl group, a 2-hexenyl group, a 2-methyl-2-pentenyl group, a 2,4-dimethyl-2,6-heptadienyl group and a 3,7-dimethyl-2,6-octadienyl group;

C2-C12 alkynyl groups, such as a 2-propynyl group, a 2-butynyl group, a 1-methyl-2-propynyl group, a 2-pentynyl group, a 1-methyl-2-butynyl group, a 1,1-dimethyl-2-propynyl group, and a 2-hexynyl group;

C1-C12 haloalkyl groups, such as a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a difluoroiodomethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 1,1,2,2-tetrafluoroethyl group, a 1,1,2,2,2-pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 1-bromo-1,2,2,2-tetrafluoroethyl group, a 2-bromo-1,1,2,2-tetrafluoroethyl group, a 2-fluoropropyl group, a 2-chloropropyl group, a 2,3-dichloropropyl group, a 3,3,3-trifluoropropyl group, a 3-bromo-3,3-difluoropropyl group, a 2,2,3,3-tetrafluoropropyl group, a 2,2,3,3,3-pentafluoropropyl group, a 1,1,2,3,3,3-hexafluoropropyl group, a 1,1,2,2,3,3,3-heptafluoropropyl group, 2,3-dichloro-1,1,2,3,3-pentafluoropropyl group, a 2-fluoro-1-methylethyl group, a 2-chloro-1-methylethyl group, a 2-bromo-1-methylethyl group, 2,2,2-trifluoro-1-(trifluoromethyl)ethyl group, a 1,2,2,2-tetrafluoro-1-(trifluoromethyl)ethyl group, and a 1,1,2,2,3,3,4,4,4-nonafluorbbutyl group;

C2-C12 haloalkenyl groups, such as a 2,2-fluorovinyl group, a 2,2-dichlorovinyl group, a 2-fluoro-2-propenyl group, a 2-chloro-2-propenyl group, a 3-chloro-2-propenyl group, a 2-bromo-2-propenyl group, a 3-bromo-2-propenyl group, a 3,3-difluoro-2-propenyl group, a 2,3-dichloro-2-propenyl group, a 3,3-dichloro-2-propenyl group, a 2,3-dibromo-2-propenyl group, a 2,3,3-trifluoro-2-propenyl group, a 2,3,3-trichloro-2-propenyl group, a 3-chloro-2-butenyl group, a 3-bromo-2-butenyl group, a 4,4-difluoro-3-butenyl group, a 3,4,4-trifluoro-3-butenyl group, a 3-chloro-3,4,4-trifluoro-2-butenyl group, and a 3-bromo-2-methyl-2-propenyl group;

C2-C12 haloalkynyl groups, such as a 3-chloro-2-propynyl group, a 3-bromo-2-propynyl group, and a 3-iodo-2-propynyl group;

cyano(C1-C12 alkyl) groups such as a cyanomethyl group;

C1-C12 nitroalkyl groups such as a nitromethyl group;

(C2-C12 dialkylamino) C1-C12 alkyl groups such as an N,N-dimethylaminomethyl group;

(C1-C6 alkylamino) C1-C12 alkyl groups such as an N-ethylaminomethyl group;

(C1-C6 alkoxy) C1-C12 alkyl groups, such as a methoxymethyl group, a 2-methoxyethyl group, a 2-ethoxyethyl group, a 2-propoxyethyl group, a 2-isopropoxyethyl group, a 2-butoxyethyl group, a 2-isobutoxyethyl group, a 2-(1-methylpropyloxy)ethyl group, and a 2-(1,1-dimethylethoxy)ethyl group;

(C2-C6 alkoxycarbonyl) C1-C12 alkyl groups, such as a methoxycarbonylmethyl group, an ethoxycarbonylmethyl group, a propoxycarbonylmethyl group, an isopropoxycarbonylmethyl group, and a tert-butoxycarbonylmethyl group;

(C2-C6 alkylcarbonyl) C1-C12 alkyl groups, such as an acetylmethyl group and a 2-acetylethyl group;

C1-C12 alkyl groups substituted with a phenoxy group optionally substituted with a group selected from Group E2, such as a phenoxymethyl group, a 4-chlorophenoxymethyl group, and a phenoxyethyl group;

C1-C12 alkyl groups substituted with a phenylamino group optionally substituted with a group selected from Group E2, such as a phenylaminomethyl group, a 4-chlorophenylaminomethyl group, and a phenylaminoethyl group;

C1-C12 alkyl groups substituted with a 5- to 6-membered heterocyclic group optionally substituted with a group selected from Group E2, such as groups represented by the following formulae:

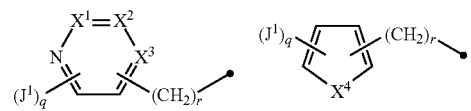

wherein all of $X^1$, $X^2$ and $X^3$ represent a CH group, or any one of $X^1$, $X^2$ and $X^3$ represents a nitrogen atom and the other two represent a CH group; $X^4$ represents an oxygen atom, a sulfur atom or an NH group; r represents an integer of 1 to 12; q represents an integer of 0 to 3; $J^1$ represents an optionally halogenated C1-C6 alkyl group, an optionally halogenated C1-C6 alkoxy group, a C2-C6 alkylcarbonyl group, a C2-C6 alkoxycarbonyl group, a C1-C6 alkylamino group, a C2-C12 dialkylamino group, a nitro group, a cyano group, a formyl group or a halogen atom; and C1-C12 alkyl groups substituted with a C3-C12 cyclic hydrocarbon group optionally substituted with a group selected from Group E2, such as a benzyl group, a phenethyl group, a 4-methylbenzyl group, a 4-chlorobenzyl group, a 2-(cyclopropyl)ethyl group, and a cyclopropylmethyl group.

Examples of the "benzoyl group optionally substituted with a group selected from Group E2" include a benzoyl group, a 2-fluorobenzoyl group, a 3-fluorobenzoyl group, a 4-fluorobenzoyl group, a 2-chlorobenzoyl group, a 3-chlorobenzoyl group, a 4-chlorobenzoyl group, a 2-methoxybenzoyl group, a 3-methoxybenzoyl group, a 4-methoxybenzoyl group, a 2-cyanobenzoyl group, a 3-cyanobenzoyl group, a 4-cyanobenzoyl group, a 2-nitrobenzoyl group, a 3-nitrobenzoyl group and a 4-nitrobenzoyl group.

Examples of the C3-C12 cyclic hydrocarbon group as used herein include a phenyl group, a naphthyl group and a C3-C12 cycloalkyl group.

Examples of the "C3-C12 cyclic hydrocarbon group optionally substituted with a group selected from Group E2" include a phenyl group;
alkylphenyl groups, such as a 2-methylphenyl group, a 3-methylphenyl group, and a 4-methylphenyl group;
(haloakyl)phenyl groups, such as a 2-(trifluoromethyl)phenyl group, a 3-(trifluoromethyl)phenyl group, a 4-(trifluoromethyl)phenyl group, and a 3,5-bis(trifluoromethyl)phenyl group;
halogenated phenyl groups, such as a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,6-dichlorophenyl group, a 3,4-dichlorophenyl group, a 3,5-dichlorophenyl group, a 2,3,4-trichlorophenyl group, a 2,3,5-trichlorophenyl group, a 3,4,5-trichlorophenyl group, a 2,4,6-trichlorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 3,4,5-trifluorophenyl group, a 2,3,5,6-tetrafluorophenyl group, a 2,3,4,5,6-pentafluorophenyl group, a 2,3-dichlorophenyl group, a 2,4-dichlorophenyl group, and a 2,5-dichlorophenyl group;
cyanophenyl groups, such as a 2-cyanophenyl group, a 3-cyanophenyl group, and a 4-cyanophenyl group; nitrophenyl groups such as a 2-nitrophenyl group, a 3-nitrophenyl group, and a 4-nitrophenyl group; alkoxyphenyl groups such as a 2-methoxyphenyl group, a 3-methoxyphenyl group, a 4-methoxyphenyl group, a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, and a 3,5-dimethoxyphenyl group; (haloalkoxy)phenyl groups such as a 2-(trifluoromethoxy)phenyl group, a 3-(trifluoromethoxy)phenyl group, and a 4-(trifluoromethoxy)phenyl group; (alkoxycarbonyl)phenyl groups, such as a 4-methoxycarbonylphenyl group, and a 4-ethoxycarbonylphenyl group; and
C3-C12 cycloalkyl groups, such as a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group, a 1-methylcyclopentyl group, a 2-methylcyclopentyl group, a 3-methylcyclopentyl group, cyclohexyl group, a 1-methylcyclohexyl group, a 2-methylcyclohexyl group, a 3-methylcyclohexyl group, a 4-methylcyclohexyl group, a cycloheptyl group, and a cyclooctyl group.

Examples of the 5- to 6-membered heterocyclic group as used herein include 5-membered heterocyclic groups having an oxygen atom, a sulfur atom and/or a nitrogen atom, such as a tetrahydrofuranyl group, a furanyl group, a thienyl group, a pyrrolyl group, an imidazolyl group, and an isothiazolyl group; and
6-membered heterocyclic groups having an oxygen atom, a sulfur atom and/or a nitrogen atom, such as a piperidino group, a morpholino group, a pyridyl group, a pyridazinyl group, a pyrimidyl group, and a pyrazinyl group.

Examples of the "5- to 6-membered heterocyclic group optionally substituted with a group selected from Group E2" include a 1-pyrrolyl group, a 2-pyrrolyl group, a 3-pyrrolyl group, a 2-furanyl group, a 3-furanyl group, a 2-thienyl group, a 3-thienyl group, a 1-pyrazolyl group, a 3-pyrazolyl group, a 4-pyrazolyl group, a 3-isoxazolyl group, a 4-isoxazolyl group or a 5-isoxazolyl group, a 3-isothiazolyl group, a 4-isothiazolyl group, a 5-isothiazolyl group, a 1-imidazolyl group, a 2-imidazolyl group, a 4-imidazolyl group, a 2-oxazolyl group, a 4-oxazolyl group, 5-oxazolyl group, a 2-thiazolyl group, a 4-thiazolyl group, a 5-thiazolyl group, a 1,2,4-triazol-1-yl group, a 1,2,4-triazol-3-yl group, a 1,3,4-oxadiazol-2-yl group, a 1,3,4-thiadiazol-2-yl group, a 1,2,4-oxadiazol-3-yl group, 1,2,4-oxadiazol-5-yl group, a 1,2,4-thiadiazol-3-yl group, a 1,2,4-thiadiazol-5-yl group, a 1-pyrrolidinyl group, a 2-pyrrolidinyl group, a 3-pyrrolidinyl group, a 2-tetrahydrofuranyl group, a 3-tetrahydrofuranyl group, a 1-piperidino group, a 1-morpholino group, a 2-pyridyl group, a 3-pyridyl group, a 4-pyridyl group, a 3-pyridazinyl group, a 4-pyridazinyl group, a 2-pyrimidinyl group, a 4-pyrimidinyl group, a 5-pyrimidinyl group, a 2-pyrazinyl group, a 1,2,4-triazin-3-yl group, a 1,2,4-triazin-5-yl group, 1,2,4-triazin-6-yl group, and a 1,3,5-triazin-2-yl group.

Examples of the "C1-C6 alkylamino group" include an N-methylamino group, an N-ethylamino group, an N-propylamino group, an N-butylamino group, and an N-pentylamino group.

Examples of the "C2-C12 dialkylamino group" include an N,N-dimethylamino group, and an N,N-diethylamino group.

Examples of the $OR^8$ group include a methoxy group, an ethoxy group, a propoxy group, an isopropoxy group, a butoxy group, an isobutoxy group, a sec-butoxy group, a tert-butoxy group, a vinyloxy group, an allyloxy group, a 2,2,2-trifluoroethoxy group, a cyanomethoxy group, a 2-(N,N-dimethylamino)ethoxy group, a 2-(N-methylamino)ethoxy group, a methoxyethoxy group, a methoxycarbonylmethoxy group, an acetylmethoxy group, a phenoxyethoxy group, a 2-(phenylamino)ethoxy group, a 2-pyridyloxy group, a benzyloxy group, phenoxy group, a cyclohexyloxy group, a furan-2-oxy group, and a pyridin-2-oxy group.

Examples of the $N(R^9)R^{10}$ group include an N-methylamino group, an N,N-dimethylamino group, an N-ethylamino group, an N,N-diethylamino group, an N-methyl-N-ethylamino group, an N-allylamino group, an N-(2,2,2-trifluoroethyl)amino group, an N-(2-(N,N-dimethylamino)ethyl)amino group, an N-(2-(N-methylamino)ethyl)amino group, an N-(2-methoxyethyl)amino group, an N-(methoxycarbonylmethyl)amino group, an N-(2-phenoxyethyl)amino group, an N-(2-(phenylamino)ethyl)amino group, an N-benzylamino group, an N-phenylamino group, an N-phenyl-N-methylamino group, an N-cyclohexylamino group, an N-cyclohexyl-N-methylamino group, a pyrrolidin-1-yl group, and a piperidin-1-yl group.

Examples of the compound of the present invention include the following hydrazide compounds of the formula (1):

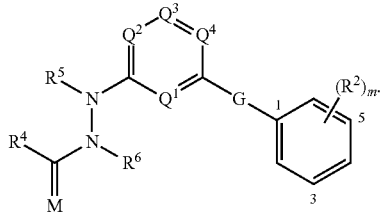

(1)

A hydrazide compound of the formula (1), wherein G is a 5-membered heterocyclic ring represented by formula G-1.

A hydrazide compound of the formula (1), wherein G is a 5-membered heterocyclic ring represented by formula G-2.

A hydrazide compound of the formula (1), wherein G is a 5-membered heterocyclic ring represented by formula G-3.

A hydrazide compound of the formula (1), wherein G is a 5-membered heterocyclic ring represented by formula G-1 and $Y^1$ is an oxygen atom.

A hydrazide compound of the formula (1), wherein $R^1$ is a trifluoromethyl group.

A hydrazide compound of the formula (1), wherein $Q^1$, $Q^2$, $Q^3$ and $Q^4$ are CH groups.

A hydrazide compound of the formula (1), wherein $Q^1$, $Q^3$ and $Q^4$ are CH groups, $Q^2$ is a $CR^3$ group, and $R^3$ is as defined above.

A hydrazide compound of the formula (1), wherein $Q^1$, $Q^3$ and $Q^4$ are CH groups, $Q^2$ is a $CR^3$ group, and $R^3$ is a C1-C6 alkyl group.

A hydrazide compound of the formula (1), wherein $Q^1$, $Q^3$ and $Q^4$ are CH groups, $Q^2$ is a $CR^3$ group, and $R^3$ is a methyl group.

A hydrazide compound of the formula (1), wherein $Q^1$, $Q^3$ and $Q^4$ are CH groups, $Q^2$ is a $CR^3$ group, and $R^3$ is an ethyl group.

A hydrazide compound of the formula (1), wherein $Q^1$, $Q^3$ and $Q^4$ are CH groups, $Q^2$ is a $CR^3$ group, and $R^3$ is a halogen atom.

A hydrazide compound of the formula (1), wherein $Q^1$, $Q^3$ and $Q^4$ are CH groups, $Q^2$ is a $CR^3$ group, and $R^3$ is a fluorine atom.

A hydrazide compound of the formula (1), wherein $Q^1$, $Q^3$ and $Q^4$ are CH groups, $Q^2$ is a $CR^3$ group, and $R^3$ is a chlorine atom.

A hydrazide compound of the formula (1), wherein $Q^1$, $Q^3$ and $Q^4$ are CH groups, $Q^2$ is a $CR^3$ group, and $R^3$ is a bromine atom.

A hydrazide compound of the formula (1), wherein m is 2 and $R^2$'s independently represent a halogen atom.

A hydrazide compound of the formula (1), wherein m is 2 and $R^2$'s represent chlorine atoms.

A hydrazide compound of the formula (1), wherein m is 2, $R^2$'s are substituents at the 3- and 5-positions, and $R^2$'s represent chlorine atoms.

A hydrazide compound of the formula (1), wherein $R^4$ is a C1-C12 chain hydrocarbon group optionally substituted with a group selected from Group E1.

A hydrazide compound of the formula (1), wherein $R^4$ is a C3-C12 cyclic hydrocarbon group optionally substituted with a group selected from Group E2.

A hydrazide compound of the formula (1), wherein $R^4$ is a 5- to 6-membered heterocyclic group optionally substituted with a group selected from Group E2.

A hydrazide compound of the formula (1), wherein $R^4$ is an $OR^8$ group, and $R^8$ is as defined above.

A hydrazide compound of the formula (1), wherein $R^4$ is an $N(R^9)R^{10}$ group, and $R^9$ and $R^{10}$ are as defined above.

A hydrazide compound of the formula (1), wherein $R^5$ is a hydrogen atom.

A hydrazide compound of the formula (1), wherein $R^5$ is a C1-C12 chain hydrocarbon group optionally substituted with a group selected from Group E1.

A hydrazide compound of the formula (1), wherein $R^5$ is a methyl group.

A hydrazide compound of the formula (1), wherein $R^5$ is a C2-C6 alkoxycarbonyl group.

A hydrazide compound of the formula (1), wherein $R^5$ is a C2-C6 alkylcarbonyl group.

A hydrazide compound of the formula (1), wherein $R^5$ is an acetyl group.

A hydrazide compound of the formula (1), wherein $R^5$ is a benzoyl group optionally substituted with a group selected from Group E2.

A hydrazide compound of the formula (1), wherein $R^5$ is a benzoyl group.

A hydrazide compound of the formula (1), wherein $R^6$ is a hydrogen atom.

A hydrazide compound of the formula (1), wherein $R^6$ is a C1-C12 chain hydrocarbon group optionally substituted with a group selected from Group E1.

A hydrazide compound of the formula (1), wherein $R^6$ is a methyl group.

A hydrazide compound of the formula (1), wherein G is a 5-membered heterocyclic ring represented by formula G-1, $Y^1$ is an oxygen atom, and $R^1$ is a trifluoromethyl group.

A hydrazide compound of the formula (1), wherein G is a 5-membered heterocyclic ring represented by formula G-1, $Y^1$ is an oxygen atom, $R^1$ is a trifluoromethyl group, and $Q^1$, $Q^2$, $Q^3$ and $Q^4$ are CH groups.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^2$, $Q^3$ and $Q^4$ are CH groups, m is 2, $R^2$'s are substituents at the 3- and 5-positions, and $R^2$ are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^2$, $Q^3$ and $Q^4$ are CH groups, m is 2, $R^2$'s are substituents at the 3- and 5-positions, $R^2$'s are chlorine atoms, and $R^4$ is a C1-C12 chain hydrocarbon group optionally substituted with a group selected from Group E1.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^2$, $Q^3$ and $Q^4$ are CH groups, m is 2, $R^2$'s are substituents at the 3- and 5-positions, $R^2$'s are chlorine atoms, $R^4$ is a C1-C12 chain hydrocarbon group optionally substituted with a group selected from Group E1, and $R^5$ and $R^6$ are hydrogen atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^2$, $Q^3$ and $Q^4$ are CH groups, m is 2, $R^2$'s are substituents at the 3- and 5-positions, $R^2$'s are chlorine atoms, $R^4$ is a C1-C12 chain hydrocarbon group optionally substituted with a group selected from Group E1, $R^5$ is a hydrogen atom, and $R^6$ is a methyl group.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^2$, $Q^3$ and $Q^4$ are CH groups, m is 2, $R^2$'s are substituents at the 3- and 5-positions, $R^2$ are chlorine atoms, $R^4$ is a C1-C12 chain hydrocarbon group optionally substituted with a group selected from Group E1, $R^5$ is a methyl group, and $R^6$ is a hydrogen atom.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^2$, $Q^3$ and $Q^4$ are CH groups, m is 2, $R^2$'s are substituents at the 3- and 5-positions, $R^2$ are chlorine atoms, $R^4$ is a C1-C12 chain hydrocarbon group optionally substituted with a group selected from Group E1, $R^5$ is a methyl group, and $R^6$ is a methyl group.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, and $R^3$ is as defined above.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is as defined above, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a methyl group, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is an ethyl group, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a halogen atom, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a fluorine atom, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a bromine atom, m is 2, $R^2$'s are substituents at the 3- and 5-positions, and $R^2$'s are chlorine atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is as defined above, m is 2, $R^2$'s are substituents at the 3- and 5-positions, $R^2$ are chlorine atoms, and $R^4$ is a C1-C12 chain hydrocarbon group optionally substituted with a group selected from Group E1.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, and $R^5$ and $R^6$ are hydrogen atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^5$ is a methyl group, and $R^6$ is a hydrogen atom.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^5$ is an acetyl group, and $R^6$ is a hydrogen atom.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^5$ is a benzoyl group, and $R^6$ is a hydrogen atom.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is a C1-C12 chain hydrocarbon group optionally substituted with a group selected from Group E1, and $R^5$ and $R^6$ are hydrogen atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is a C1-C12 cyclic hydrocarbon group optionally substituted with a group selected from Group E1, and $R^5$ and $R^6$ are hydrogen atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is a 5- to 6-membered heterocyclic group optionally substituted with a group selected from Group E2, and $R^5$ and $R^6$ are hydrogen atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is an $OR^8$ group, $R^8$ is as defined above, and $R^5$ and $R^6$ are hydrogen atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is an $N(R^9)R^{10}$ group, $R^9$ and $R^{10}$ are as defined above, and $R^5$ and $R^6$ are hydrogen atoms.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is a C1-C12 chain hydrocarbon group optionally substituted with a group selected from Group E1, $R^5$ is a methyl group, and $R^6$ is a hydrogen atom.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is a C1-C12 chain hydrocarbon group optionally substituted with a group selected from Group E1, $R^5$ is an acetyl group, and $R^6$ is a hydrogen atom.

A hydrazide compound of the formula (1), wherein G is a 5-membered heterocyclic ring represented by formula G-1, $Y^1$ is an oxygen atom, $R^1$ is a trifluoromethyl group, $Q^1$, $Q^3$ and $Q^4$ are CH groups, $Q^2$ is a $CR^3$ group, $R^3$ is a chlorine atom, m is 2, $R^2$'s are substituents at the 3- and 5-positions, $R^2$'s are chlorine atoms, $R^4$ is a C1-C12 chain hydrocarbon group optionally substituted with a group selected from Group E1, $R^5$ is a benzoyl group, and $R^6$ is a hydrogen atom.

A hydrazide compound of the formula (1), wherein G is a 5-membered heterocyclic ring represented by formula G-1, $Y^1$ is an oxygen atom, M represents an oxygen atom, $R^1$ is a trifluoromethyl group, $Q^1$, $Q^2$, $Q^3$ and $Q^4$ are respectively $CR^3$ groups, $R^3$ is C1-C6 alkyl group or halogen atom, m is 2, $R^2$'s are substituents at the 3- and 5-positions, $R^2$'s are chlorine atoms, $R^4$ is a C1-C4 alkyl group, a C1-C4 haloalkyl group, a C3-C6 cycloalkyl group, a phenyl group optionally substituted with a nitro or methoxy group, a pyridyl group, a (C1-C4 alkoxy)methyl group, a (C1-C4 alkyl)amino group, a di(C1-C4 alkyl)amino group, an amino group, a C2-C4 alkenyl group, a phenyl-substituted vinyl group or a hydrogen atom, $R^5$ and $R^6$ are respectively an C1-C4 alkyl, a (C1-C4 alkoxy) carbonyl group, an alkylcarbony group, a phenylcarbonyl group, or a hydrogen atom.

Then, a process for producing the compound of the present invention is explained.

Hereinafter, a compound represented by the formula (α) (α=arbitrary symbol) may be referred to as a "compound (α)".

(Production Process 1)

The compound of the present invention can be produced by reacting the compound (2) with the compound (3):

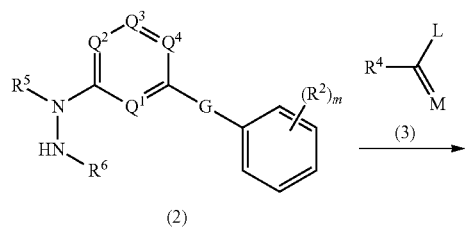

(2) (3)

-continued

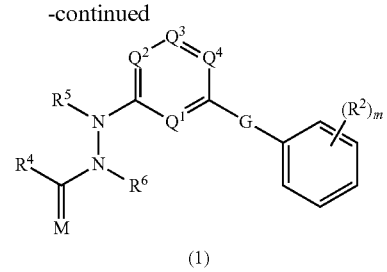

(1)

wherein $Q^1$, $Q^2$, $Q^3$, $Q^4$, $R^2$, $R^4$, $R^5$, $R^6$, G, M, and m are as defined above, and L represents a hydroxyl group or a chlorine atom.

The reaction is usually performed in a solvent.

Examples of the solvent include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

When L is a chlorine atom, the reaction is usually performed in the presence of a base.

Examples of the base include alkali metal hydrides such as sodium hydride; carbonates such as potassium carbonate; alkali metal alkoxides such as potassium tert-butoxide; and organic amines such as triethylamine and pyridine.

When L is a hydroxyl group, the reaction is usually performed in the presence of a condensing agent.

Examples of the condensing agent include dicyclohexylcarbodiimide and 1-(3-dimethylaminopropyl)-3-ethylcarbodiimide hydrochloride.

The amount of the compound (3) to be used in the reaction is usually from 1 to 10 mol per 1 mol of the compound (2).

The amount of the base or the condensing agent to be used is usually from 1 to 10 mol per 1 mol of the compound (2).

The reaction temperature is usually within a range from 0 to 100° C., and the reaction time is usually within a range from 0.5 to 24 hours.

After completion of the reaction, the compound of the present invention can be isolated by post-treatment, for example, by extraction of the reaction mixture with an organic solvent, drying and then concentration. The isolated compound of the present invention can be further purified by chromatography, recrystallization or the like.

(Production Process 2)

The compound of the present invention can also be prepared by reacting the compound (4) with the compound (5):

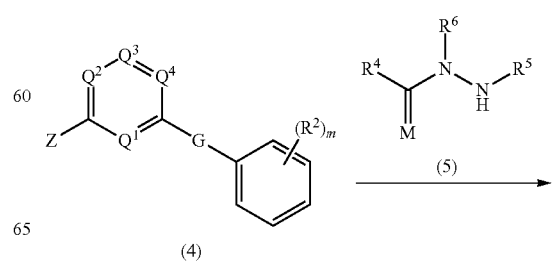

(4) (5)

-continued

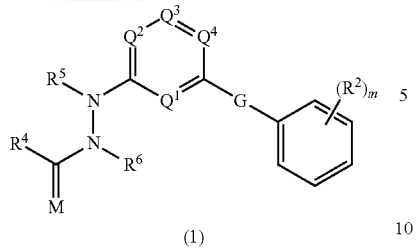

(1)

wherein $Q^1$, $Q^2$, $Q^3$, $Q^4$, $R^2$, $R^4$, $R^5$, $R^6$, G, M and m are as defined above, and Z represents a leaving group such as a fluorine atom, a chlorine atom, a bromine atom, an iodine atom, a methanesulfonyloxy group, a p-toluenesulfonyloxy group or a trifluoromethanesulfonyloxy group.

The reaction is usually performed in a solvent.

Examples of the solvent include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

The reaction may be performed in the presence of a base, if necessary.

Examples of the base include alkali metal hydrides such as sodium hydride; carbonates such as potassium carbonate; alkali metal alkoxides such as potassium tert-butoxide; and organic amines such as triethylamine and pyridine.

The amount of the compound (5) to be used in the reaction is usually from 1 to 5 mol per 1 mol of the compound (4). The amount of the base to be used is usually from 1 to 5 mol per 1 mol of the compound (4).

The reaction temperature is usually within a range from 0 to 100° C., and the reaction time is usually within a range from 0.1 to 24 hours.

After completion of the reaction, the compound of the present invention can be isolated by post-treatment, for example, by extraction of the reaction mixture with an organic solvent, drying and then concentration. The isolated compound of the present invention can be further purified by chromatography, recrystallization or the like.

The reaction can also be performed under conditions for general coupling reaction using a transition metal catalyst as described in literature, for example, Org. Lett., 3, 3803-3805 (2001).

(Production Process 3)

Among compounds of the present invention, the compound (1-1) wherein $R^5$ is a hydrogen atom can be produced by reacting the compound (1-2) with an acid or a base:

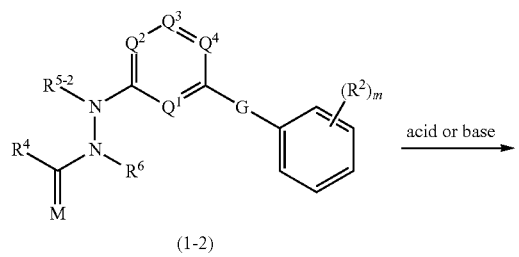

(1-2)

-continued

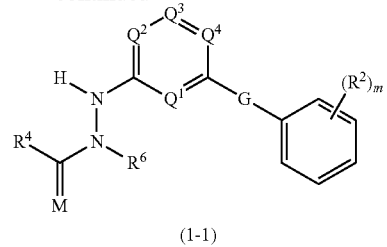

(1-1)

wherein $Q^1$, $Q^2$, $Q^3$, $Q^4$, $R^2$, $R^4$, $R^6$, G, M and m are as defined above, and $R^{5-2}$ represents a benzoyl group optionally substituted with a group selected from Group E2, a C2-C6 alkylcarbonyl group, or a C2-C6 alkoxycarbonyl group.

The reaction may be performed in a solvent, if necessary.

Examples of the solvent include water; ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide and sulfolane; halogenated hydrocarbons such as 1,2-dichloroethane, chloroform and chlorobenzene; alcohols such as methanol, ethanol, and n-propanol; and their mixtures.

Examples of the acid include organic acids such as acetic acid, and trifluoroacetic acid; and inorganic acids such as hydrochloric acid, hydrobromic acid, and sulfuric acid.

Examples of the base include alkali metal hydrides such as sodium hydride; carbonates such as potassium carbonate; alkali metal alkoxides such as potassium tert-butoxide; and organic amines such as triethylamine and pyridine.

The amount of the acid to be used in the reaction is usually from 1 to 100 mol per 1 mol of the compound (1-2).

The amount of the base to be used is usually from 1 to 100 mol per 1 mol of the compound (1-2).

The reaction temperature is usually within a range from 0 to 100° C., and the reaction time is usually within a range from 0.1 to 24 hours.

After completion of the reaction, the compound of the present invention can be isolated by post-treatment, for example, by extraction of the reaction mixture with an organic solvent, drying and then concentration. The isolated compound of the present invention can be further purified by chromatography, recrystallization or the like.

(Production Process 4)

Among compounds of the present invention, the compound (1-3) wherein $R^4$ is an $N(R^9)$ $R^{10}$ group and $R^{10}$ is a hydrogen atom can be produced by reacting the compound (2) with the compound (19):

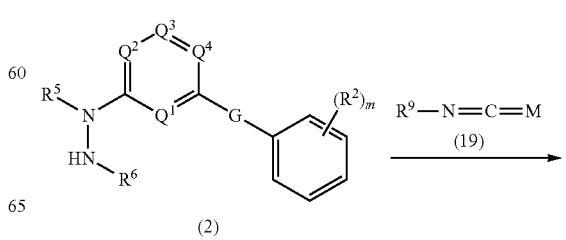

(2) (19)

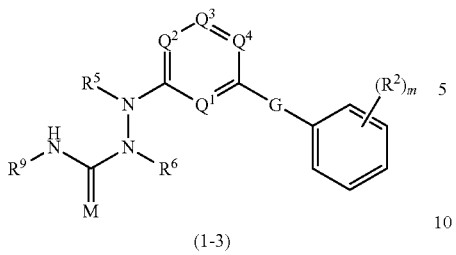

(1-3)

wherein $Q^1$, $Q^2$, $Q^3$, $Q^4$, $R^2$, $R^5$, $R^6$, $R^9$, G, M and m are as defined above.

The reaction is usually performed in a solvent. If necessary, the reaction can be also performed in the presence of a base.

Examples of the solvent include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

Examples of the base include carbonates such as potassium carbonate; and organic amines such as triethylamine, pyridine, 4-(dimethylamino)pyridine, imidazole, and 1,8-diazabicyclo[5,4,0]-7-undecene.

The amount of the compound (19) to be used is usually from 1 to 5 mol per 1 mol of the compound (2).

If the base is used in the reaction, the amount of the base is usually from 1 to 5 mol per 1 mol of the compound (2).

The reaction temperature is usually within a range from 0 to 100° C., and the reaction time is usually within a range from 0.1 to 24 hours.

After completion of the reaction, the compound of the present invention can be isolated by post-treatment, for example, by extraction of the reaction mixture with an organic solvent, drying and then concentration. The isolated compound of the present invention can be further purified by chromatography, recrystallization or the like.

(Production Process 5)

Among compounds of the present invention, the compound (1-4) wherein $R^4$ is $R^{4-1}$ and M is an oxygen atom can be produced by reacting the compound (2) with the compound (21):

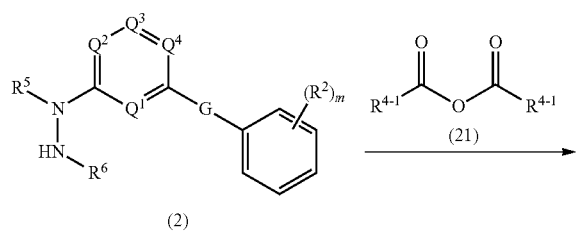

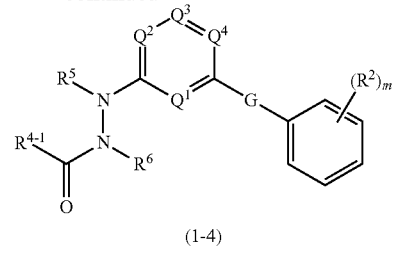

(1-4)

wherein $Q^1$, $Q^2$, $Q^3$, $Q^4$, $R^2$, $R^5$, $R^6$, G, and m are as defined above, and $R^{4-1}$ represents a C1-C12 chain hydrocarbon group optionally substituted with a group selected from Group E1, a C3-C12 cyclic hydrocarbon group optionally substituted with a group selected from Group E2, a 5- to 6-membered heterocyclic group optionally substituted with a group selected from Group E2, or an $OR^8$ group, and $R^8$ is as defined above.

The reaction may be performed in a solvent, if necessary.

Examples of the solvent include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

If necessary, the reaction can be also performed in the presence of a base.

Examples of the base include alkali metal hydrides such as sodium hydride; carbonates such as potassium carbonate; alkali metal alkoxides such as potassium tert-butoxide; and organic amines such as triethylamine, pyridine, 4-(dimethylamino) pyridine, and imidazole.

The amount of the compound (21) to be used is usually from 1 to 10 mol per 1 mol of the compound (2).

If the base is used in the reaction, the amount of the base is usually from 1 to 10 mol per 1 mol of the compound (2).

The reaction temperature is usually within a range from 0 to 100° C., and the reaction time is usually within a range from 0.5 to 24 hours.

After completion of the reaction, the compound of the present invention can be isolated by post-treatment, for example, by extraction of the reaction mixture with an organic solvent, drying and then concentration. The isolated compound of the present invention can be further purified by chromatography, recrystallization or the like.

As described above, the compound represented by formula (2) is useful as an intermediate for the production of the present compound. The compound represented by formula (2) falls within the present invention. Specific and preferred examples of the compound include the compounds of formula (2) in which each substituent is the same as that of the present compounds which are specifically described above.

Next, a process for producing an intermediate used for the preparation of the compound of the present invention is explained.

(Reference Production Process 1)

Among the compounds (2), the compound (2-1) wherein $R^6$ is a hydrogen atom can be produced by performing the first step wherein the compound (6) is reacted with a nitrous acid compound (7) and the second step wherein a compound obtained in the first step is reacted with a reducing agent (8):

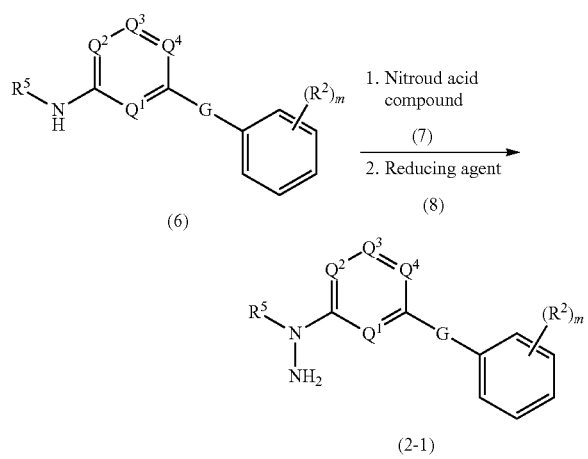

(6) → (2-1)

1. Nitrous acid compound (7)
2. Reducing agent (8)

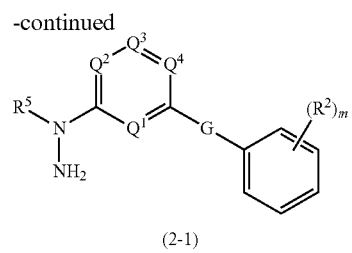

(2-1)

wherein $Q^1$, $Q^2$, $Q^3$, $Q^4$, $R^2$, $R^5$, G and m are as defined above.

The reaction is usually performed in a solvent.

Examples of the solvent include water; ethers such as tetrahydrofuran, diethylether, tert-butyl methyl ether, ethylene glycol dimethyl ether and 1,4-dioxane; acid amides such as N,N-dimethylformamide; aromatic hydrocarbon such as toluene and xylene; sulfoxides such as dimethyl sulfoxide and sulfolane; halogenated hydrocarbons such as 1,2-dichloroethane, chloroform and chlorobenzene; and their mixtures.

Examples of the nitrous acid compound (7) include nitrite salts such as sodium nitrite; and nitrite esters such as ethyl nitrite.

Examples of the reducing agent (8) include sulfite salts such as sodium sulfite; metals such as zinc; and tin (II) chloride.

The amount of the nitrous acid compound (7) to be used is usually from 1 to 10 mol per 1 mol of the compound (6).

The amount of the reducing agent (8) to be used is usually 1 to 10 mol per 1 mol of the compound (6).

The reaction temperature in the first step is usually within a range from −20 to 30° C., and the reaction time in the first step is usually within a range from 0.5 to 24 hours.

The reaction mixture obtained in the first step can be used as it is in the second step wherein it is reacted with the reducing agent (8). The reaction temperature in the second step is usually within a range from −20 to 50° C., and the reaction time in the second step is usually up to 24 hours.

After completion of the reaction, the compound (2-1) can be isolated by post-treatment, for example, by extraction of the reaction mixture with an organic solvent, drying and then concentration. The isolated compound (2-1) can be further purified by chromatography, recrystallization or the like.

(Reference Production Process 2)

Among the compounds (2), the compound (2-1) wherein $R^6$ is a hydrogen atom can be also produced by reacting the compound (6) with an aminating agent (9):

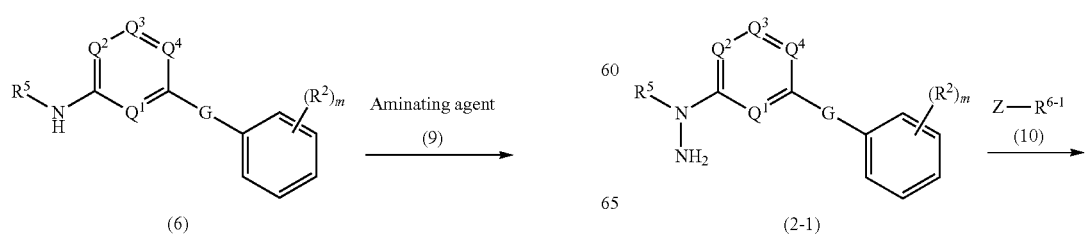

wherein $Q^1$, $Q^2$, $Q^3$, $Q^4$, $R^2$, $R^5$, G and m are as defined above.

The reaction is usually performed in a solvent.

Examples of the solvent include water; ethers such as tetrahydrofuran, diethylether, tert-butyl methyl ether, ethylene glycol dimethyl ether and 1,4-dioxane; acid amides such as N,N-dimethylformamide; aromatic hydrocarbon such as toluene and xylene; sulfoxides such as dimethyl sulfoxide and sulfolane; halogenated hydrocarbons such as 1,2-dichloroethane, chloroform and chlorobenzene; and their mixtures.

The reaction is usually performed in the presence of a base.

Examples of the base include alkali metal hydrides such as sodium hydride; carbonates such as potassium carbonate; alkali metal alkoxides such as potassium tert-butoxide; metal hydroxides such as sodium hydroxide; and organic amines such as triethylamine and pyridine.

Examples of the aminating agent (9) include chloramines such as chloramine; O-acylhydroxylamines such as O-mesitoylhydroxylamine; O-sulfonylhydroxylamine; and hydroxylamine-O-sulfonic acid.

Instead of adding the aminating agent (9), materials for said aminating agent may be added to the reaction system to perform synthesis of the aminating agent (9) and reaction of the compound (6) with the aminating agent (9) simultaneously. For example, sodium hypochlorite and ammonia may be added to the reaction system instead of adding chloramine as the aminating agent (9).

The amount of the aminating agent (9) to be used is usually from 1 to 10 mol, per 1 mol of the compound (6).

The amount of the base to be used is usually 1 to 10 mol per 1 mol of the compound (6).

The reaction temperature is usually within a range from 0 to 100° C., and the reaction time is usually within a range from 0.5 to 24 hours.

After completion of the reaction, the compound (2-1) can be isolated by post-treatment, for example, by extraction of the reaction mixture with an organic solvent, drying and then concentration. The isolated compound (2-1) can be further purified by chromatography, recrystallization or the like.

(Reference Production Process 3)

Among the compounds (2), the compound (2-2) wherein $R^6$ is $R^{6-1}$ can be produced by reacting the compound (2-1) with the compound (10):

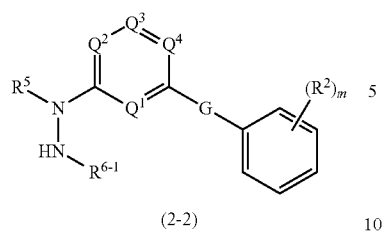

(2-2)

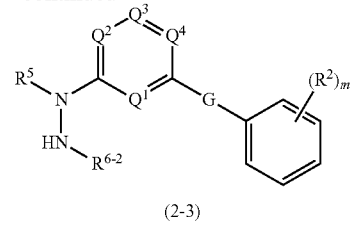

(2-3)

wherein $Q^1$, $Q^2$, $Q^3$, $Q^4$, $R^2$, $R^5$, G, Z and m are as defined above, and $R^{6-1}$ represents a C1-C12 chain hydrocarbon group optionally substituted with a group selected from Group E1, a benzoyl group optionally substituted with a group selected from Group E2, a C2-C6 alkylcarbonyl group, a C2-C6 alkoxycarbonyl group, a C3-C12 cycloalkyl group or a formyl group.

The reaction is usually performed in a solvent.

Examples of the solvent include ethers such as tetrahydrofuran, diethylether, tert-butyl methyl ether, ethylene glycol dimethyl ether and 1,4-dioxane; acid amides such as N,N-dimethylformamide; nitriles such as acetonitrile; aromatic hydrocarbon such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

The reaction is usually performed in the presence of a base.

Examples of the base include alkali metal hydrides such as sodium hydride; carbonates such as potassium carbonate; alkali metal alkoxides such as potassium tert-butoxides; and organic amines such as triethylamine and pyridine.

The amount of the compound (10) to be used is usually from 1 to 10 mol per 1 mol of the compound (2-1).

The amount of the base to be used is usually 1 to 10 mol per 1 mol of the compound (2-1).

The reaction temperature is usually within a range from 0 to 100° C., and the reaction time is usually within a range from 0.5 to 24 hours.

After completion of the reaction, the compound (2-2) can be isolated by post-treatment, for example, by extraction of the reaction mixture with an organic solvent, drying and then concentration. The isolated compound (2-2) can be further purified by chromatography, recrystallization or the like.

(Reference Production Process 4)

Among the compounds (2), the compound (2-3) wherein $R^6$ is $R^{6-2}$ can be produced by reacting the compound (2-1) with the compound (22):

wherein $Q^1$, $Q^2$, $Q^3$, $Q^4$, $R^2$, $R^5$, G, and m are as defined above, and $R^{6-2}$ represents a benzoyl group optionally substituted with a group selected from Group E2, a C2-C6 alkylcarbonyl group, or a C2-C6 alkoxycarbonyl group.

The reaction may be performed in a solvent, if necessary.

Examples of the solvent include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

If necessary, the reaction can be also performed in the presence of a base.

Examples of the base include alkali metal hydrides such as sodium hydride; carbonates such as potassium carbonate; alkali metal alkoxides such as potassium tert-butoxide; and organic amines such as triethylamine, pyridine, 4-(dimethylamino)pyridine, and imidazole.

The amount of the compound (22) to be used is usually from 1 to 10 mol per 1 mol of the compound (2-1).

If the base is used in the reaction, the amount of the base is usually from 1 to 10 mol per 1 mol of the compound (2-1).

The reaction temperature is usually within a range from 0 to 100° C., and the reaction time is usually within a range from 0.5 to 24 hours.

After completion of the reaction, the compound (2-3) can be isolated by post-treatment, for example, by extraction of the reaction mixture with an organic solvent, drying and then concentration. The isolated compound (2-3) can be further purified by chromatography, recrystallization or the like.

(Reference Production Process 5)

Among the compounds (6), the compound (6-1) wherein $R^5$ is a hydrogen atom can be produced by reducing the compound (11) by any one of the following methods (i) to (iii).

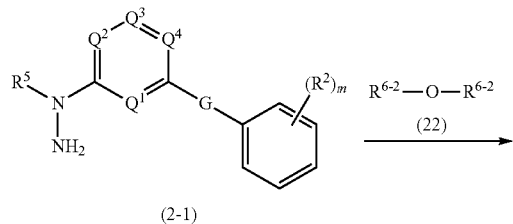

(2-1)

$R^{6-2}$—O—$R^{6-2}$ (22)

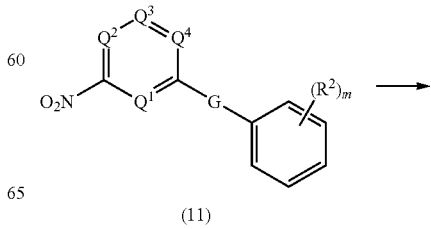

(11)

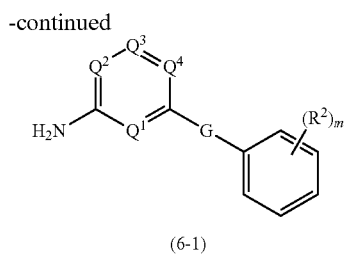

(6-1)

wherein $Q^1$, $Q^2$, $Q^3$, $Q^4$, $R^2$, G and m are as defined above.

(i) Method Comprising a Reaction with a Hydrogen Gas in the Presence of a Transition Metal Catalyst The reaction is performed in a solvent.

Examples of the solvent include esters such as ethyl acetate; alcohols such as ethanol and methanol; water, acetic acid, hydrochloric acid, and their mixtures.

Examples of the transition metal catalyst include Raney nickel, palladium-carbon and platinum dioxide.

The amount of the transition metal catalyst to be used is usually from 0.01 to 0.5 mol per 1 mol of the compound (11).

The amount of the hydrogen gas to be used is usually 1 to 100 mol per 1 mol of the compound (11).

The reaction temperature is usually within a range from 0 to 80° C., and the reaction time is usually within a range from 0.1 to 24 hours.

After completion of the reaction, the compound (6-1) can be isolated by post-treatment, for example, by extraction of the reaction mixture with an organic solvent, drying and then concentration. The isolated compound (6-1) can be further purified by chromatography, recrystallization or the like.

(ii) Method Comprising a Reaction with Hydrazine in the Presence of a Base

The reaction is performed in a solvent.

Examples of the solvent include ethers such as diethylene glycol and triethylene glycol; water; and their mixtures.

Examples of the base include alkali metal hydroxides such as potassium hydroxide.

Examples of the hydrazine include hydrazine hydrates.

The amount of the base to be used is usually 1 to 10 mol per 1 mol of the compound (11).

The amount of the hydrazine to be used is usually from 1 to 10 mol per 1 mol of the compound (11).

The reaction temperature is usually within a range from 0 to 100° C., and the reaction time is usually within a range from 0.5 to 24 hours.

After completion of the reaction, the compound (6-1) can be isolated by post-treatment, for example, by extraction of the reaction mixture with an organic solvent, drying and then concentration. The isolated compound (6-1) can be further purified by chromatography, recrystallization or the like.

(iii) Method Comprising a Reaction with a Metal in the Presence of an Acid

The reaction is usually performed in a solvent.

Examples of the solvent include alcohols such as ethanol; water; and their mixtures.

Examples of the metal include iron, zinc, tin and tin(II) chloride.

Examples of the acid include acetic acid, hydrochloric acid and sulfuric acid.

The amount of the metal to be used in the reaction is usually from 2 to 20 mol per 1 mol of the compound (11).

The amount of the acid to be used is usually 0.1 to 10 mol per 1 mol of the compound (11).

The reaction temperature is usually within a range from 0 to 100° C., and the reaction time is usually within a range from 0.5 to 12 hours.

After completion of the reaction, the compound (6-1) can be isolated by filtration and, if necessary, post-treatment such as organic solvent extraction, drying and concentration. The isolated compound (6-1) can be further purified by chromatography, recrystallization or the like.

(Reference Production Process 6)

Among the compounds (6), the compound (6-2) wherein $R^5$ is $R^{5-1}$ can be produced by reacting the compound (6-1) with the compound (12):

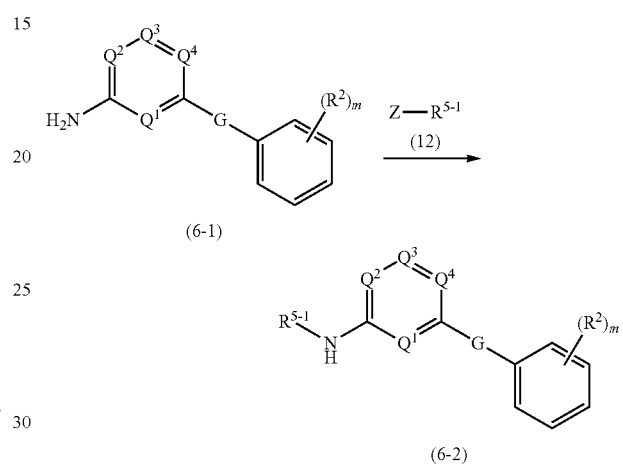

wherein $Q^1$, $Q^2$, $Q^3$, $Q^4$, $R^2$, G, Z and m are as defined above, and $R^{5-1}$ represents a C1-C12 chain hydrocarbon group optionally substituted with a group selected from Group E1, a benzoyl group optionally substituted with a group selected from Group E2, a C2-C6 alkylcarbonyl group, a C2-C6 alkoxycarbonyl group, a C3-C12 cycloalkyl group or a formyl group.

The reaction is usually performed in a solvent.

Examples of the solvent used in the reaction include ethers such as tetrahydrofuran, diethylether, tert-butyl methyl ether, ethylene glycol dimethyl ether and 1,4-dioxane; acid amides such as N,N-dimethylformamide; nitriles such as acetonitrile; aromatic hydrocarbon such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

The reaction is usually performed in the presence of a base.

Examples of the base include alkali metal hydrides such as sodium hydride; carbonates such as potassium carbonate; alkali metal alkoxides such as potassium tert-butoxide; and organic amines such as triethylamine and pyridine.

The amount of the compound (12) to be used is usually from 1 to 10 mol per 1 mol of the compound (6-1).

The amount of the base to be used is usually 1 to 10 mol per 1 mol of the compound (6-1).

The reaction temperature is usually within a range from 0 to 100° C., and the reaction time is usually within a range from 0.5 to 24 hours.

After completion of the reaction, the compound (6-2) can be isolated by post-treatment, for example, by extraction of the reaction mixture with an organic solvent, drying and then concentration. The isolated compound (6-2) can be further purified by chromatography, recrystallization or the like.

(Reference Production Process 7)

Among the compounds (6), the compound (6-3) wherein $R^5$ is $R^{5-2}$ can be produced by reacting the compound (6-1) with the compound (20):

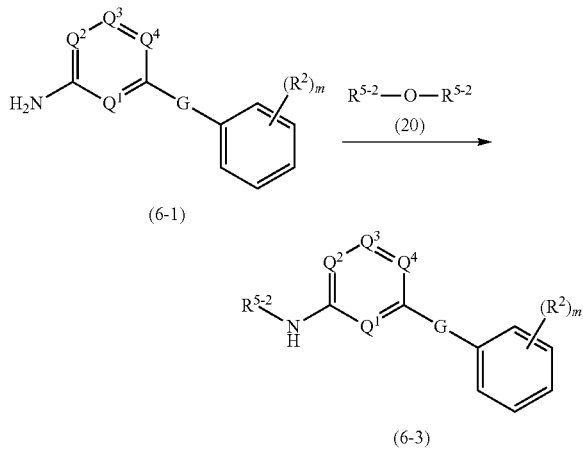

(6-1)

(6-3)

wherein $Q^1$, $Q^2$, $Q^3$, $Q^4$, $R^2$, G and m are as defined above, and $R^{5-2}$ represents a benzoyl group optionally substituted with a group selected from Group E2, a C2-C6 alkylcarbonyl group, or a C2-C6 alkoxycarbonyl group.

The reaction may be performed in a solvent, if necessary.

Examples of the solvent include ethers such as tetrahydrofuran, diethyl ether, tert-butyl methyl ether, ethylene glycol dimethyl ether and 1,4-dioxane; acid amides such as N,N-dimethylformamide; nitriles such as acetonitrile; aromatic hydrocarbons such as toluene and xylene; esters such as ethyl acetate; sulfoxides such as dimethyl sulfoxide and sulfolane; halogenated hydrocarbons such as 1,2-dichloroethane, chloroform and chlorobenzene; and their mixtures.

If necessary, the reaction can be also performed in the presence of a base.

Examples of the base include alkali metal hydrides such as sodium hydride; carbonates such as potassium carbonate; alkali metal alkoxides such as potassium tert-butoxide; and organic amines such as triethylamine, pyridine, 4-(dimethylamino)pyridine, and imidazole.

The amount of the compound (20) to be used is usually from 1 to 10 mol per 1 mol of the compound (6-1).

If the base is used in the reaction, the amount of the base is usually from 1 to 10 mol per 1 mol of the compound (6-1).

The reaction temperature is usually within a range from 0 to 100° C., and the reaction time is usually within a range from 0.5 to 24 hours.

After completion of the reaction, the compound (6-3) can be isolated by post-treatment, for example, by extraction of the reaction mixture with an organic solvent, drying and then concentration. The isolated compound (6-3) can be further purified by chromatography, recrystallization or the like.

(Reference Production Process 8)

Among the compounds (11), the compound (11-1) wherein G is a 5-membered heterocyclic ring represented by formula G-1 and $Y^1$ is an oxygen atom can be produced by performing the first step wherein the compound (13) is reacted with a base and the second step wherein the product obtained in the first step is reacted with the compound (14):

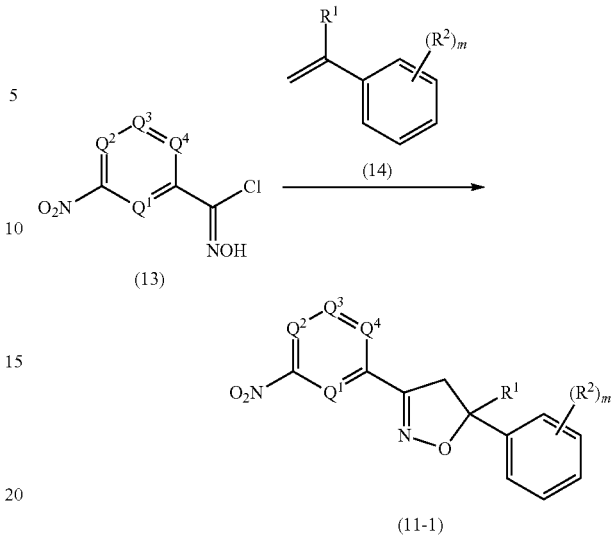

(13)

(11-1)

wherein $Q^1$, $Q^2$, $Q^3$, $Q^4$, $R^1$, $R^2$ and m are as defined above.

The reaction is usually performed in a solvent.

Examples of the solvent include ethers such as tetrahydrofuran, diethylether, tert-butyl methyl ether, ethylene glycol dimethyl ether and 1,4-dioxane; acid amides such as N,N-dimethylformamide; nitriles such as acetonitrile; hydrocarbons such as toluene; esters such as ethyl acetate; sulfoxides such as dimethyl sulfoxide; and their mixtures.

Examples of the base include alkali metal hydrides such as sodium hydride; carbonates such as potassium carbonate; alkali metal alkoxides such as potassium tert-butoxide; and organic amines such as triethylamine and pyridine.

The amount of the base to be used is usually 1 to 10 mol per 1 mol of the compound (13).

The amount of the compound (14) to be used in the reaction is usually from 1 to 10 mol per 1 mol of the compound (13).

The reaction temperature in the first step is usually within a range from 0 to 80° C., and the reaction time in the first step is usually within a range from 0.5 to 24 hours.

The reaction mixture obtained in the first step can be used in the second step without purification. The reaction temperature in the second step is usually within a range from 0 to 80° C., and the reaction time in the second step is usually within a range from 0.5 to 24 hours.

After completion of the reaction, the compound (11-1) can be isolated by post-treatment, for example, by extraction of the reaction mixture with an organic solvent, drying and then concentration. The isolated compound (11-1) can be further purified by chromatography, recrystallization or the like.

(Reference Production Process 9)

The compound (13) can be produced by reacting the compound (15) with a chlorinating agent (16):

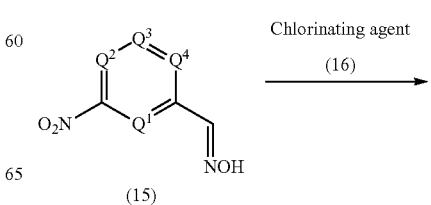

(15)

-continued

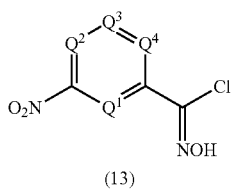

(13)

wherein $Q^1$, $Q^2$, $Q^3$ and $Q^4$ are as defined above.

The reaction is usually performed in a solvent.

Examples of the solvent include ethers such as tetrahydrofuran, diethylether, tert-butyl methyl ether, ethylene glycol dimethyl ether and 1,4-dioxane; hydrocarbons such as toluene; esters such as ethyl acetate; acid amides such as N,N-dimethylformamide; nitriles such as acetonitrile; sulfoxides such as dimethyl sulfoxide; and their mixtures.

Examples of the chlorinating agent (16) include a chlorine gas and N-chlorosuccinimide.

The amount of the chlorinating agent (16) to be used is usually from 1 to 10 mol per 1 mol of the compound (15).

The reaction temperature is usually within a range from −20 to 80° C., and the reaction time is usually within a range from 0.5 to 24 hours.

After completion of the reaction, the compound (13) can be isolated by post-treatment, for example, by extraction of the reaction mixture with an organic solvent, drying and then concentration. The isolated compound (13) can be further purified by chromatography, recrystallization or the like.

(Reference Production Process 10)

The compound (15) can be produced by reacting the compound (17) with hydroxylamine:

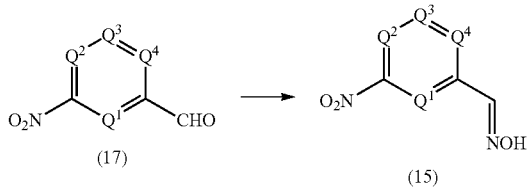

wherein $Q^1$, $Q^2$, $Q^3$ and $Q^4$ are as defined above.

The reaction is usually performed in a solvent.

Examples of the solvent include ethers such as tetrahydrofuran, diethylether, tert-butyl methyl ether, ethylene glycol dimethyl ether and 1,4-dioxane; hydrocarbons such as toluene; esters such as ethyl acetate; acid amides such as N,N-dimethylformamide; alcohols such as ethanol and methanol; nitriles such as acetonitrile; sulfoxides such as dimethyl sulfoxide; water; and their mixtures.

Examples of the hydroxylamine include salts capable of producing hydroxylamine in the reaction system. Examples of the salt include salts of hydroxylamine with mineral acid, such as hydroxylamine hydrochloride and hydroxylamine sulfate.

The amount of the hydroxylamine to be used in the reaction is usually 1 to 10 mol per 1 mol of the compound (17).

When a salt of hydroxylamine with inorganic acid is used, the reaction is performed in the presence of a base.

Examples of the base include organic amines such as triethylamine; carbonates such as sodium carbonate; and alkali metal hydroxides such as sodium hydroxide.

The amount of the base to be used is usually 1 to 10 mol per 1 mol of the salt of hydroxylamine with inorganic acid.

The reaction temperature is usually within a range from 0 to 80° C., and the reaction time is usually within a range from 0.5 to 24 hours.

After completion of the reaction, the compound (15) can be isolated by post-treatment, for example, by extraction of the reaction mixture with an organic solvent, drying and then concentration. The isolated compound (15) can be further purified by chromatography, recrystallization or the like.

(Reference Production Process 11)

Among the compounds (4), the compound (4-1) wherein G is a 5-membered heterocyclic ring represented by G-1 and $Y^1$ is an oxygen atom can be produced by performing a step I wherein the compound (18) is reacted with a base and a step II wherein the compound obtained in the step I is reacted with the compound (14):

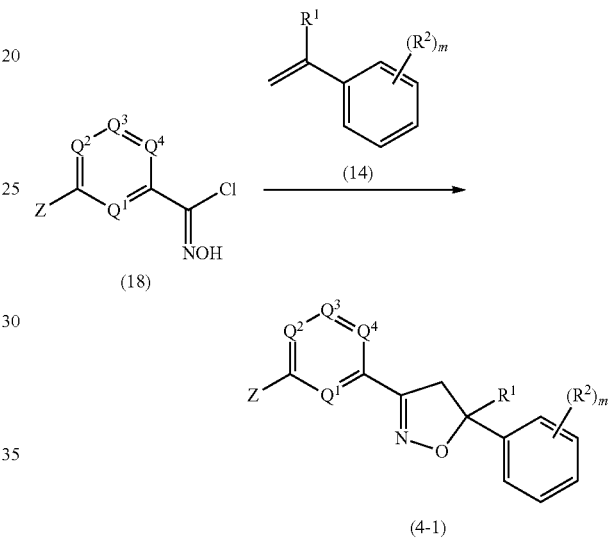

wherein $Q^1$, $Q^2$, $Q^3$, $Q^4$, $R^1$, $R^2$, Z and m are as defined above.

The reaction is usually performed in a solvent.

Examples of the solvent include ethers such as tetrahydrofuran, diethylether, tert-butyl methyl ether, ethylene glycol dimethyl ether and 1,4-dioxane; acid amides such as N,N-dimethylformamide; nitriles such as acetonitrile; hydrocarbons such as toluene; esters such as ethyl acetate; sulfoxides such as dimethyl sulfoxide; and their mixtures.

Examples of the base include alkali metal hydrides such as sodium hydride; carbonates such as potassium carbonate; alkali metal alkoxides such as potassium tert-butoxide; and organic amines such as triethylamine and pyridine.

The amount of the compound (14) to be used in the reaction is usually from 1 to 10 mol per 1 mol of the compound (18).

The amount of the base to be used is usually 1 to 10 mol per 1 mol of the compound (18).

The reaction temperature in the step I is usually within a range from 0 to 80° C., and the reaction time in the step I is usually within a range from 0.5 to 24 hours.

The reaction mixture obtained in the step I can be used in the step II without purification. The reaction temperature in the step II is usually within a range from 0 to 80° C., and the reaction time in the step II is usually within a range from 0.5 to 24 hours.

After completion of the reaction, the compound (4-1) can be isolated by post-treatment, for example, by extraction of the reaction mixture with an organic solvent, drying and then concentration. The isolated compound (4-1) can be further purified by chromatography, recrystallization or the like.
(Reference Production Process 12)

Among the compounds (4), the compound (4-2) wherein G is a 5-membered heterocyclic ring represented by G-1 and $Y^1$ is an $NR^7$ group can be produced, for example, according to a method described in WO 2007/123855.

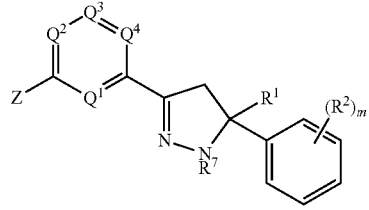

(4-2)

wherein $Q^1$, $Q^2$, $Q^3$, $Q^4$, $R^1$, $R^2$, $R^7$, Z and m are as defined above.
(Reference Production Process 13)

Among the compounds (4), the compound (4-3) wherein G is a 5-membered heterocyclic ring represented by formula G-2 and $Y^2$ is a $Y^{2-1}$ can be produced, for example, according to a method described in JP-A 2007-91708.

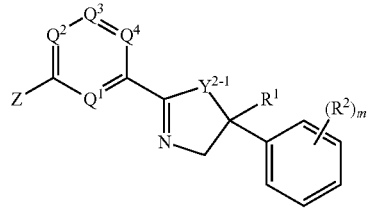

(4-3)

wherein $Q^1$, $Q^2$, $Q^3$, $Q^4$, $R^1$, $R^2$, Z and m represent the same as defined above, and $Y^{2-1}$ represents an oxygen atom, a sulfur atom or a methylene group.
(Reference Production Process 14)

Among the compounds (4), the compound (4-4) wherein G is a 5-membered heterocyclic ring represented by formula G-3 and $Y^3$ is $Y^{3-1}$ can be produced, for example, according to a method described in WO 2007/123853.

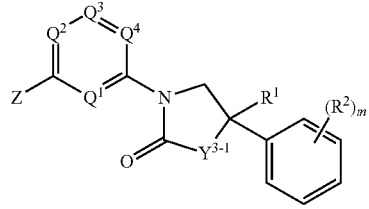

(4-4)

wherein $Q^1$, $Q^2$, $Q^3$, $Q^4$, $R^1$, $R^2$, Z and m are as defined above, $Y^{3-1}$ represents an oxygen atom or $NR^7$, and $R^7$ is as defined above.
(Reference Production Process 15)

Among the compounds (4), the compound (4-5) wherein G is G-3 and $Y^3$ is a methylene group can be produced, for example, according to a method described in JP-A 2008-110971.

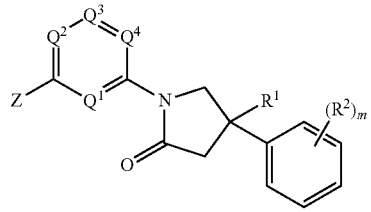

(4-5)

wherein $Q^1$, $Q^2$, $Q^3$, $Q^4$, $R^1$, $R^2$, Z and m are as defined above.

Examples of pests on which the compound of the present invention exhibits efficacy include arthropod pests such as harmful insects and harmful mites, and nemathelminthes such as nematodes, and more specifically are included the following pests.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silver leaf whitefly (*Bemisia argentifolii*), citrus whitefly (*Dialeurodes citri*), and citrus spiny white fly (*Aleurocanthus spiniferus*); scales (Coccidae) such as California red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinus*), and white peach scale (*Pseudaulacaspis pentagona*); lace bugs (Tingidae); psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Ostrinia furnacalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (*Pieridae*) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia*

*pomonella*); leafblotch miners (Gracillariidae) such as tea leafroller (*Caloptilia theivora*), and apple leafminer (*Phyllonorycter ringoneella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*), etc.;

Thysanoptera:
Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:
Housefly (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditteranean fruit fly (*Ceratitis capitata*), legume leafminer (*Liriomyza trifolii*), tomato leafminer (*Liriomyza sativae*), garden pea leafminer (*Chromatomyia horticola*), etc.;

Coleoptera:
Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*), etc.;

Orthoptera:
Asiatic locust (*Locusta migratoria*), African mole cricket (*Gryllotalpa africana*), rice grasshopper (*Oxya yezoensis*), rice grasshopper (*Oxya japonica*), etc.;

Hymenoptera:
Cabbage sawfly (*Athalia rosae*), leaf-cutting ant (*Acromyrmex* spp.), fire ant (*Solenopsis* spp.), etc.;

Nematodes:
Rice white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), Javanese root-knot nematode (*Meloidogyne javanica*), soybean cyst nematode (*Heterodera glycines*), potato cyst nematode (*Globodera rostochiensis*), coffee root-lesion nematode (*Pratylenchus coffeae*), California root-lesion nematode (*Pratylenchus neglectus*), etc.;

Blattodea:
German cockroach (*Blattella germanica*), smokybrown cockroach (*Periplaneta fuliginosa*), American cockroach (*Periplaneta americana*), *Periplaneta brunnea*, oriental cockroach (*Blatta orientalis*), etc.;

Acarina:
Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), and *Eriophyes chibaensis*; tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis, Haemaphysalis flava, Dermacentor taiwanicus, Ixodes ovatus, Ixodes persulcatus, Boophilus microplus*, and *Rhipicephalus sanguineus*; acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletid mites (Cheyletidae) such as *Cheyletus eruditus, Cheyletus malaccensis*, and *Cheyletus moorei*; poultry red mites, etc.

Although the pest-controlling composition of the present invention may be the compound of the present invention itself, the pest-controlling composition of the present invention usually contains the compound of the present invention as an active ingredient and takes the form of a formulation such as an emulsifiable concentrate, an oil solution, a dust, a granule, a wettable powder, a flowable formulation, a microcapsule formulation, an aerosol formulation, a fumigant, a poison bait, or a resin formulation.

The formulation contains usually 0.01 to 95% by weight of the compound of the present invention.

The formulation can be usually produced by mixing the compound of the present invention with an inert carrier, and if necessary, with a surfactant or other auxiliaries for formulation.

Examples of the inert carrier include a solid carrier, a liquid carrier, and a gaseous carrier.

Examples of the solid carrier include finely-divided powder and granules of clay [e.g., kaolin clay, diatomaceous earth, bentonite, agalmatolite clay (Fubasami clay), or acid clay], synthetic hydrated silicon oxide, talc, ceramics, other inorganic minerals (e.g., sericite, quartz, sulfur, activated carbon, calcium carbonate, or hydrated silica), and chemical fertilizers (e.g., ammonium sulfate, ammonium phosphate, ammonium nitrate, ammonium chloride, or urea).

Examples of the liquid carrier include water, alcohols (e.g. methanol, ethanol, isopropyl alcohol, butanol, hexanol, benzyl alcohol, ethylene glycol, propylene glycol, phenoxyethanol, etc.), ketones (e.g. acetone, methyl ethyl ketone, cyclohexanone, etc.), aromatic hydrocarbons (e.g. toluene, xylene, ethylbenzene, dodecylbenzene, phenylxylylethane, methylnaphthalene, etc.), aliphatic hydrocarbons (e.g. hexane, cyclohexane, kerosene, gas oil etc.), esters (e.g. ethyl acetate, butyl acetate, isopropyl myristate, ethyl oleate, diisopropyl adipate, diisobutyl adipate, propylene glycol monomethyl ether acetate, etc.), nitriles (e.g. acetonitrile, isobutyronitrile etc.), ethers (e.g. diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (e.g. N,N-dimethylformamide, N,N-dimethylacetamide, etc.), halogenated hydrocarbons (e.g. dichloromethane, trichloroethane, carbon tetrachloride, etc.), sulfoxides (e.g. dimethyl sulfoxide, etc.), and propylene carbonate, and vegetable oils (e.g. soybean oil, cottonseed oil, etc.).

Examples of the gaseous carrier include fluorocarbon, butane gas, liquefied petroleum gas (LPG), dimethyl ether, and carbon dioxide gas.

Examples of the surfactant include nonionic surfactants such as polyoxyethylene alkyl ethers, polyoxyethylene alkyl aryl ethers, and polyethylene glycol fatty acid esters; and anionic surfactants such as alkyl sulfonate salts, alkylbenzene sulfonate salts, and alkyl sulfate salts.

Examples of other auxiliaries for formulation include a binder, a dispersant, a coloring agent, and a stabilizer, and specific examples thereof include casein, gelatin, saccharides (e.g. starch, gum arabic, cellulose derivatives, alginic acid, etc.), lignin derivatives, bentonite, synthetic water-soluble polymers (e.g. polyvinyl alcohol, polyvinyl pyrrolidone, polyacrylic acids, etc.), PAP (isopropyl acid phosphate), BHT (2,6-di-t-butyl-4-methylphenol), and BHA (a mixture of 2-tert-butyl-4-methoxyphenol and 3-tert-butyl-4-methoxyphenol).

The pest-controlling method of the present invention comprises applying an effective amount of the compound of the present invention to a pest or a habitat of a pest.

In the pest-controlling method of the present invention, a formulation of the compound of the present invention may be used instead of using the compound of the present invention. The formulation can be applied to a pest or a habitat of a pest.

Examples of a habitat of a pest include paddy fields, cultivated lands, orchards, non-crop lands, and houses.

The application of the compound of the present invention or a formulation thereof to a pest or a habitat of a pest can be attained by a conventional method as long as it allows the pest to contact with or ingest the compound of the present invention.

Examples of the application method include spraying treatment, soil treatment, seed treatment, and water culture medium treatment.

The spraying treatment as used herein means a treatment method which comprises treating the plant surface or a pest itself with the active ingredient (i.e. the compound of the present invention) to produce a controlling effect on the pest. Specific examples of the spraying treatment include foliage spraying treatment, and tree trunk spraying treatment.

The soil treatment is a treatment method which comprises treating soil or an irrigation liquid with the active ingredient for the purpose of allowing the active ingredient to permeate and transfer into the interior of the plant body of a crop to be protected from damage such as ingestion by a pest through the root part or the like of the plant, and thereby can protect the crop from damage by a pest. Specific examples of the soil treatment include planting hole treatment (e.g. spraying into planting holes, soil incorporation after planting hole treatment), plant foot treatment (e.g. plant foot spraying, soil incorporation after plant foot treatment, irrigation at plant foot, plant foot treatment at a later seeding raising stage), planting furrow treatment (e.g. planting furrow spraying, soil incorporation after planting furrow treatment), planting row treatment (e.g. planting row spraying, soil incorporation after planting row treatment, planting row spraying at a growing stage), planting row treatment at the time of sowing (e.g. planting row spraying at the time of sowing, soil incorporation after planting row treatment at the time of sowing), broadcast treatment (e.g. overall soil surface spraying, overall soil incorporation), other soil spraying treatment (e.g. spraying of a granular formulation on leaves at a growing stage, spraying under a canopy or around a tree stem, spraying on the soil surface, surface soil incorporation, spraying into seed holes, spraying on the ground surfaces of furrows, spraying between plants), other drenching treatment (e.g. soil drenching, drenching at a seedling raising stage, chemical injection treatment, plant foot drenching, chemical drip irrigation, chemigation), seedling raising box treatment (e.g. spraying into a seedling raising box, irrigation of a seedling raising box), seedling raising tray treatment (e.g. spraying on a seedling raising tray, irrigation of a seedling raising tray), seedbed treatment (e.g. spraying on a seedbed, irrigation of a seedbed, spraying on a lowland rice nursery, immersion of seedlings), seedbed soil incorporation treatment (e.g. seedbed soil incorporation, seedbed soil incorporation before sowing), and other treatment (e.g. culture soil incorporation, plowing, surface soil incorporation, soil incorporation at the place where raindrops fall from a canopy, treatment at a planting position, spraying of a granule formulation on flower clusters, soil incorporation of a paste fertilizer).

The seed treatment is a treatment method which comprises treating directly a seed, a seed tuber or a bulb of a crop to be protected from damage such as ingestion by a pest with or the periphery of the seed, seed tuber or bulb with the active ingredient, and thereby can produce a controlling effect on a pest. Specific examples of the seed treatment include a spraying treatment, a smearing treatment, an immersion treatment, an impregnation treatment, a coating treatment, a film coating treatment, and a pellet coating treatment.

The water culture medium treatment is a treatment method which comprises treating a water culture medium or the like with the active ingredient for the purpose of allowing the active ingredient to permeate and transfer into the interior of the plant body of a crop to be protected from damage such as ingestion by a pest through the root part or the like of the plant, and thereby can protect the crop from damage by a pest. Specific examples of the water culture medium treatment include mixing with a water culture medium, and incorporation into a water culture medium.

When the compound of the present invention is used for pest control in the field of agriculture, the application amount thereof is usually 1 to 10,000 g per 10,000 $m^2$.

When the compound of the present invention is formulated into an emulsifiable concentrate, a wettable powder or a flowable formulation, the formulation is usually applied after it is diluted with water so that the concentration of the compound of the present invention becomes 0.01 to 10,000 ppm. When the compound of the present invention is formulated into a granule or a dust, the formulation is usually applied as it is.

Such a formulation or a water-dilution thereof may be directly sprayed to a pest or a plant such as a crop to be protected from a pest. Alternatively, soil of a cultivated land may be treated with the formulation or a water-dilution thereof in order to control a pest which inhabits the soil.

A resin formulation of the compound of the present invention may be processed into a sheet or a string. Such a resin formulation can be applied by winding a crop with a sheet or a string of the resin formulation, putting a string of the resin formulation around a crop so that the crop is surrounded by the string, or laying a sheet of the resin formulation on the soil surface near the root of a crop.

When the compound of the present invention is used for controlling pests living in a house (e.g. fly, mosquito, cockroach), the application amount thereof is usually 0.01 to 1,000 mg per 1 $m^2$ in the case of plain surface treatment, and is usually 0.01 to 500 mg per 1 $m^3$ in the case of space treatment.

When the compound of the present invention is formulated into an emulsifiable concentrate, a wettable powder or a flowable formulation, the formulation is usually applied after it is diluted with water so that the concentration of the compound of the present invention becomes 0.1 to 1,000 ppm. When the compound of the present invention is formulated into an oil preparation, an aerosol formulation, a fumigant or a poison bait, the formulation is usually applied as it is.

The compound of the present invention can be used as a pesticide for crop lands such as cultivated lands, paddy fields, lawns and orchards, or for non-crop lands. The compound of the present invention can control pests in crop lands where plants including crops and the like listed below are cultivated without causing drug damage to the crops, in some cases.

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The above-described crop plants include crop plants having resistance to herbicides such as HPPD inhibitors (e.g. isoxaflutole), ALS inhibitors (e.g. imazethapyr and thifensulfuron-methyl), EPSP synthesizing enzyme inhibitors, glutamine synthesizing enzyme inhibitors, and bromoxynil, which resistance is imparted by a classical breeding method or a genetic engineering technique.

Examples of the crop plant having herbicide resistance imparted by a classical breeding method include Clearfield (registered mark) canola resistant to an imidazolinone herbicide such as imazethapyr, and STS soybean resistant to a sulfonylurea ALS inhibitor herbicide such as thifensulfuron-methyl.

Examples of the crop plant having herbicide resistance imparted by a genetic engineering technique include corn cultivars having resistance to glyphosate or glufosinate. Some of such corn cultivars are sold under the trade name of RoundupReady (registered mark), LibertyLink (registered mark), and the like.

The above-described crop plants include crop plants having an ability to produce an insecticidal toxin, for example a selective toxin originated from *Bacillus*, which ability is imparted by a genetic engineering technique.

Examples of insecticidal toxins produced in such genetically engineered plants include insecticidal proteins derived from *Bacillus cereus* and *Bacillus popilliae*; insecticidal proteins such as δ-endotoxins derived from *Bacillus thuringiensis* (e.g. Cry1Ab, Cry1Ac, Cry1F, Cry1Fa2, Cry2Ab, Cry3A, Cry3Bb1 and Cry9C), VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The toxins produced in such genetically engineered plants also include hybrid toxins, partly deficient toxins and modified toxins of insecticidal proteins such as δ-endotoxin proteins (e.g., Cry1Ab, Cry1Ac, Cry1F, Cry1Fa2, Cry2Ab, Cry3A, Cry3Bb1 and Cry9C), VIP1, VIP2, VIP3, and VIP3A. The hybrid toxin is made by combining different domains of the insecticidal proteins by a genetic engineering technique. An example of the partly deficient toxin includes Cry1Ab in which a part of amino acids is deleted. An example of the modified toxin includes a toxin in which one or more of amino acids of a naturally occurring toxin are substituted.

Examples of the insecticidal toxin and the genetically engineered crop plant having the ability to produce the insecticidal toxin are described, for example, in EP-A-0 374 753, WO 93/07278, WO 95/34656, EP-A-0 427 529, EP-A-451878, or WO 03/052073.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered mark) (a corn cultivar expressing Cry1Ab toxin), YieldGard Rootworm (registered mark) (a corn cultivar expressing Cry3Bb1 toxin), YieldGard Plus (registered mark), (a corn cultivar expressing Cry1Ab and Cry3Bb1 toxins), Heculex I (registered mark) (a corn cultivar expressing Cry1Fa2 toxin and phosphinothricin N-acetyltransferase (PAT) for imparting resistance to glufosinate), NuCOTN33B (registered mark) (a cotton cultivar expressing Cry1Ac toxin), Bollgard I (registered mark) (a cotton cultivar expressing Cry1Ac toxin), Bollgard II (registered mark) (a cotton cultivar expressing Cry1Ac and Cry2Ab toxins), VIPCOT (registered mark) (a cotton cultivar expressing VIP toxin), NewLeaf (registered mark) (a potato cultivar expressing Cry3A toxin), NatureGard Agrisure GT Advantage (registered mark) (GA21 glyphosate-resistance character), Agrisure CB Advantage (registered mark) (Bt11 corn borer (CB) character), and Protecta (registered mark).

The above-described crop plants include those having an ability to produce an anti-pathogen substance which ability is imparted by a genetic engineering technique.

Examples of the anti-pathogen substance include PR proteins (PRPs, described in EP-A-0 392 225); ion channel inhibitors such as sodium channel inhibitors, and calcium channel inhibitors (e.g. KP1, KP4, or KP6 toxins produced by viruses); stilbene synthase; bibenzyl synthase; chitinase; glucanase; and substances produced by microorganisms such as peptide antibiotics, heterocycle-containing antibiotics, and protein factors involved in plant disease-resistance (described in WO 03/000906). Such anti-pathogen substances and genetically engineered plants which produce the anti-pathogen substances are described in EP-A-0 392 225, WO 05/33818, or EP-A-0 353 191.

The pest-controlling composition of the present invention may contain other insecticides, acaricides, nematocides, fungicides, herbicides, plant growth regulators, synergists, fertilizers, soil conditioners, or animal feed.

The compound of the present invention may be mixed with other insecticides, acaricides, nematocides, fungicides, phytohormone agents, plant growth regulators, herbicides, synergists, drug damage-alleviating agents, pigments, fertilizers, or the like to prepare a mixed formulation, which may be used in spraying treatment, soil treatment or water culture medium treatment.

Examples of the active ingredient of the insecticide include:

(1) Organic Phosphorous Compounds:

acephate, aluminium phosphide, butathiofos, cadusafos, chlorethoxyfos, chlorfenvinphos, chlorpyrifos, chlorpyrifos-methyl, cyanophos:CYAP, diazinon, DCIP (dichlorodiisopropyl ether), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, hydrogen phosphide, isofenphos, isoxathion, malathion, mesulfenfos, methidathion:DMTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, etc.;

(2) Carbamate Compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, etc.;

(3) Synthetic Pyrethroid Compounds:

acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, 2,3,5,6-tetrafluoro-4-(methoxymethyl)benzyl (EZ)-(1RS,3RS;1RS,3SR)-2,2-dimethyl-3-prop-1-enylcyclopropane carboxylate, 2,3,5,6-tetrafluoro-4-methylbenzyl (EZ)-(1RS,3RS;1RS,3SR)-2,2-dimethyl-3-prop-1-enylcyclopropane carboxylate, and 2,3,5,6-tetrafluoro-4-(methoxymethyl)benzyl (1RS,3RS;1RS,3SR)-2,2-dimethyl-3-(2-methyl-1-propenyl)cyclo propane carboxylate, etc.;

(4) Nereistoxin Compounds:

cartap, bensultap, thiocyclam, monosultap, bisultap, etc.;

(5) Neonicotinoid Compounds:

imidacloprid, nitenpyram, acetamiprid, thiamethoxam, thiacloprid, dinotefuran, clothianidin, etc.;

(6) Benzoylurea Compounds:

chlorfluazuron, bistrifluoron, diafenthiuron, diflubenzuron, fluazuron, flucycloxuron), flufenoxuron, hexaflumuron, lufenuron, novaluron, noviflumuron, teflubenzuron, triflumuron, etc.;

(7) Phenylpyrazole Compounds:

acetoprole, ethiprole, fipronil, vaniliprole, pyriprole, pyraflu-prole, etc.;

(8) Bt Toxin Insecticides:

live spores or crystal toxins originated from *Bacillus thuringiesis* and a mixture thereof;

(9) Hydrazine Compounds:

chromafenozide, halofenozide, methoxyfenozide, tebufenozide, etc.;

(10) Organic Chlorine Compounds:

aldrin, dieldrin, dienochlor, endosulfan, methoxychlor, etc,;

(11) Natural Insecticides:

machine oil, nicotine-sulfate, etc.; and

(12) Other Insecticides:

avermectin-B, bromopropylate, buprofezin, chlorphenapyr, cyromazine, D-D(1,3-Dichloropropene), emamectin-benzoate, fenazaquin, flupyrazofos, hydroprene, indoxacarb, metoxadiazone, milbemycin-A, pymetrozine, pyridalyl, pyriproxyfen, spinosad, sulfluramid, tolfenpyrad, triazamate, flubendiamide, SI-0009, cyflumetofen, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, nidinotefuran, potassium oleate, protrifenbute, spiromesifen, sulfur, metaflumizone, spirotetramat, etc.

Examples of the active ingredient of the acaricide include acequinocyl, amitraz, benzoximate, bromopropylate, chinomethionat, chlorobenzilate, CPCBS (chlorfenson), clofentezine, Kelthane (dicofol), etoxazole, fenbutatin oxide, fenothiocarb, fenpyroximate, fluacrypyrim, fluproxyfen, hexythiazox, propargite:BPPS, polynactins, pyridaben, pyrimidifen, tebufenpyrad, tetradifon, spirodiclofen, amidoflumet, bifenazate, and cyflumetofen.

Examples of the active ingredient of the nematocide include DCIP, fosthiazate, levamisol, methylsothiocyanate, and morantel tartarate.

EXAMPLES

Hereinafter, the present invention is described in more detail by way of Production Examples, Formulation Examples and Test Examples. However, the present invention is not limited to these Examples.

First, Production Examples of the compound of the present invention are shown.

Production Example 1

To a solution of 1.39 g of a compound obtained in Reference Production Example 6 as described later and 330 mg of triethylamine in 12 ml of tetrahydrofuran was added dropwise 257 mg of acetyl chloride at 0° C., followed by stirring at 0° C. for 1 hour and then standing at room temperature for 13 hours. To the reaction mixture was added water, followed by extraction with ethyl acetate. The organic layer was dried over anhydrous sodium sulfate and then concentrated under reduced pressure. The residue was subjected to silica gel column chromatography to obtain 1.30 g of a compound represented by the following formula (hereinafter referred to as the present compound (1)).

Present Compound (1)

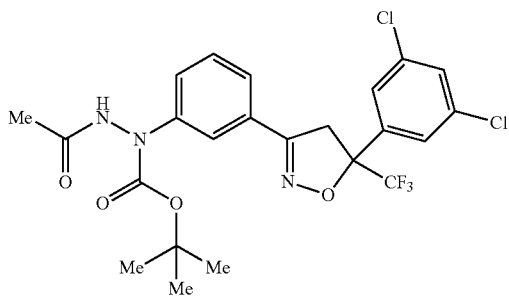 [SMILES: CC(=O)NN(C(=O)OC(C)(C)C)c1cccc(C2=NOC(c3cc(Cl)cc(Cl)c3)(C(F)(F)F)C2)c1]

Melting point: 111° C.

Production Example 2

To a solution of 250 mg of the present compound (1) in 1 ml of tetrahydrofuran was added dropwise 1.5 mL of trifluoroacetic acid at room temperature, followed by stirring for 1 hour. To the reaction mixture was added an aqueous saturated sodium hydrogen carbonate solution, followed by extraction with ethyl acetate. The organic layer was dried over anhydrous sodium sulfate and then concentrated under reduced pressure. The residue was subjected to silica gel column chromatography to obtain 179 mg of a compound represented by the following formula (hereinafter referred to as the present compound (2))

Present Compound (2)

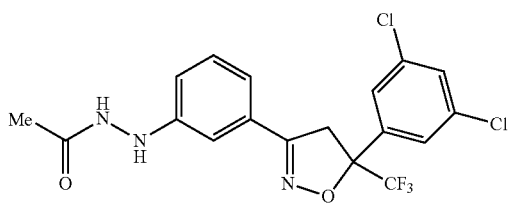 [SMILES: CC(=O)NNc1cccc(C2=NOC(c3cc(Cl)cc(Cl)c3)(C(F)(F)F)C2)c1]

Melting point: 100° C.

Production Example 3

To a suspension of 78 mg of sodium hydride (60% in oil) in 4 mL of tetrahydrofuran was added dropwise a solution of 800 mg of the present compound (1) in 6 ml of tetrahydrofuran at room temperature. After stirring at the same temperature for 30 minutes, 355 mg of methyl iodide was added thereto at room temperature, followed by stirring at the same temperature for 10 hours. To the mixture was added an aqueous saturated sodium hydrogen carbonate solution, followed by extraction with ethyl acetate. The organic layer was dried over anhydrous sodium sulfate and then concentrated under reduced pressure. The residue was subjected to silica gel column chromatography to obtain 697 mg of a compound represented by the following formula (hereinafter referred to as the present compound (3)).

Present Compound (3)

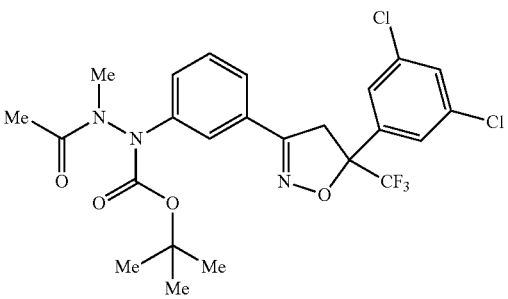 [SMILES: CC(=O)N(C)N(C(=O)OC(C)(C)C)c1cccc(C2=NOC(c3cc(Cl)cc(Cl)c3)(C(F)(F)F)C2)c1]

Melting point: 79° C.

Production Example 4

To 324 mg of the present compound (3) was added 5 mL of trifluoroacetic acid at room temperature, followed by stirring at the same temperature for 30 minutes. The reaction mixture was concentrated under reduced pressure and ethyl acetate was added to the residue. The organic layer was washed with an aqueous saturated sodium hydrogen carbonate solution, dried over anhydrous sodium sulfate and then concentrated under reduced pressure. The residue was subjected to silica gel column chromatography to obtain 290 mg of a compound represented by the following formula (hereinafter referred to as the present compound (4)).

Present Compound (4)

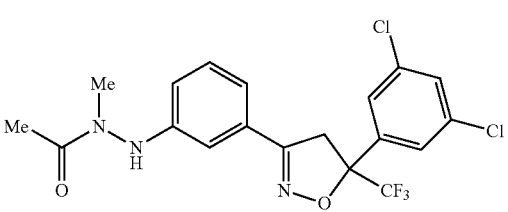 [SMILES: CC(=O)N(C)Nc1cccc(C2=NOC(c3cc(Cl)cc(Cl)c3)(C(F)(F)F)C2)c1]

Melting point: 88° C.

Production Example 5

To a solution of 1.00 g of a crude compound obtained in Reference Production Example 10 as described later and 180 mg of triethylamine in 3 ml of tetrahydrofuran was added dropwise 139 mg of acetyl chloride at 0° C., followed by stirring at the same temperature for 1 hour. To the reaction mixture was added an aqueous saturated sodium hydrogen carbonate solution, followed by extraction with ethyl acetate. The organic layer was dried over anhydrous sodium sulfate and then concentrated under reduced pressure. The residue was subjected to silica gel column chromatography to obtain 498 mg of a compound represented by the following formula (hereinafter referred to as the present compound (5)).

Present Compound (5)

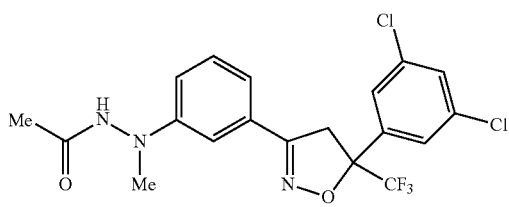 [SMILES: CC(=O)NN(C)c1cccc(C2=NOC(c3cc(Cl)cc(Cl)c3)(C(F)(F)F)C2)c1]

Melting point: 87° C.

Production Example 6

To a solution of 248 mg of the present compound (5) in 2 mL of N,N-dimethylformamide were added 92 mg of sodium carbonate and 87 mg of methyl iodide at room temperature. After stirring at the same temperature for 5 hours stirring, 20 mL of tert-butyl methyl ether was added thereto and a precipitate was filtered. The filtrate was concentrated under reduced pressure, and the residue was subjected to silica gel column chromatography to obtain 140 mg of a compound represented by the following formula (hereinafter referred to as the present compound (6)).

Present Compound (6)

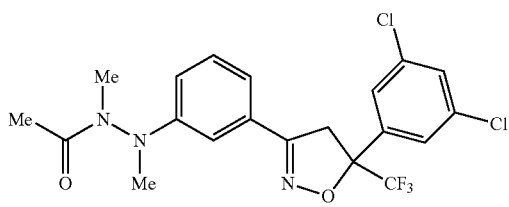 [SMILES: CC(=O)N(C)N(C)c1cccc(C2=NOC(c3cc(Cl)cc(Cl)c3)(C(F)(F)F)C2)c1]

Melting point: 151° C.

Production Example 7

To a solution of 1.04 g of a crude compound obtained in Reference Production Example 3 as described later and 269 mg of triethylamine in 5 ml of tetrahydrofuran was added dropwise 391 mg of 3,3,3-trifluoropropionyl chloride at 0° C., followed by stirring at room temperature for 4 hours. To the reaction mixture was added an aqueous saturated sodium hydrogen carbonate solution, followed by extraction with ethyl acetate. The organic layer was dried over anhydrous sodium sulfate and then concentrated under reduced pressure. The residue was subjected to silica gel column chromatography to obtain 639 mg of a compound represented by the following formula (hereinafter referred to as the present compound (7)).

Present Compound (7)

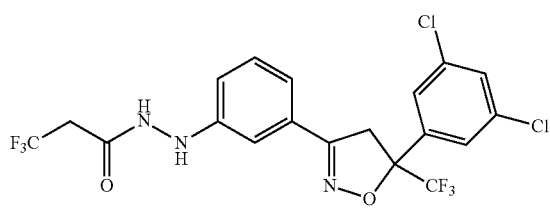 [SMILES: O=C(CC(F)(F)F)NNc1cccc(C2=NOC(c3cc(Cl)cc(Cl)c3)(C(F)(F)F)C2)c1]

Melting point: 75° C.

Production Example 8

To a solution of 220 mg of a crude compound obtained in Reference Production Example 14 as described later and 43 mg of pyridine in 2 ml of ethyl acetate was added dropwise 80 mg of 3,3,3-trifluoropropionyl chloride at 0° C., followed by stirring at room temperature for 4 hours. To the reaction mixture was added water, followed by extraction with ethyl acetate. The organic layer was dried over anhydrous sodium sulfate and then concentrated under reduced pressure. The residue was subjected to silica gel column chromatography to obtain 162 mg of a compound represented by the following formula (hereinafter referred to as the present compound (8)).

Present Compound (8)

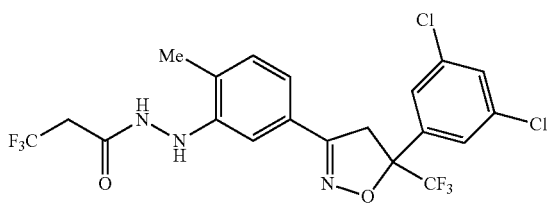 [SMILES: Cc1ccc(C2=NOC(c3cc(Cl)cc(Cl)c3)(C(F)(F)F)C2)cc1NNC(=O)CC(F)(F)F]

$^1$H-NMR (CDCl$_3$) δ: 8.01-7.96 (1H, br m), 7.48-7.42 (3H, m), 7.15-7.04 (3H, m), 6.11-6.00 (1H, m), 4.04-4.00 (1H, m), 3.63 (1H, d, J=17.1 Hz), 3.25-3.19 (2H, m), 2.26 (3H, s).

Production Example 9

To a solution of 220 mg of a crude compound obtained in Reference Production Example 14 as described later and 43 mg of pyridine in 2 ml of ethyl acetate was added dropwise 80 mg of isopropyl chloroformate at 0° C., followed by stirring at room temperature for 4 hours. To the reaction mixture was added water, followed by extraction with ethyl acetate. The organic layer was dried over anhydrous sodium sulfate and then concentrated under reduced pressure. The residue was subjected to silica gel column chromatography to obtain 127 mg of a compound represented by the following formula (hereinafter referred to as the present compound (9)).

Present Compound (9)

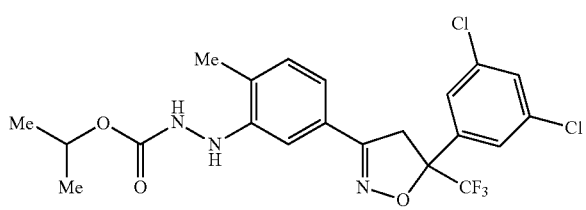 [SMILES: Cc1ccc(C2=NOC(c3cc(Cl)cc(Cl)c3)(C(F)(F)F)C2)cc1NNC(=O)OC(C)C]

Melting point: 71° C.

Production Example 10

To a solution of 412 mg of a crude compound obtained in Reference Production Example 18 as described later and 102 mg of triethylamine in 6 ml of tetrahydrofuran was added dropwise 148 mg of 3,3,3-trifluoropropionyl chloride at 0° C., followed by stirring at room temperature for 4 hours. To the reaction mixture was added an aqueous saturated sodium hydrogen carbonate solution, followed by extraction with ethyl acetate. The organic layer was dried over anhydrous sodium sulfate and then concentrated under reduced pressure. The residue was subjected to silica gel column chromatography to obtain 167 mg of a compound represented by the following formula (hereinafter referred to as the present compound (10)).

Present Compound (10)

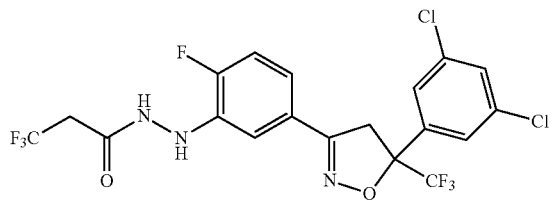 [SMILES: O=C(CC(F)(F)F)NNc1cc(C2=NOC(c3cc(Cl)cc(Cl)c3)(C(F)(F)F)C2)ccc1F]

$^1$H-NMR (CDCl$_3$) δ: 7.89-7.55 (1H, m), 7.46-7.42 (3H, m), 7.28 (1H, dd, J=7.9, 1.8 Hz), 7.18-7.00 (2H, m), 6.39-6.29 (1H, m), 4.03-3.98 (1H, m), 3.65-3.60 (1H, m), 3.21 (2H, q, J=10.3 Hz).

Production Example 11

To a solution of 510 mg of a crude compound obtained in Reference Production Example 21 as described later and 123 mg of triethylamine in 6 ml of tetrahydrofuran was added dropwise 179 mg of 3,3,3-trifluoropropionyl chloride at 0° C., followed by stirring at room temperature for 2.5 hours. To the reaction mixture was added an aqueous saturated sodium hydrogen carbonate solution, followed by extraction with ethyl acetate. The organic layer was dried over anhydrous sodium sulfate and then concentrated under reduced pressure. The residue was subjected to silica gel column chromatography to obtain 175 mg of a compound represented by the following formula (hereinafter referred to as the present compound (11)).

Present Compound (11)

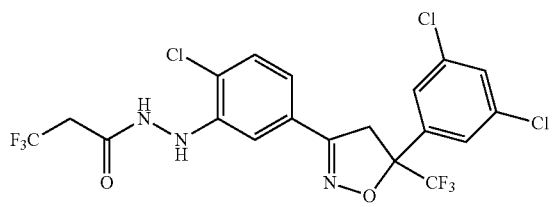

Melting point: 89° C.

Production Example 12

To a solution of 110 mg of a compound obtained in Reference Production Example 23 as described later and 22 mg of triethylamine in 2 ml of tetrahydrofuran was added dropwise 23 mg of cyclopropanecarbonyl chloride at 0° C., followed by stirring at room temperature for 1 hour. To the reaction mixture was added water, followed by extraction with ethyl acetate. The organic layer was dried over anhydrous sodium sulfate and then concentrated under reduced pressure. The residue was subjected to silica gel column chromatography to obtain 101 mg of a compound represented by the following formula (hereinafter referred to as the present compound (12)).

Present Compound (12)

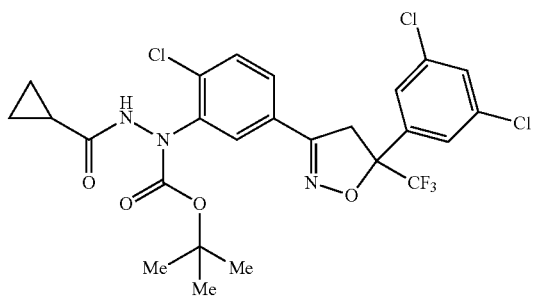 [SMILES: CC(C)(C)OC(=O)N(NC(=O)C1CC1)c1cc(C2=NOC(c3cc(Cl)cc(Cl)c3)(C(F)(F)F)C2)ccc1Cl]

Melting point: 180° C.

Production Example 13

To 272 mg of the present compound (12) was added 2 mL of trifluoroacetic acid at room temperature, followed by stirring at the same temperature for 1 hour. The reaction mixture was concentrated under reduced pressure and ethyl acetate was added to the residue. The organic layer was washed with an aqueous saturated sodium hydrogen carbonate solution, dried over anhydrous sodium sulfate and then concentrated under reduced pressure. The residue was subjected to silica gel column chromatography to obtain 214 mg of a compound represented by the following formula (hereinafter referred to as the present compound (13)).

Present Compound (13)

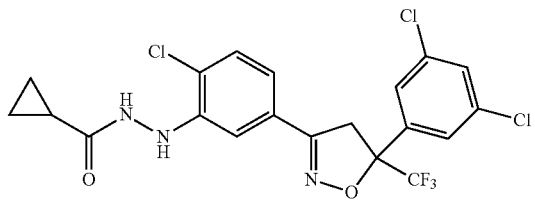 [SMILES: O=C(NNc1cc(C2=NOC(c3cc(Cl)cc(Cl)c3)(C(F)(F)F)C2)ccc1Cl)C1CC1]

Melting point: 100° C.

Production Example 14

To a solution of 262 mg of a compound obtained in Reference Production Example 23 as described later and 61 mg of triethylamine in 2 ml of tetrahydrofuran was added dropwise 72 mg of isovaleryl chloride at 0° C., followed by stirring at room temperature for 9 hours. To the reaction mixture was added water, followed by extraction with ethyl acetate. The organic layer was dried over anhydrous sodium sulfate and then concentrated under reduced pressure. The residue was subjected to silica gel column chromatography to obtain 280 mg of a compound represented by the following formula (hereinafter referred to as the present compound (14)).

Present Compound (14)

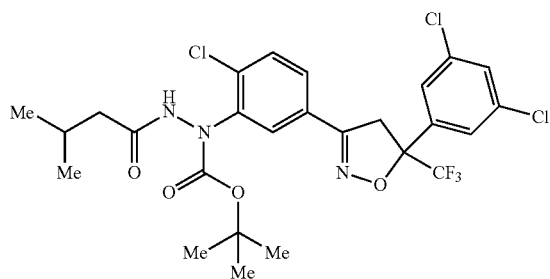 [SMILES: CC(C)CC(=O)NN(C(=O)OC(C)(C)C)c1cc(C2=NOC(c3cc(Cl)cc(Cl)c3)(C(F)(F)F)C2)ccc1Cl]

$^1$H-NMR (CDCl$_3$) δ: 7.82-7.70 (3H, m), 7.48-7.44 (4H, m), 4.08-4.04 (1H, m), 3.71-3.66 (1H, m), 2.18-2.10 (3H, m), 1.45 (9H, d, J=52.9 Hz), 0.98 (6H, d, J=6.1 Hz).

Production Example 15

To 280 mg of the present compound (14) was added 2 mL of trifluoroacetic acid at room temperature, followed by stirring at the same temperature for 2 hours. The reaction mixture was concentrated under reduced pressure and ethyl acetate was added to the residue. The organic layer was washed with an aqueous saturated sodium hydrogen carbonate solution, dried over anhydrous sodium sulfate and then concentrated under reduced pressure. The residue was subjected to silica gel column chromatography to obtain 222 mg of a compound represented by the following formula (hereinafter referred to as the present compound (15)).

Present Compound (15)

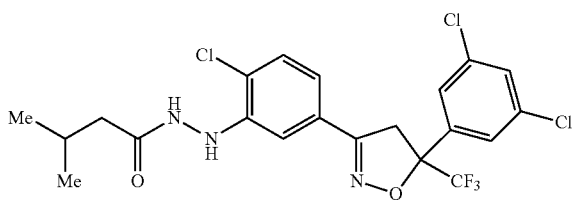 [SMILES: CC(C)CC(=O)NNc1cc(C2=NOC(c3cc(Cl)cc(Cl)c3)(C(F)(F)F)C2)ccc1Cl]

Melting point: 84° C.

Production Example 16

To a solution of 200 mg of a crude compound obtained in Reference Production Example 21 as described later and 57 mg of triethylamine in 1.5 ml of tetrahydrofuran was added dropwise 79 mg of benzoyl chloride at 0° C., followed by stirring at room temperature for 2 hours. The reaction mixture was concentrated under reduced pressure and the residue was subjected to silica gel column chromatography to obtain 220 mg of a compound represented by the following formula (hereinafter referred to as the present compound (16)).

Present Compound (16)

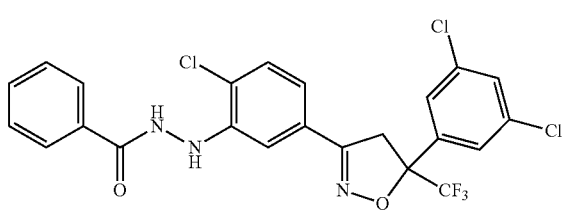

Melting point: 105° C.

Production Example 17

To a solution of 200 mg of a crude compound obtained in Reference Production Example 21 as described later and 57 mg of triethylamine in 2 ml of tetrahydrofuran was added dropwise 90 mg of 4,4,4-trifluorobutyryl chloride at 0° C., followed by stirring at room temperature for 2 hours. The reaction mixture was concentrated under reduced pressure and the residue was subjected to silica gel column chromatography to obtain 201 mg of a compound represented by the following formula (hereinafter referred to as the present compound (17)).

Present Compound (17)

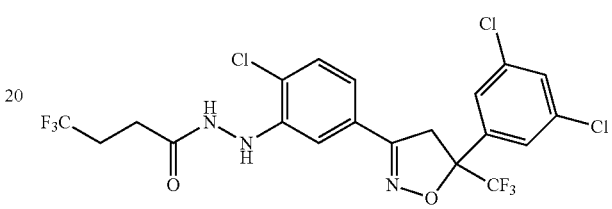

Melting point: 82° C.

Production Example 18

To a solution of 200 mg of a crude compound obtained in Reference Production Example 21 as described later and 57 mg of triethylamine in 4 ml of tetrahydrofuran was added dropwise 44 mg of acetyl chloride at 0° C., followed by stirring at room temperature for 2 hours. The reaction mixture was concentrated under reduced pressure and the residue was subjected to silica gel column chromatography to obtain 168 mg of a compound represented by the following formula (hereinafter referred to as the present compound (18)).

Present Compound (18)

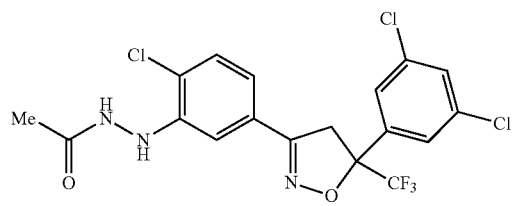 [SMILES: CC(=O)NNc1cc(C2=NOC(c3cc(Cl)cc(Cl)c3)(C(F)(F)F)C2)ccc1Cl]

Melting point: 94° C.

Production Example 19

To a solution of 200 mg of a crude compound obtained in Reference Production Example 21 as described later and 57 mg of triethylamine in 4 ml of tetrahydrofuran was added dropwise 52 mg of propionyl chloride at 0° C., followed by stirring at room temperature for 2 hours. The reaction mixture was concentrated under reduced pressure and the residue was subjected to silica gel column chromatography to obtain 195 mg of a compound represented by the following formula (hereinafter referred to as the present compound (19)).

Present Compound (19)

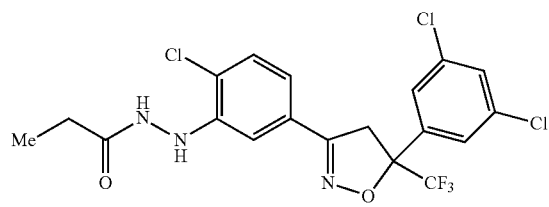 [SMILES: CCC(=O)NNc1cc(C2=NOC(c3cc(Cl)cc(Cl)c3)(C(F)(F)F)C2)ccc1Cl]

Melting point: 92° C.

Production Example 20

To a solution of 260 mg of a crude compound obtained in Reference Production Example 21 as described later and 60 mg of triethylamine in 2 ml of tetrahydrofuran was added dropwise 150 mg of trifluoroacetic anhydride at 0° C., followed by stirring at room temperature for 2 hours. The reaction mixture was concentrated under reduced pressure and the residue was subjected to silica gel column chromatography to obtain 175 mg of a compound represented by the following formula (hereinafter referred to as the present compound (20)).

Present Compound (20)

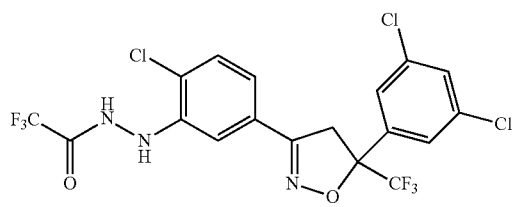

Melting point: 64° C.

Production Example 21

To a solution of 200 mg of a crude compound obtained in Reference Production Example 21 as described later and 95 mg of triethylamine in 4 ml of tetrahydrofuran was added 84 mg of nicotinoyl chloride hydrochloride at 0° C., followed by stirring at room temperature for 2 hours. The reaction mixture was concentrated under reduced pressure and the residue was subjected to silica gel column chromatography to obtain 198 mg of a compound represented by the following formula (hereinafter referred to as the present compound (21)).

Present Compound (21)

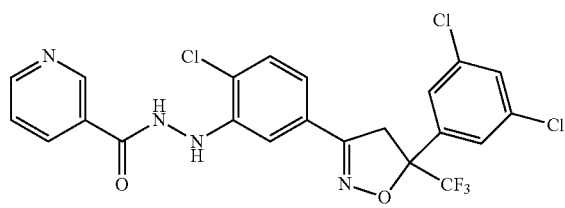 [SMILES: O=C(NNc1cc(C2=NOC(c3cc(Cl)cc(Cl)c3)(C(F)(F)F)C2)ccc1Cl)c1cccnc1]

Melting point: 205° C.

Production Example 22

To a solution of 200 mg of a crude compound obtained in Reference Production Example 21 as described later and 95 mg of triethylamine in 4 ml of tetrahydrofuran was added 84 mg of isonicotinoyl chloride hydrochloride at 0° C., followed by stirring at room temperature for 2 hours. The reaction mixture was concentrated under reduced pressure and the residue was subjected to silica gel column chromatography to obtain 169 mg of a compound represented by the following formula (hereinafter referred to as the present compound (22)).

Present Compound (22)

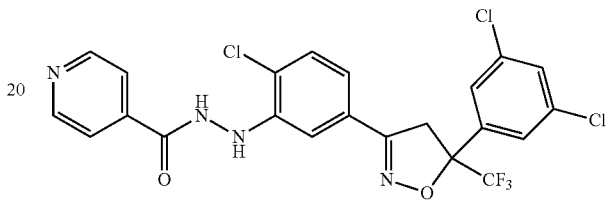

Melting point: 115° C.

Production Example 23

To a solution of 200 mg of a crude compound obtained in Reference Production Example 21 as described later and 52 mg of triethylamine in 4 ml of tetrahydrofuran was added 62 mg of pivaloyl chloride at 0° C., followed by stirring at room temperature for 2 hours. The reaction mixture was concentrated under reduced pressure and the residue was subjected to silica gel column chromatography to obtain 198 mg of a compound represented by the following formula (hereinafter referred to as the present compound (23)).

Present Compound (23)

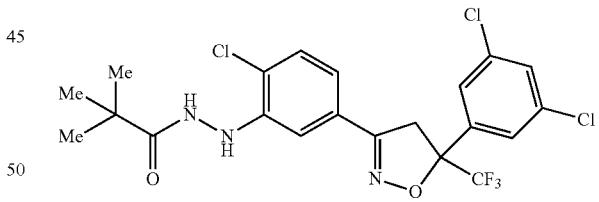

Melting point: 106° C.

Production Example 24

To a solution of 200 mg of a crude compound obtained in Reference Production Example 21 as described later and 57 mg of triethylamine in 4 ml of tetrahydrofuran was added 67 mg of dimethylcarbamoyl chloride at 0° C., followed by stirring at room temperature for 2 hours. The reaction mixture was concentrated under reduced pressure and the residue was subjected to silica gel column chromatography to obtain 70 mg of a compound represented by the following formula (hereinafter referred to as the present compound (24)).

Present Compound (24)

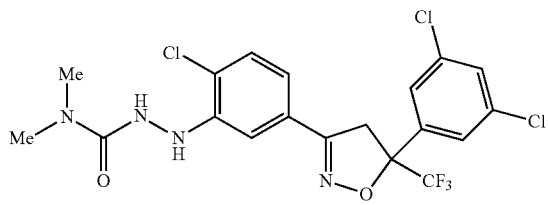 [SMILES: CN(C)C(=O)NNc1cc(C2=NOC(c3cc(Cl)cc(Cl)c3)(C(F)(F)F)C2)ccc1Cl]

Melting point: 212° C.

Production Example 25

To a solution of 200 mg of a crude compound obtained in Reference Production Example 21 as described later and 51 mg of triethylamine in 4 ml of tetrahydrofuran was added 37 mg of ethyl isocyanate at 0° C., followed by stirring at room temperature for 2 hours. The reaction mixture was concentrated under reduced pressure and the residue was subjected to silica gel column chromatography to obtain 149 mg of a compound represented by the following formula (hereinafter referred to as the present compound (25)).
Present Compound (25)

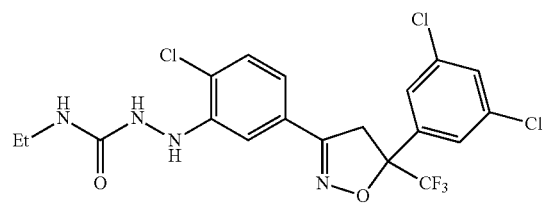 [SMILES: CCNC(=O)NNc1cc(C2=NOC(c3cc(Cl)cc(Cl)c3)(C(F)(F)F)C2)ccc1Cl]

Melting point: 102° C.

Production Example 26

To a solution of 200 mg of a crude compound obtained in Reference Production Example 21 as described later and 57 mg of triethylamine in 4 ml of tetrahydrofuran was added 79 mg of phenylacetyl chloride at 0° C., followed by stirring at room temperature for 2 hours. The reaction mixture was concentrated under reduced pressure and the residue was subjected to silica gel column chromatography to obtain 211 mg of a compound represented by the following formula (hereinafter referred to as the present compound (26)).
Present Compound (26)

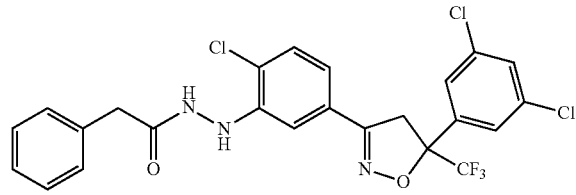 [SMILES: O=C(Cc1ccccc1)NNc1cc(C2=NOC(c3cc(Cl)cc(Cl)c3)(C(F)(F)F)C2)ccc1Cl]

Melting point: 173° C.

Production Example 27

To a solution of 500 mg of a compound obtained in Reference Production Example 23 as described later and 122 mg of acrylic acid in 2 ml of N,N-dimethylformamide was added 319 mg of 1-ethyl-3-(3-dimethylaminopropyl)carbodiimide hydrochloride at room temperature, followed by stirring for 3 hours. To the reaction mixture was added water, followed by extraction with ethyl acetate. The organic layer was dried over anhydrous sodium sulfate and then concentrated under reduced pressure. The residue was subjected to silica gel column chromatography to obtain 384 mg of a compound represented by the following formula (hereinafter referred to as the present compound (27)).
Present Compound (27)

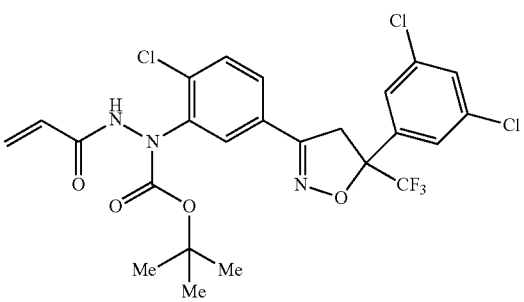 [SMILES: C=CC(=O)NN(C(=O)OC(C)(C)C)c1cc(C2=NOC(c3cc(Cl)cc(Cl)c3)(C(F)(F)F)C2)ccc1Cl]

Melting point: 119° C.

Production Example 28

To 309 mg of the compound obtained by Production Example 27 was added 2 mL of trifluoroacetic acid at room temperature, followed by stirring at the same temperature for 2 hours. The reaction mixture was concentrated under reduced pressure and ethyl acetate was added to the residue. The organic layer was washed with an aqueous saturated sodium hydrogen carbonate solution, dried over anhydrous sodium sulfate and then concentrated under reduced pressure. The residue was subjected to silica gel column chromatography to obtain 238 mg of a compound represented by the following formula (hereinafter referred to as the present compound (28)).
Present Compound (28)

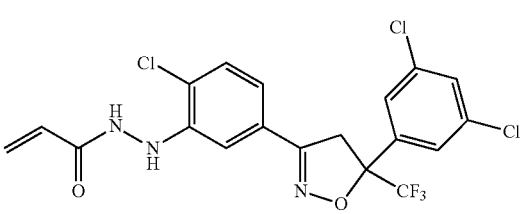 [SMILES: C=CC(=O)NNc1cc(C2=NOC(c3cc(Cl)cc(Cl)c3)(C(F)(F)F)C2)ccc1Cl]

Melting point: 90° C.

Production Example 29

To a solution of 200 mg of a compound obtained in Reference Production Example 28 as described later and 57 mg of triethylamine in 2.0 mL of tetrahydrofuran was added dropwise 58 mg of cyclopropanecarbonyl chloride at room temperature, followed by stirring at the same temperature for 30 minutes. The reaction mixture was concentrated under reduced pressure and the residue was subjected to silica gel column chromatography to obtain 225 mg of a compound represented by the following formula (hereinafter referred to as the present compound (29)).

Present Compound (29)

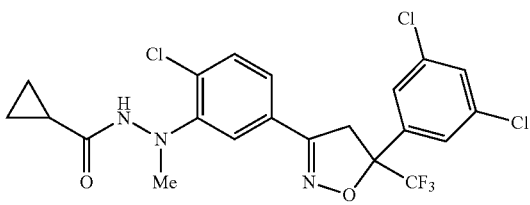 [SMILES: CN(NC(=O)C1CC1)c1cc(C2=NOC(c3cc(Cl)cc(Cl)c3)(C(F)(F)F)C2)ccc1Cl]

Melting point: 176° C.

Production Example 30

To a solution of 200 mg of a compound obtained in Reference Production Example 28 as described later and 57 mg of triethylamine in 2.0 mL of tetrahydrofuran was added dropwise 81 mg of 3,3,3-trifluoropropionyl chloride at room temperature, followed by stirring at the same temperature for 30 minutes. The reaction mixture was concentrated under reduced pressure and the residue was subjected to silica gel column chromatography to obtain 241 mg of a compound represented by the following formula (hereinafter referred to as the present compound (30)).

Present Compound (30)

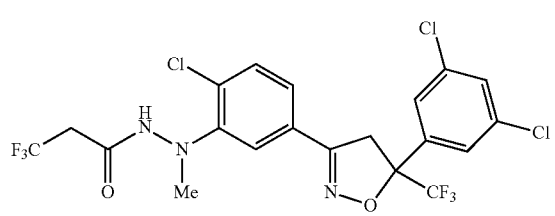 [SMILES: CN(NC(=O)CC(F)(F)F)c1cc(C2=NOC(c3cc(Cl)cc(Cl)c3)(C(F)(F)F)C2)ccc1Cl]

Melting point: 81° C.

Production Example 31

To a solution of 200 mg of a compound obtained in Reference Production Example 28 as described later and 57 mg of triethylamine in 2.0 mL of tetrahydrofuran was added dropwise 88 mg of 4,4,4-trifluorobutyryl chloride at room temperature, followed by stirring at the same temperature for 1 hour. The reaction mixture was concentrated under reduced pressure and the residue was subjected to silica gel column chromatography to obtain 258 mg of a compound represented by the following formula (hereinafter referred to as the present compound (31)).

Present Compound (31)

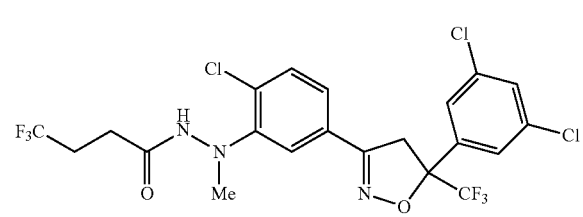 [SMILES: CN(NC(=O)CCC(F)(F)F)c1cc(C2=NOC(c3cc(Cl)cc(Cl)c3)(C(F)(F)F)C2)ccc1Cl]

Melting point: 77° C.

Production Example 32

To a solution of 200 mg of a compound obtained in Reference Production Example 28 as described later and 57 mg of triethylamine in 2.0 mL of tetrahydrofuran was added dropwise 43 mg of acetyl chloride at room temperature, followed by stirring at the same temperature for 1 hour. The reaction mixture was concentrated under reduced pressure and the residue was subjected to silica gel column chromatography to obtain 204 mg of a compound represented by the following formula (hereinafter referred to as the present compound (32)).

Present Compound (32)

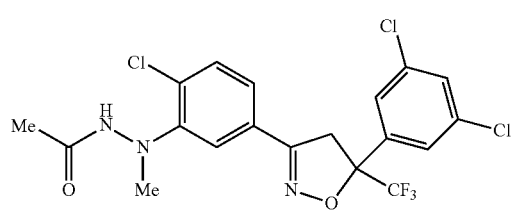 [SMILES: CC(=O)NN(C)c1cc(C2=NOC(c3cc(Cl)cc(Cl)c3)(C(F)(F)F)C2)ccc1Cl]

$^1$H-NMR (CDCl$_3$) δ: 7.88-7.24 (7H, m), 4.09-4.04 (1H, m), 3.70-3.66 (1H, m), 3.29-3.07 (3H, m), 2.17-1.91 (3H, m).

Production Example 33

To a solution of 525 mg of a compound obtained in Reference Production Example 23 as described later and 121 mg of triethylamine in 4 mL of tetrahydrofuran was added dropwise 223 mg of 4-bromobutyryl chloride at room temperature, followed by stirring for 1 hour. To the reaction mixture was added water, followed by extraction with ethyl acetate. The organic layer was dried over anhydrous sodium sulfate and then concentrated under reduced pressure to obtain 699 mg of a crude compound represented by the following formula (hereinafter referred to as the present compound (33)).

Present Compound (33)

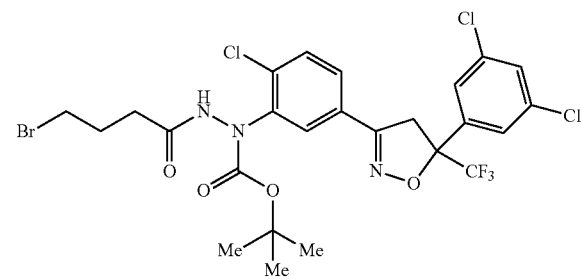 [SMILES: CC(C)(C)OC(=O)N(NC(=O)CCCBr)c1cc(C2=NOC(c3cc(Cl)cc(Cl)c3)(C(F)(F)F)C2)ccc1Cl]

Production Example 34

To 309 mg of the present compound (33) was added 2 mL of trifluoroacetic acid, followed by stirring at room temperature for 2 hours. The reaction mixture was concentrated under reduced pressure and ethyl acetate was added to the residue. The organic layer was washed with an aqueous saturated sodium hydrogen carbonate solution, dried over anhydrous sodium sulfate and then concentrated under reduced pressure. The residue was subjected to silica gel column chromatography to obtain 573 mg of a compound represented by the following formula (hereinafter referred to as the present compound (34)).

Present Compound (34)

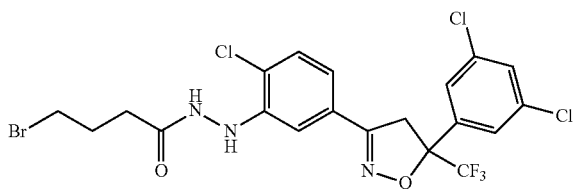 [SMILES: O=C(CCCBr)NNc1cc(C2=NOC(c3cc(Cl)cc(Cl)c3)(C(F)(F)F)C2)ccc1Cl]

Melting point: 59° C.

Production Example 35

To a solution of 350 mg of a compound obtained in Reference Production Example 23 as described later and 187 mg of 5,5,5-trifluoropentanoic acid in 2 ml of N,N-dimethylformamide was added 153 mg of 1-ethyl-3-(3-dimethylaminopropyl)carbodiimide hydrochloride at room temperature, followed by stirring for 3 hours. To the reaction mixture was added water, followed by extraction with ethyl acetate. The organic layer was dried over anhydrous sodium sulfate and then concentrated under reduced pressure to obtain 350 mg of a crude compound represented by the following formula (hereinafter referred to as the present compound (35)).
Present Compound (35)

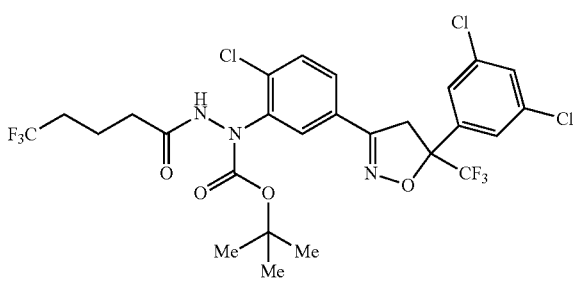 [SMILES: CC(C)(C)OC(=O)N(NC(=O)CCCC(F)(F)F)c1cc(C2=NOC(c3cc(Cl)cc(Cl)c3)(C(F)(F)F)C2)ccc1Cl]

Production Example 36

To 350 mg of the present compound (35) was added 2 mL of trifluoroacetic acid at room temperature, followed by stirring at the same temperature for 2 hours. The reaction mixture was concentrated under reduced pressure and ethyl acetate was added to the residue. The organic layer was washed with an aqueous saturated sodium hydrogen carbonate solution, dried over anhydrous sodium sulfate and then concentrated under reduced pressure. The residue was subjected to silica gel column chromatography to obtain 269 mg of a compound represented by the following formula (hereinafter referred to as the present compound (36)).
Present Compound (36)

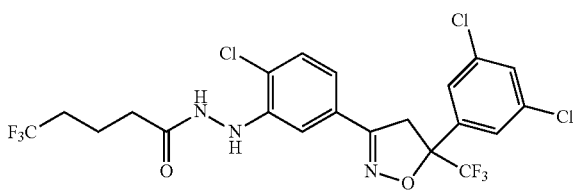 [SMILES: O=C(CCCC(F)(F)F)NNc1cc(C2=NOC(c3cc(Cl)cc(Cl)c3)(C(F)(F)F)C2)ccc1Cl]

Melting point: 163° C.

Production Example 37

To a solution of 367 mg of a compound obtained in Reference Production Example 23 as described later and 84 mg of triethylamine in 2 mL of tetrahydrofuran was added dropwise 91 mg of methoxyacetyl chloride at room temperature, followed by stirring for 1 hour. To the reaction mixture was added ethyl acetate. The organic layer was washed with water, dried over anhydrous sodium sulfate, and then concentrated under reduced pressure to obtain 377 mg of a crude compound represented by the following formula (hereinafter referred to as the present compound (37)).
Present Compound (37)

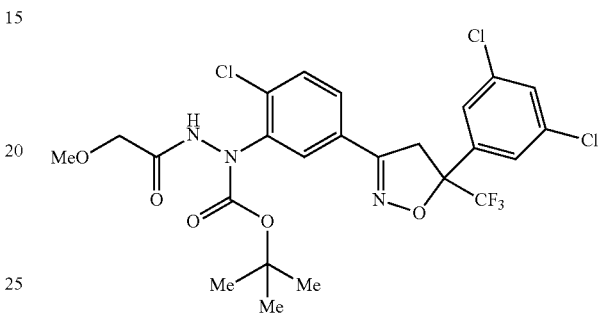

Production Example 38

To 309 mg of the crude present compound (37) was added 2 mL of trifluoroacetic acid at room temperature, followed by stirring at the same temperature for 2 hours. The reaction mixture was concentrated under reduced pressure and ethyl acetate was added to the residue. The organic layer was washed with an aqueous saturated sodium hydrogen carbonate solution, dried over anhydrous sodium sulfate and then concentrated under reduced pressure. The residue was subjected to silica gel column chromatography to obtain 276 mg of a compound represented by the following formula (hereinafter referred to as the present compound (38)).
Present Compound (38)

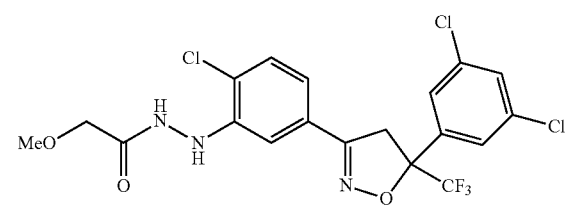 [SMILES: COCC(=O)NNc1cc(C2=NOC(c3cc(Cl)cc(Cl)c3)(C(F)(F)F)C2)ccc1Cl]

Melting point: 178° C.

Production Example 39

To a solution of 524 mg of a compound obtained in Reference Production Example 23 as described later and 121 mg of triethylamine in 4 mL of tetrahydrofuran was added dropwise 186 mg of 3-chloropivaloyl chloride at room temperature, followed by stirring at the same temperature for 1 hour. To the reaction mixture was added ethyl acetate. The organic layer was washed with water, dried over anhydrous sodium sulfate, and then concentrated under reduced pressure to obtain 643 mg of a crude compound represented by the following formula (hereinafter referred to as the present compound (39)).

Present Compound (39)

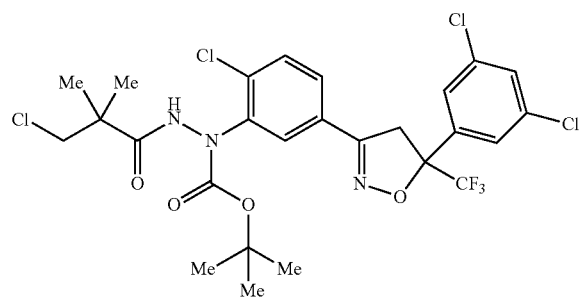 [SMILES: CC(C)(C)OC(=O)N(NC(=O)C(C)(C)CCl)c1cc(C2=NOC(c3cc(Cl)cc(Cl)c3)(C(F)(F)F)C2)ccc1Cl]

Production Example 40

To 643 mg of the crude present compound (39) was added 5 mL of trifluoroacetic acid, followed by stirring at room temperature for 2 hours. The reaction mixture was concentrated under reduced pressure and ethyl acetate was added to the residue. The organic layer was washed with an aqueous saturated sodium hydrogen carbonate solution, dried over anhydrous sodium sulfate, and then concentrated under reduced pressure to obtain 520 mg of a compound represented by the following formula (hereinafter referred to as the present compound (40)).
Present Compound (40)

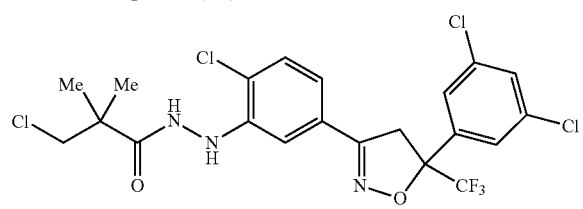

$^1$H-NMR (CDCl$_3$) δ: 7.68 (1H, d, J=3.2 Hz), 7.47 (2H, d, J=1.7 Hz), 7.42 (1H, t, J=2.0 Hz), 7.32 (1H, d, J=8.3 Hz), 7.26 (1H, d, J=1.5 Hz), 7.06 (1H, dd, J=8.2, 2.1 Hz), 6.45 (1H, d, J=3.2 Hz), 4.00 (1H, d, J=17.6 Hz), 3.68 (2H, s), 3.63 (1H, d, J=17.6 Hz), 1.42 (3H, s), 1.41 (3H, s).

Production Example 41

To a solution of 200 mg of a crude compound obtained in Reference Production Example 21 as described later and 56 mg of triethylamine in 4 ml of tetrahydrofuran was added 103 mg of 4-nitrobenzoyl chloride at 0° C., followed by stirring at room temperature for 10 minutes. The reaction mixture was concentrated under reduced pressure and the residue was subjected to silica gel column chromatography to obtain 166 mg of a compound represented by the following formula (hereinafter referred to as the present compound (41)).
Present Compound (41)

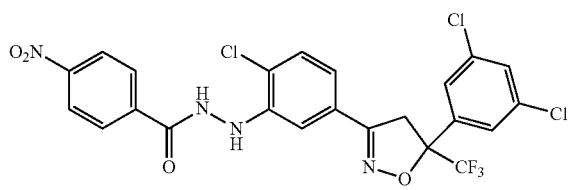 [SMILES: O=C(NNc1cc(C2=NOC(c3cc(Cl)cc(Cl)c3)(C(F)(F)F)C2)ccc1Cl)c1ccc([N+](=O)[O-])cc1]

Melting point: 231° C.

Production Example 42

To a solution of 200 mg of a crude compound obtained in Reference Production Example 21 and 57 mg of triethylamine in 4 ml of tetrahydrofuran was added 50 mg of butyryl chloride at 0° C., followed by stirring at room temperature for 20 minutes. The reaction mixture was concentrated under reduced pressure and the residue was subjected to silica gel column chromatography to obtain 121 mg of a compound represented by the following formula (hereinafter referred to as the present compound (42)).
Present Compound (42)

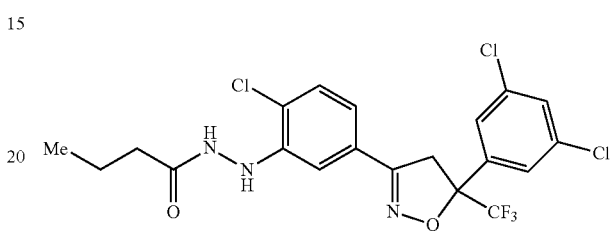

Melting point: 82° C.

Production Example 43

To a solution of 200 mg of a crude compound obtained in Reference Production Example 21 as described later and 57 mg of triethylamine in 4 ml of tetrahydrofuran was added 57 mg of pentanoyl chloride at 0° C., followed by stirring at room temperature for 2 hours. The reaction mixture was concentrated under reduced pressure and the residue was subjected to silica gel column chromatography to obtain 164 mg of a compound represented by the following formula (hereinafter referred to as the present compound (43)).
Present Compound (43)

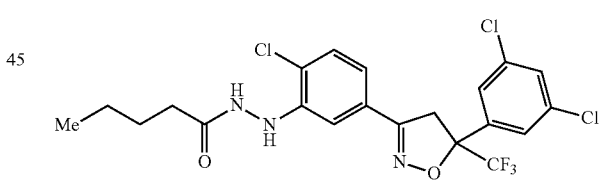

Melting point: 89° C.

Production Example 44

To a solution of 200 mg of a crude compound obtained in Reference Production Example 21 as described later and 57 mg of triethylamine in 4 ml of tetrahydrofuran was added 63 mg of hexanoyl chloride at 0° C., followed by stirring at room temperature for 20 minutes. The reaction mixture was concentrated under reduced pressure and the residue was subjected to silica gel column chromatography to obtain 134 mg of a compound represented by the following formula (hereinafter referred to as the present compound (44)).

Present Compound (44)

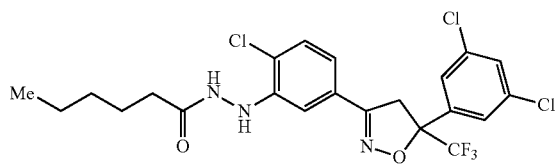 [SMILES: CCCCCC(=O)NNc1cc(C2=NOC(c3cc(Cl)cc(Cl)c3)(C(F)(F)F)C2)ccc1Cl]

Melting point: 80° C.

Production Example 45

To a solution of 200 mg of a the crude compound obtained in Reference Production Example 21 as described later and 57 mg of triethylamine in 4 ml of tetrahydrofuran was added 78 mg of cinnamoyl chloride at 0° C., followed by stirring at room temperature for 20 minutes. The reaction mixture was concentrated under reduced pressure and the residue was subjected to silica gel column chromatography to obtain 161 mg of a compound represented by the following formula (hereinafter referred to as the present compound (45)).
Present Compound (45)

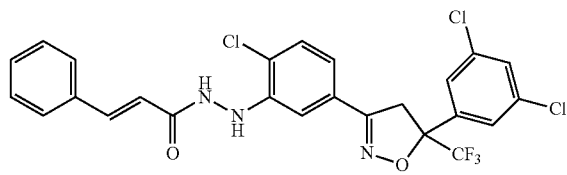 [SMILES: O=C(/C=C/c1ccccc1)NNc1cc(C2=NOC(c3cc(Cl)cc(Cl)c3)(C(F)(F)F)C2)ccc1Cl]

Melting point: 205° C.

Production Example 46

To a solution of 247 mg of a compound obtained in Reference Production Example 23 as described later and 56 mg of triethylamine in 2 mL of tetrahydrofuran was added 95 mg of 4-methoxybenzoyl chloride at room temperature, followed by stirring for 1 hour. To the reaction mixture was added ethyl acetate. The organic layer was washed with water, dried over anhydrous sodium sulfate, and then concentrated under reduced pressure to obtain 240 mg of a crude compound represented by the following formula (hereinafter referred to as the present compound (46)).
Present Compound (46)

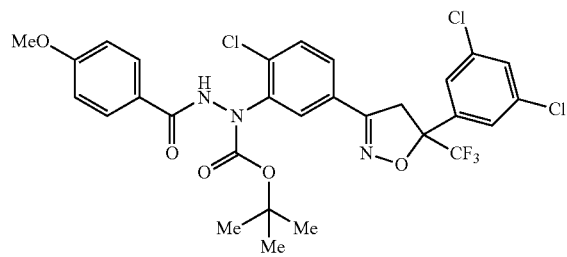 [SMILES: COc1ccc(C(=O)NN(C(=O)OC(C)(C)C)c2cc(C3=NOC(c4cc(Cl)cc(Cl)c4)(C(F)(F)F)C3)ccc2Cl)cc1]

Production Example 47

To 240 mg of the present compound (46) was added 2 mL of trifluoroacetic acid, followed by stirring at room temperature for 1 hour. The reaction mixture was concentrated under reduced pressure and ethyl acetate was added to the residue. The organic layer was washed with an aqueous saturated sodium hydrogen carbonate solution, dried over anhydrous sodium sulfate, and then concentrated under reduced pressure to obtain 221 mg of a compound represented by the following formula (hereinafter referred to as the present compound (47)).
Present Compound (47)

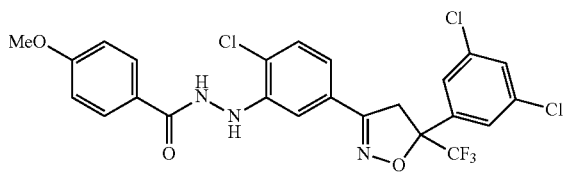 [SMILES: COc1ccc(C(=O)NNc2cc(C3=NOC(c4cc(Cl)cc(Cl)c4)(C(F)(F)F)C3)ccc2Cl)cc1]

Melting point: 131° C.

Production Example 48

To a solution of 1.31 g of a compound obtained in Reference Production Example 31 as described later and 200 mg of triethylamine in 4 mL of tetrahydrofuran was added dropwise 290 mg of 3,3,3-trifluoropropionyl chloride at room temperature, followed by stirring at the same temperature for 1 hour. The reaction mixture was concentrated under reduced pressure and the residue was subjected to silica gel column chromatography to obtain 426 mg of a compound represented by the following formula (hereinafter referred to as the present compound (48)).
Present Compound (48)

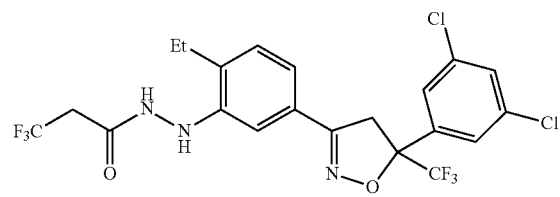 [SMILES: CCc1ccc(C2=NOC(c3cc(Cl)cc(Cl)c3)(C(F)(F)F)C2)cc1NNC(=O)CC(F)(F)F]

Melting point: 138.7° C.

Production Example 49

To a solution of 200 mg of a compound obtained in Reference Production Example 33 as described later and 65 mg of triethylamine in 2 mL of tetrahydrofuran was added dropwise 54 mg of cyclopropanecarbonyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 216 mg of a compound represented by the following formula (hereinafter referred to as the present compound (49)).

Present Compound (49)

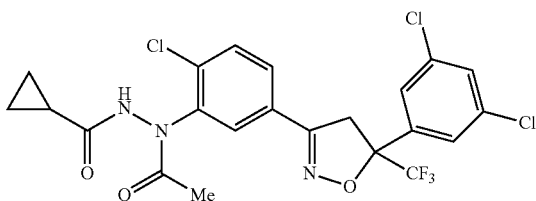

Melting point: 160° C.

Production Example 50

To a solution of 200 mg of a compound obtained in Reference Production Example 33 as described later and 65 mg of triethylamine in 2 mL of tetrahydrofuran was added dropwise 55 mg of methoxyacetyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 130 mg of a compound represented by the following formula (hereinafter referred to as the present compound (50)).
Present Compound (50)

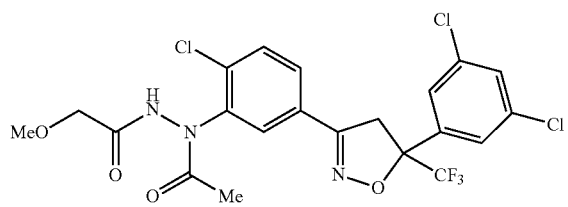 [SMILES: COCC(=O)NN(C(C)=O)c1cc(C2=NOC(c3cc(Cl)cc(Cl)c3)(C(F)(F)F)C2)ccc1Cl]

Melting point: 164° C.

Production Example 51

To a solution of 200 mg of a compound obtained in Reference Production Example 33 as described later and 65 mg of triethylamine in 2 mL of tetrahydrofuran was added dropwise 40 mg of acetyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 140 mg of a compound represented by the following formula (hereinafter referred to as the present compound (51)).
Present Compound (51)

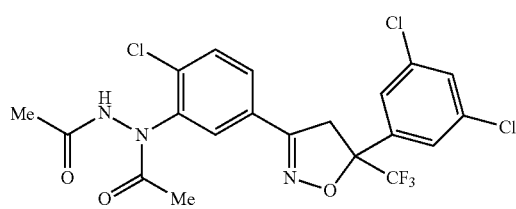

Melting point: 108° C.

Production Example 52

To a solution of 200 mg of a compound obtained in Reference Production Example 33 as described later and 65 mg of triethylamine in 2 mL of tetrahydrofuran was added dropwise 72 mg of benzoyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 281 mg of a compound represented by the following formula (hereinafter referred to as the present compound (52)).
Present Compound (52)

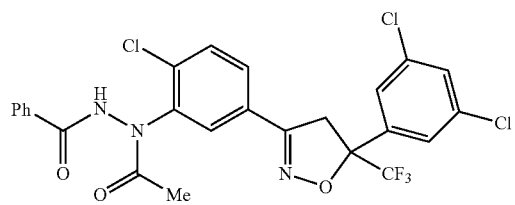 [SMILES: CC(=O)N(NC(=O)c1ccccc1)c1cc(C2=NOC(c3cc(Cl)cc(Cl)c3)(C(F)(F)F)C2)ccc1Cl]

Melting point: 107° C.

Production Example 53

To a solution of 200 mg of a compound obtained in Reference Production Example 33 as described later and 65 mg of triethylamine in 2 mL of tetrahydrofuran was added dropwise 90 mg of 4,4,4-trifluorobutylyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 207 mg of a compound represented by the following formula (hereinafter referred to as the present compound (53)).
Present Compound (53)

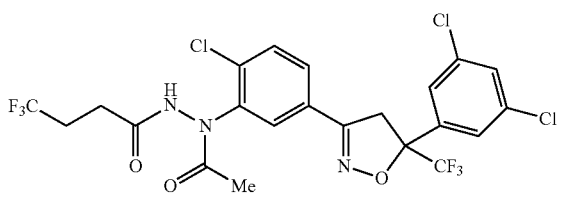 [SMILES: CC(=O)N(NC(=O)CCC(F)(F)F)c1cc(C2=NOC(c3cc(Cl)cc(Cl)c3)(C(F)(F)F)C2)ccc1Cl]

Melting point: 117° C.

Production Example 54

To a solution of 200 mg of a compound obtained in Reference Production Example 35 as described later and 58 mg of triethylamine in 2 mL of tetrahydrofuran was added dropwise 38 mg of acetyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 156 mg of a compound represented by the following formula (hereinafter referred to as the present compound (54)).

Present Compound (54)

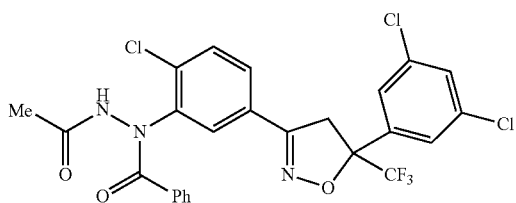

Melting point: 172° C.

Production Example 55

To a solution of 200 mg of a compound obtained in Reference Production Example 35 as described later and 51 mg of triethylamine in 2 mL of tetrahydrofuran was added dropwise 54 mg of cyclopropanecarbonyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 103 mg of a compound represented by the following formula (hereinafter referred to as the present compound (55)).
Present Compound (55)

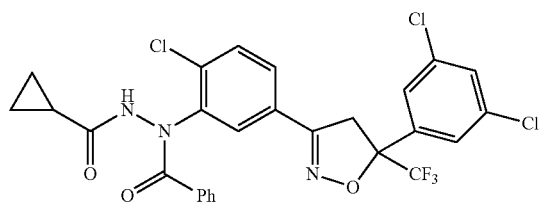 [SMILES: O=C(NN(C(=O)c1ccccc1)c1cc(C2=NOC(c3cc(Cl)cc(Cl)c3)(C(F)(F)F)C2)ccc1Cl)C1CC1]

Melting point: 157° C.

Production Example 56

To a solution of 200 mg of a compound obtained in Reference Production Example 35 as described later and 65 mg of triethylamine in 2 mL of tetrahydrofuran was added dropwise 78 mg of 4,4,4-trifluorobutylyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 211 mg of a compound represented by the following formula (hereinafter referred to as the present compound (56)).
Present Compound (56)

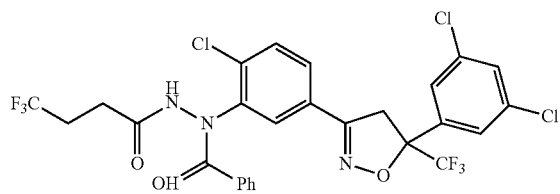 [SMILES: O=C(CCC(F)(F)F)NN(C(=O)c1ccccc1)c1cc(C2=NOC(c3cc(Cl)cc(Cl)c3)(C(F)(F)F)C2)ccc1Cl]

Melting point: 104° C.

Production Example 57

To a solution of 300 mg of a compound obtained in Reference Production Example 35 as described later and 85 mg of triethylamine in 2 mL of tetrahydrofuran was added dropwise 79 mg of methoxyacetyl chloride at room temperature, followed by stirring at the same temperature for 1 hour. To the reaction mixture was added ethyl acetate. The organic layer was washed with water, dried over anhydrous sodium sulfate, and then concentrated under reduced pressure. The residue was subjected to silica gel column chromatography to obtain 297 mg of a compound represented by the following formula (hereinafter referred to as the present compound (57)).
Present Compound (57)

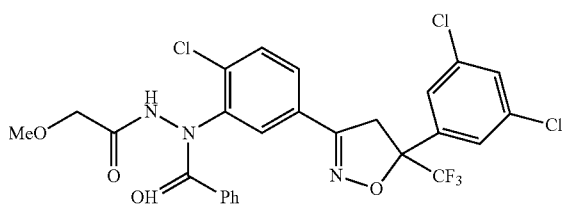 [SMILES: COCC(=O)NN(C(=O)c1ccccc1)c1cc(C2=NOC(c3cc(Cl)cc(Cl)c3)(C(F)(F)F)C2)ccc1Cl]

Melting point: 92° C.

Production Example 58

To a solution of 241 mg of a crude compound obtained in Reference Production Example 21 as described later in 2 mL of tetrahydrofuran was added dropwise 82 mg of phenyl isocyanate at room temperature, followed by stirring at the same temperature for 3 hours. The reaction mixture was concentrated under reduced pressure. The residue was subjected to silica gel column chromatography to obtain 187 mg of a compound represented by the following formula (hereinafter referred to as the present compound (58)).

Present Compound (58)

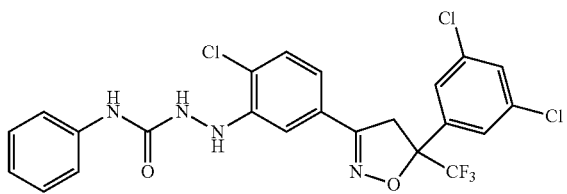 [SMILES: O=C(NNc1cc(C2=NOC(c3cc(Cl)cc(Cl)c3)(C(F)(F)F)C2)ccc1Cl)Nc1ccccc1]

Melting point: 131° C.

Production Example 59

To a solution of 200 mg of a crude compound obtained in Reference Production Example 21 as described later in 6 mL of tetrahydrofuran was added dropwise 85 mg of 4-methoxyphenyl isocyanate at room temperature, followed by stirring at the same temperature for 3 hours. The reaction mixture was concentrated under reduced pressure. The residue was subjected to silica gel column chromatography to obtain 191 mg of a compound represented by the following formula (hereinafter referred to as the present compound (59)).

Present Compound (59)

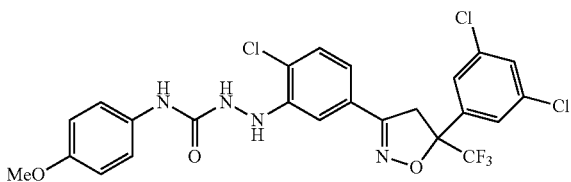 [SMILES: COc1ccc(NC(=O)NNc2cc(C3=NOC(c4cc(Cl)cc(Cl)c4)(C(F)(F)F)C3)ccc2Cl)cc1]

Melting point: 131° C.

Production Example 60

To a solution of 196 mg of a crude compound obtained in Reference Production Example 21 as described later in 5 mL of tetrahydrofuran was added dropwise 136 mg of 4-nitrophenyl isocyanate at room temperature, followed by stirring at the same temperature for 3 hours. The reaction mixture was concentrated under reduced pressure. The residue was subjected to silica gel column chromatography to obtain 110 mg of a compound represented by the following formula (hereinafter referred to as the present compound (60)).
Present Compound (60)

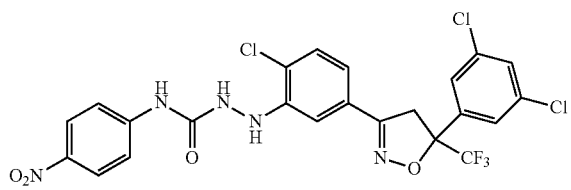 [SMILES: O=C(NNc1cc(C2=NOC(c3cc(Cl)cc(Cl)c3)(C(F)(F)F)C2)ccc1Cl)Nc1ccc([N+](=O)[O-])cc1]

Melting point: 201° C.

Production Example 61

To a solution of 220 mg of a crude compound obtained in Reference Production Example 21 as described later in 6 mL of tetrahydrofuran was added dropwise 79 mg of cyclohexyl isocyanate at room temperature, followed by stirring at the same temperature for 3 hours. The reaction mixture was concentrated under reduced pressure. The residue was subjected to silica gel column chromatography to obtain 100 mg of a compound represented by the following formula (hereinafter referred to as the present compound (61)).
Present Compound (61)

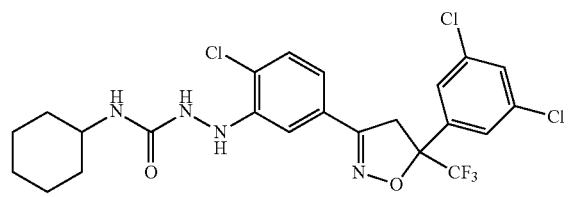 [SMILES: O=C(NNc1cc(C2=NOC(c3cc(Cl)cc(Cl)c3)(C(F)(F)F)C2)ccc1Cl)NC1CCCCC1]

Melting point: 101° C.

Production Example 62

To a solution of 340 mg of a crude compound obtained in Reference Production Example 21 as described later in 6 mL of tetrahydrofuran was added dropwise 173 mg of cyclohexyl isothiocyanate at room temperature, followed by stirring at the same temperature for 3 hours. The reaction mixture was concentrated under reduced pressure. The residue was subjected to silica gel column chromatography to obtain 135 mg of a compound represented by the following formula (hereinafter referred to as the present compound (62)).
Present Compound (62)

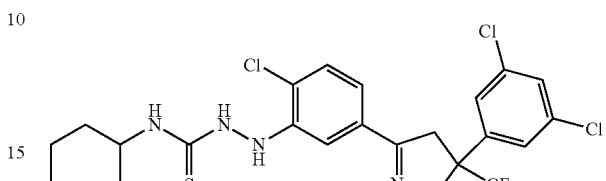

Melting point: 126° C.

Production Example 63

To a solution of 240 mg of a crude compound obtained in Reference Production Example 21 as described later in 6 mL of tetrahydrofuran was added dropwise 114 mg of phenyl isothiocyanate at room temperature, followed by stirring at the same temperature for 3 hours. The reaction mixture was concentrated under reduced pressure. The residue was subjected to silica gel column chromatography to obtain 200 mg of a compound represented by the following formula (hereinafter referred to as the present compound (63)).
Present Compound (63)

Melting point: 213° C.

Next, production of intermediates for producing the compound of the present invention is shown as Reference Production Examples.

Reference Production Example 1

To a solution of 249 mg of 3-nitrobenzaldoxime in 15 ml of N,N-dimethylformamide was added 201 mg of N-chlorosuccinimide at room temperature, followed by stirring at 60° C. for 1 hour. The reaction solution was cooled to room temperature, and thereto were added 362 mg of 2-(3,5-dichlorophenyl)-3,3,3-trifluoro-1-propene and then 152 mg of triethylamine, followed by stirring at room temperature for 6 hours. To the reaction mixture was added water, followed by extraction with ethyl acetate. The organic layer was dried over anhydrous sodium sulfate and then concentrated under reduced pressure. The residue was subjected to silica gel column chromatography to obtain 232 mg of a compound represented by the following formula.

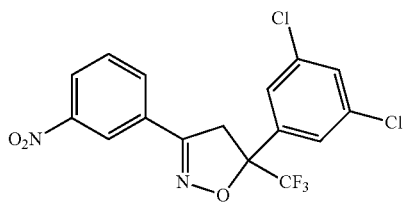

¹H-NMR (CDCl₃) δ: 8.43 (1H, br s), 8.34-8.32 (1H, m), 8.10 (1H, d, J=8.0 Hz), 7.67-7.65 (1H, m), 7.52 (2H, s), 7.45-7.45 (1H, m), 4.14 (1H, d, J=17.3 Hz), 3.76 (1H, d, J=17.3 Hz).

Reference Production Example 2

To 1 ml of an aqueous 2.5% acetic acid solution was added 192 mg of iron powder (10 to 20 mesh). Thereto was added a suspension of 232 mg of the compound prepared in Reference Production Example in 1.5 ml of ethanol at 75° C., followed by stirring at the same temperature for 15 minutes. Further 300 mg of iron powder was added thereto, followed by stirring at room temperature for 1 hour. The reaction mixture was cooled to room temperature, filtered, and then washed with ethyl acetate. The filtrate was extracted by adding water and ethyl acetate. The organic layer was dried over anhydrous sodium sulfate and then concentrated under reduced pressure. The residue was subjected to silica gel column chromatography to obtain 198 mg of a compound represented by the following formula.

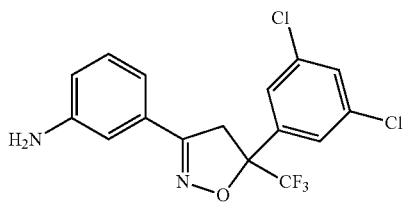 [SMILES: O=[N+]([O-])c1cccc(C2=NOC(c3cc(Cl)cc(Cl)c3)(C(F)(F)F)C2)c1]

¹H-NMR (CDCl₃) δ: 7.51 (2H, br s), 7.42 (1H, t, J=1.9 Hz), 7.20 (1H, t, J=7.8 Hz), 7.04 (1H, t, J=1.9 Hz), 6.95-6.93 (1H, m), 6.77-6.75 (1H, m), 4.05 (1H, d, J=17.1 Hz), 3.77 (2H, br s), 3.66 (1H, d, J=17.1 Hz).

Reference Production Example 3

To a solution of 1.0 g of the compound prepared in Reference Production Example 2 in 4 mL of 1,4-dioxane was added 7 mL of concentrated hydrochloric acid at room temperature. After stirring at the same temperature for 20 minutes, the solution was cooled to 0° C. and a solution of 184 mg of sodium nitrite in 4 mL of water was added dropwise thereto. After stirring at the same temperature for 15 minutes, to the reaction solution was added dropwise a solution of 1.11 g of tin (II) chloride in 2 mL of concentrated hydrochloric acid. The reaction mixture was neutralized by addition of 2 N sodium hydroxide and then the aqueous layer was extracted with ethyl acetate. The organic layer was dried over anhydrous sodium sulfate and then concentrated under reduced pressure to obtain 1.0 g of a crude compound represented by the following formula.

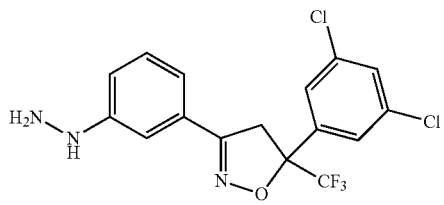 [SMILES: NNc1cccc(C2=NOC(c3cc(Cl)cc(Cl)c3)(C(F)(F)F)C2)c1]

Reference Production Example 4

To a solution of 3.0 g of the compound prepared in Reference Production Example 2 and 971 mg of triethylamine in 20 mL of tetrahydrofuran was added dropwise 1.85 g of trifluoroacetic anhydride at 0° C. After stirring at the same temperature for 15 minute, an aqueous saturated sodium hydrogen carbonate solution was added thereto, followed by extraction with ethyl acetate. The organic layer was dried over anhydrous sodium sulfate and then concentrated under reduced pressure to obtain 3.84 g of a compound represented by the following formula.

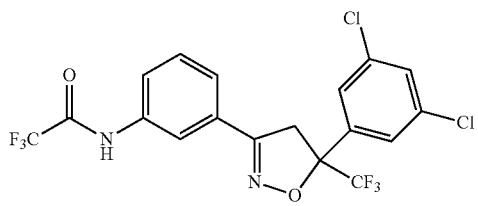 [SMILES: O=C(Nc1cccc(C2=NOC(c3cc(Cl)cc(Cl)c3)(C(F)(F)F)C2)c1)C(F)(F)F]

¹H-NMR (CDCl₃) δ: 8.02 (1H, br s), 7.94 (1H, t, J=1.8 Hz), 7.66-7.64 (1H, m), 7.57-7.55 (1H, m), 7.49-7.43 (4H, m), 4.09 (1H, d, J=17.3 Hz), 3.71 (1H, d, J=17.3 Hz).

Reference Production Example 5

To a solution of 3.84 g of the compound prepared in Reference Production Example 4 and 8.21 g of di-tert-butyl dicarboxylate in 20 mL of tetrahydrofuran was added 195 mg of 4-dimethylpyridine at room temperature, followed by stirring at the same temperature for 1.5 hours. To the reaction mixture was added ethyl acetate. The organic layer was washed with 2 N hydrochloric acid and then an aqueous saturated sodium hydrogen carbonate solution, dried over anhydrous sodium sulfate, and then concentrated under reduced pressure. The residue was dissolved in 20 mL of methanol. To the solution were added 10 mL of water and 2.76 g of sodium carbonate at room temperature, followed by stirring at the same temperature for 2 hours. Water was added to the mixture, followed by extraction with ethyl acetate. The organic layer was dried over anhydrous sodium sulfate and then concentrated under reduced pressure to obtain 3.5 g of a compound represented by the following formula.

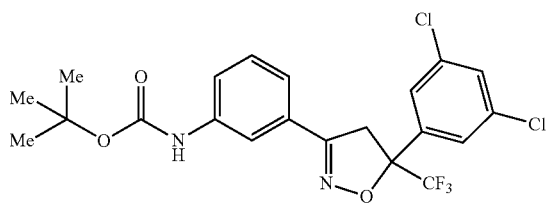 [SMILES: CC(C)(C)OC(=O)Nc1cccc(C2=NOC(c3cc(Cl)cc(Cl)c3)(C(F)(F)F)C2)c1]

¹H-NMR (CDCl₃) δ: 7.81 (1H, s), 7.51 (2H, s), 7.42-7.39 (2H, m), 7.35-7.31 (2H, m), 6.55 (1H, br s), 4.11 (1H, d, J=16.9 Hz), 3.70 (1H, d, J=16.9 Hz), 1.53 (9H, s).

Reference Production Example 6

To a solution of 3.50 g of the compound prepared in Reference Production Example 5 in 22 mL of tert-butyl methyl ether were added 23 mL of an aqueous 28% sodium hydroxide solution, 7 mL of ammonia water, 2.56 g of ammonium chloride and 100 mg of trioctylmethylammonium chloride. To the mixture was added dropwise 53 mL of an aqueous 5% sodium hypochlorite solution at room temperature over 20 minutes. After stirring at the same temperature for 12 hours, the organic layer was separated and the aqueous layer was extracted again with tert-butyl methyl ether. The organic layers were combined, dried over anhydrous sodium sulfate and then concentrated under reduced pressure. The residue was subjected to silica gel column chromatography to obtain 1.52 g of a compound represented by the following formula.

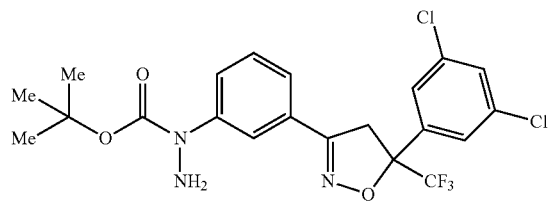

¹H-NMR (CDCl₃) δ: 7.87 (1H, s), 7.72-7.29 (6H, m), 4.42 (2H, br s), 4.09 (1H, d, J=17.2 Hz), 3.69 (1H, d, J=17.2 Hz), 1.53 (9H, s).

Reference Production Example 7

To a solution of 3.71 g of the compound prepared in Reference Production Example 4 and 1.34 g of methyl iodide in 20 mL of N,N-dimethylformamide was added 1.31 g of sodium carbonate at room temperature. The mixture was stirred at the same temperature for 12 hours. To the reaction mixture was added ethyl acetate, followed by washing with 2 N hydrochloric acid and then an aqueous saturated sodium hydrogen carbonate solution. The organic layer was dried over anhydrous sodium sulfate and then concentrated under reduced pressure to obtain 3.70 g of a compound represented by the following formula.

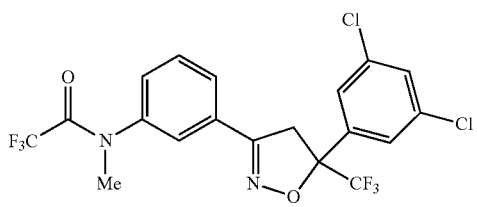 [SMILES: CN(C(=O)C(F)(F)F)c1cccc(C2=NOC(c3cc(Cl)cc(Cl)c3)(C(F)(F)F)C2)c1]

¹H-NMR (CDCl₃) δ: 7.69-7.35 (7H, m), 4.09 (1H, d, J=17.3 Hz), 3.71 (1H, d, J=17.3 Hz), 3.46-3.43 (3H, m).

Reference Production Example 8

To a solution of 3.52 g of the compound prepared in Reference Production Example 7 in 15 mL of methanol were added 2.00 g of sodium carbonate and 5 mL of water at room temperature. After stirring at the same temperature for 2 hours, ethyl acetate was added thereto and the aqueous layer was extracted with ethyl acetate. The organic layer was washed with 2% hydrochloric acid and then an aqueous saturated sodium hydrogen carbonate solution. The organic layer was dried over anhydrous sodium sulfate and then concentrated under reduced pressure to obtain 2.80 g of a compound represented by the following formula.

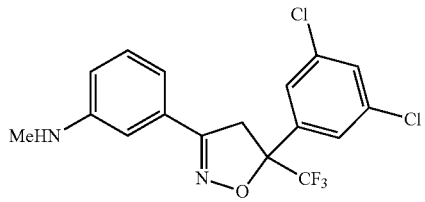 [SMILES: CNc1cccc(C2=NOC(c3cc(Cl)cc(Cl)c3)(C(F)(F)F)C2)c1]

¹H-NMR (CDCl₃) δ: 7.51 (2H, d, J=1.2 Hz), 7.41 (1H, t, J=1.8 Hz), 7.21 (1H, t, J=7.9 Hz), 6.95 (1H, t, J=2.0 Hz), 6.87 (1H, ddd, J=7.6, 1.5, 1.0 Hz), 6.69 (1H, ddd, J=8.3, 2.4, 0.7 Hz), 4.07 (1H, d, J=17.3 Hz), 3.85 (1H, br s), 3.67 (1H, d, J=17.3 Hz), 2.86 (3H, s).

Reference Production Example 9

To a solution of 2.6 g of the compound prepared in Reference Production Example 8 in 4 mL of tetrahydrofuran were added 1.5 mL of concentrated hydrochloric acid and 3.0 mL of water at room temperature. After stirring at room temperature for 15 minutes, to the mixture was added dropwise a solution of 581 mg of sodium nitrite in 5 mL of water at 0° C. After stirring at the same temperature for 1 hour, an aqueous saturated sodium hydrogen carbonate solution was added thereto and the aqueous layer was extracted with ethyl acetate. The organic layer was dried over anhydrous sodium sulfate and then concentrated under reduced pressure to obtain 2.78 g of a compound represented by the following formula.

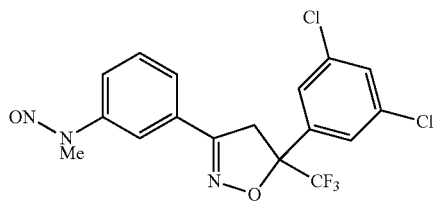

¹H-NMR (CDCl₃) δ: 7.89-7.88 (1H, m), 7.67-7.64 (2H, m), 7.56-7.53 (3H, m), 7.43-7.43 (1H, m), 4.14 (1H, d, J=17.4 Hz), 3.76 (1H, d, J=17.4 Hz), 3.47 (3H, s).

Reference Production Example 10

To a mixture of 1.00 g of the compound prepared in Reference Production Example 9, 2 mL of ethanol, 2 mL of water and 2 mL of acetic acid was added 695 mg of zinc at room temperature. After stirring at room temperature for 5 hours, the mixture was filtered. To the filtrate was added anhydrous sodium hydrogen carbonate, followed by extraction with chloroform. The organic layer was dried over anhydrous sodium sulfate and then concentrated under reduced pressure. The residue was subjected to silica gel column chromatography to obtain 1.1 g of a crude compound represented by the following formula.

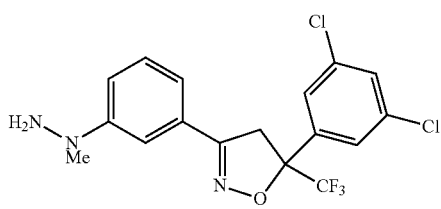

Reference Production Example 11

To a mixture of 3.00 g of 4-methyl-3-nitrobenzaldehyde, 1.64 g of hydroxylamine hydrochloride, 30 ml of ethanol and 15 ml of water was added 2.24 g of sodium acetate at room temperature, followed by stirring at room temperature for 1 hour. The reaction mixture was added to water, followed by extraction with ethyl acetate. The organic layer was dried over anhydrous sodium sulfate and then concentrated under reduced pressure to obtain 2.77 g of 5-hydroxyiminomethyl-2-methylnitrobenzene. 5-Hydroxyiminomethyl-2-methylnitrobenzene

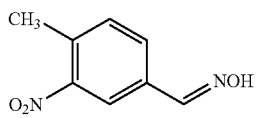

$^1$H-NMR (DMSO-$d_6$) δ: 11.53 (1H, s), 8.24 (1H, s), 8.17 (1H, d, J=1.7 Hz), 7.84 (1H, dd, J=8.0, 1.7 Hz), 7.54 (1H, d, J=8.0 Hz), 2.52 (3H, s).

Reference Production Example 12

A solution of 2.77 g of 5-hydroxyiminomethyl-2-methylnitrobenzene obtained in Reference Production Example 11 and 2.06 g of N-chlorosuccinimide in 30 ml of N,N-dimethylformamide was stirred at 50° C. for 1 hour. The reaction solution was cooled to room temperature, and thereto were added 3.71 g of 2-(3,5-dichlorophenyl)-3,3,3-trifluoro-1-propene and 1.56 g of triethylamine. The mixture was stirred at room temperature for 6 hours. To the reaction mixture was added water, followed by extraction with ethyl acetate. The organic layer was dried over anhydrous sodium sulfate and then concentrated under reduced pressure. The residue was subjected to silica gel column chromatography to obtain 4.99 g of a compound represented by the following formula.

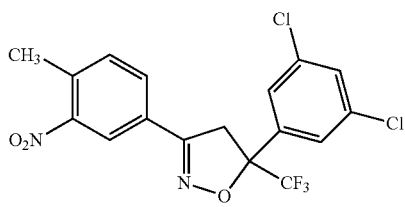

$^1$H-NMR (CDCl$_3$) δ: 8.16 (1H, d, J=1.9 Hz), 7.90 (1H, dd, J=8.1, 1.9 Hz), 7.51 (2H, d, J=1.2 Hz), 7.45-7.43 (2H, m), 4.11 (1H, d, J=17.1 Hz), 3.73 (1H, d, J=17.1 Hz), 2.66 (3H, s).

Reference Production Example 13

To 19 ml of an aqueous 2.5% acetic acid solution was added 1.89 g of iron powder (10 to 20 mesh). Thereto was added a suspension of 4.62 g of the compound prepared in Reference Production Example 12 in 29 ml of ethanol at 75° C., followed by stirring at same temperature for 15 minutes. Further 1.80 g of iron powder was added thereto at the same temperature, followed by stirring at the same temperature for 1 hour. The reaction mixture was cooled to room temperature, filtered and then washed with ethyl acetate. The filtrate was extracted by adding an aqueous saturated sodium hydrogen carbonate solution and ethyl acetate. The organic layer was dried over anhydrous sodium sulfate and then concentrated under reduced pressure. The residue was subjected to silica gel column chromatography to obtain 3.18 g of a compound represented by the following formula.

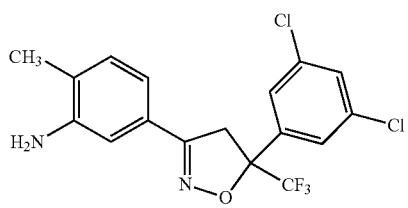 [SMILES: Cc1ccc(C2=NOC(c3cc(Cl)cc(Cl)c3)(C(F)(F)F)C2)cc1[N+](=O)[O-]]

$^1$H-NMR (CDCl$_3$) δ: 7.51 (2H, d, J=1.4 Hz), 7.41 (1H, t, J=1.8 Hz), 7.08 (1H, d, J=7.8 Hz), 7.05 (1H, d, J=1.8 Hz), 6.88 (1H, dd, J=7.8, 1.7 Hz), 4.04 (1H, d, J=17.1 Hz), 3.71 (2H, br s), 3.65 (1H, d, J=17.1 Hz), 2.19 (3H, s).

Reference Production Example 14

To 420 mg of the compound prepared in Reference Production Example 13 was added 2 mL of concentrated hydrochloric acid at room temperature. After stirring at the same temperature for 20 minutes, the solution was cooled to 0° C. and a solution of 82 mg of sodium nitrite in 0.5 mL of water was added dropwise thereto. After stirring at the same temperature for 10 minutes, to the reaction solution was added dropwise a solution of 451 mg of tin(II) chloride in 0.5 mL of concentrated hydrochloric acid. The reaction mixture was neutralized by addition of an aqueous saturated sodium hydrogen carbonate solution. The aqueous layer was extracted with ethyl acetate. The organic layer was dried over anhydrous sodium sulfate and then concentrated under reduced pressure to obtain 420 mg of a crude compound represented by the following formula.

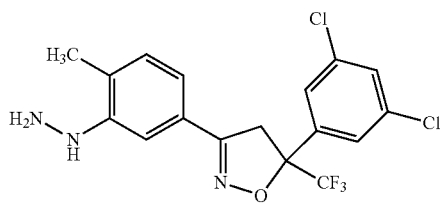 [SMILES: Cc1ccc(C2=NOC(c3cc(Cl)cc(Cl)c3)(C(F)(F)F)C2)cc1NN]

Reference Production Example 15

To a mixture of 20 ml of ethanol and 10 ml of water were added 2 g of 4-fluoro-3-nitrobenzaldehyde, 1.07 g of hydroxylamine hydrochloride and 1.45 g of sodium acetate. The mixture was stirred at room temperature for 6 hours. To the reaction mixture was added water, followed by extraction with ethyl acetate. The organic layer was dried over anhydrous sodium sulfate and then concentrated under reduced pressure to obtain 1.95 g of a compound represented by the following formula.

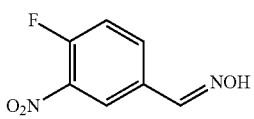

$^1$H-NMR (DMSO-D$_6$) δ: 11.63 (1H, s), 8.34 (1H, dd, J=7.2, 2.2 Hz), 8.28 (1H, s), 8.04-8.02 (1H, m), 7.65-7.62 (1H, m).

Reference Production Example 16

A solution of 1.95 of the compound obtained in Reference Production Example 15 and 1.42 g of N-chlorosuccinimide in 20 ml of dimethylformamide was stirred at 60° C. for 1 hour. The reaction mixed solution was cooled to room temperature, and thereto were added 2.55 g of 2-(3,5-dichlorophenyl)-3,3,3-trifluoro-1-propene and then 1.07 g of triethylamine, followed by stirring at the same temperature for 6 hours. To the reaction mixture was added water, followed by extraction with ethyl acetate. The organic layer was dried over anhydrous sodium sulfate and then concentrated under reduced pressure. The resultant residue was subjected to silica gel column chromatography to obtain 1.40 g of a compound represented by the following formula.

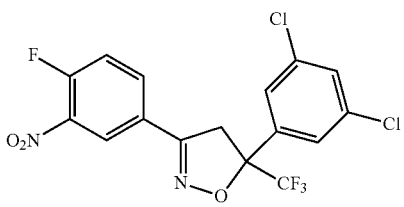 [SMILES: O=[N+]([O-])c1cc(C2=NOC(c3cc(Cl)cc(Cl)c3)(C(F)(F)F)C2)ccc1F]

$^1$H-NMR (CDCl$_3$) δ: 8.26 (1H, dd, J=6.9, 2.3 Hz), 8.08-8.05 (1H, m), 7.51 (2H, d, J=1.2 Hz), 7.45 (1H, t, J=1.9 Hz), 7.41 (1H, dd, J=10.1, 8.7 Hz), 4.11 (1H, d, J=17.4 Hz), 3.73 (1H, d, J=17.9 Hz).

Reference Production Example 17

To a solution of 0.2 g of acetic acid in 7 ml of water was added 1.85 g of iron powder at room temperature. To the mixture was added a suspension of 1.40 g of the compound obtained in Reference Production Example 16 in 15 ml of ethanol at 75° C., followed by stirring at 75° C. for 20 minutes. The reaction mixture was filtrated and the filtrate was concentrated under reduced pressure. The residue was subjected to silica gel column chromatography to obtain 806 mg of a compound represented by the following formula.

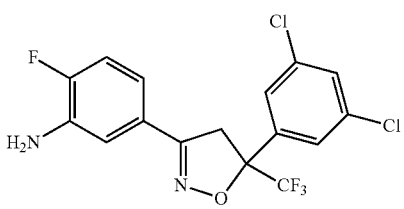

$^1$H-NMR (CDCl$_3$) δ: 7.50 (2H, d, J=1.4 Hz), 7.42 (1H, t, J=1.8 Hz), 7.18 (1H, dd, J=8.5, 2.2 Hz), 7.01 (1H, dd, J=10.6, 8.5 Hz), 6.90-6.87 (1H, m), 4.03 (1H, d, J=17.0 Hz), 3.85 (2H, br s), 3.64 (1H, d, J=17.0 Hz).

Reference Production Example 18

To a solution of 500 mg of the compound prepared in Reference Production Example 17 in 2 mL of 1,4-dioxane was added 4 mL of concentrated hydrochloric acid at room temperature. After stirring at the same temperature for 20 minutes, the solution was cooled to 0° C. and thereto was added dropwise a solution of 96 mg of sodium nitrite in 5 mL of water. After stirring at the same temperature for 15 minutes, to the reaction solution was added dropwise a solution of 528 mg of tin(II) chloride in 1 mL of concentrated hydrochloric acid. The reaction mixture was neutralized by addition of 2 N sodium hydroxide. The aqueous layer was extracted with ethyl acetate. The organic layer was dried over anhydrous sodium sulfate and then concentrated under reduced pressure to obtain 412 mg of a crude compound represented by the following formula.

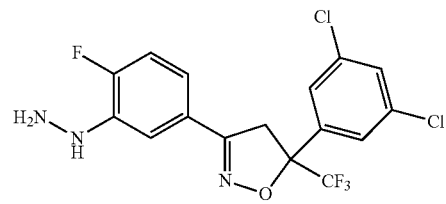

Reference Production Example 19

A solution of 2.92 g of 2-chloro-5-hydroxyiminomethylnitrobenzene and 1.94 g of N-chlorosuccinimide in 30 ml of dimethylformamide was stirred at 60° C. for 1 hour. After the solution cooled to room temperature, 3.50 g of 2-(3,5-dichlorophenyl)-3,3,3-trifluoro-1-propene and then 1.46 g of triethylamine were added thereto, followed by stirring for 6 hours. To the reaction mixture was added water, followed by extraction with ethyl acetate. The organic layer was dried over anhydrous sodium sulfate and then concentrated under reduced pressure. The residue was subjected to silica gel column chromatography to obtain 4.42 g of a compound represented by the following formula.

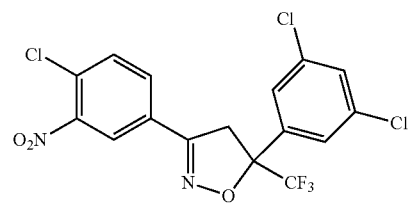 [SMILES: O=[N+]([O-])c1cc(C2=NOC(c3cc(Cl)cc(Cl)c3)(C(F)(F)F)C2)ccc1Cl]

$^1$H-NMR (CDCl$_3$) δ: 8.09 (1H, d, J=2.1 Hz), 7.89 (1H, dd, J=8.5, 2.1 Hz), 7.65 (1H, d, J=8.5 Hz), 7.50 (2H, d, J=1.6 Hz), 7.45 (1H, t, J=1.6 Hz), 4.09 (1H, d, J=17.3 Hz), 3.71 (1H, d, J=17.3 Hz).

Reference Production Example 20

To a mixture of 0.38 g of acetic acid, 15 ml of water and 30 ml of ethanol was added 3.46 g of iron powder at room temperature, and thereto was added 2.73 g of the compound obtained in Reference Production Example 19 at 75° C., followed by stirring at 75° C. for 50 minutes. The reaction mixture was filtered and the filtrate was concentrated under reduced pressure. The residue was subjected to silica gel column chromatography to obtain 1.65 g of a compound represented by the following formula.

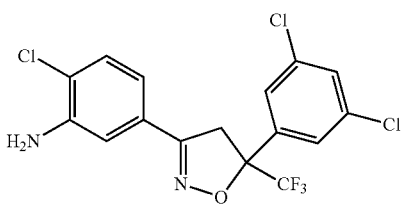

$^1$H-NMR (CDCl$_3$) δ: 7.49 (2H, d, J=1.7 Hz), 7.42 (1H, t, J=1.7 Hz), 7.29 (1H, d, J=8.4 Hz), 7.13 (1H, d, J=2.0 Hz), 6.89 (1H, dd, J=8.4, 2.0 Hz), 4.18 (2H, br s), 4.03 (1H, d, J=17.1 Hz), 3.64 (1H, d, J=16.4 Hz).

Reference Production Example 21

To a solution of 500 mg of the compound prepared in Reference Production Example 20 in 2 mL of 1,4-dioxane was added 6 mL of concentrated hydrochloric acid at room temperature. After stirring at the same temperature for 20 minutes, the solution was cooled to 0° C. and a solution of 93 mg of sodium nitrite in 3 mL of water was added dropwise thereto. After stirring at the same temperature for 15 minutes, to the reaction solution was added dropwise a solution of 507 mg of tin(II) chloride in 4 mL of concentrated hydrochloric acid. The reaction mixture was neutralized by addition of 2 N sodium hydroxide. The aqueous layer was extracted with t-butyl methyl ether. The organic layer was dried over anhydrous sodium sulfate and then concentrated under reduced pressure to obtain 510 mg of a crude compound represented by the following formula.

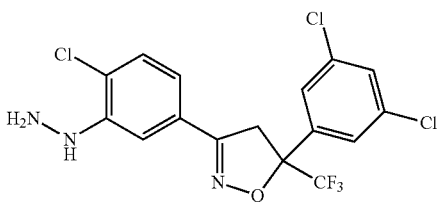

Reference Production Example 22

To a solution of 6.3 g of triphosgene in 50 mL of toluene was added dropwise a solution of 8.7 g of the compound obtained in Reference Production Example 20 in 50 mL of toluene and 10 mL of tetrahydrofuran. Further 50 mL of toluene was added to the reaction solution, followed by stirring at 80° C. for 1 hour. The reaction mixture was cooled to room temperature and then concentrated under reduced pressure, and 100 mL of tert-butanol was added thereto. To the solution was added 14.6 g of triethylamine at room temperature, followed by stirring at the same temperature for 16 hours. To the reaction mixture was added an aqueous saturated sodium hydrogen carbonate solution, followed by extraction with chloroform. The organic layer was dried over anhydrous sodium sulfate and then concentrated under reduced pressure. The residue was subjected to silica gel column chromatography to obtain 9.81 g of a compound represented by the following formula.

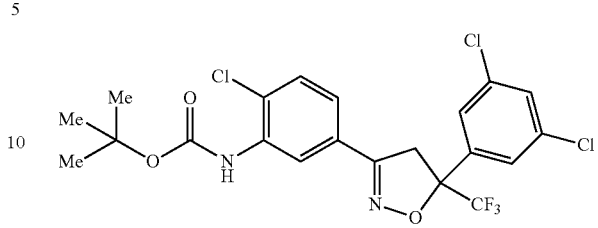

$^1$H-NMR (CDCl$_3$) δ: 8.39 (1H, d, J=2.1 Hz), 7.52 (2H, d, J=1.8 Hz), 7.47 (1H, dd, J=8.5, 2.1 Hz), 7.42 (1H, t, J=1.8 Hz), 7.39 (1H, d, J=8.5 Hz), 7.09 (1H, br s), 4.11 (1H, d, J=17.3 Hz), 3.70 (1H, d, J=17.3 Hz), 1.55 (9H, s).

Reference Production Example 23

To a suspension of 760 mg of sodium hydride (60% in oil) in 200 mL of tetrahydrofuran was added dropwise a solution of 8.80 g of the compound prepared in Reference Production Example 22 in 50 mL of tetrahydrofuran at room temperature. After the mixture was stirred at the same temperature for 20 minutes, 6.0 g of O-(diphenylphosphoryl)hydroxylamine was added thereto at room temperature. After the mixture was stirred at the same temperature for 15 hours, water and ethyl acetate were added thereto and the aqueous layer was extracted with ethyl acetate. The organic layer was dried over anhydrous sodium sulfate and then concentrated under reduced pressure. The residue was subjected to silica gel column chromatography to obtain 6.58 g of a compound represented by the following formula.

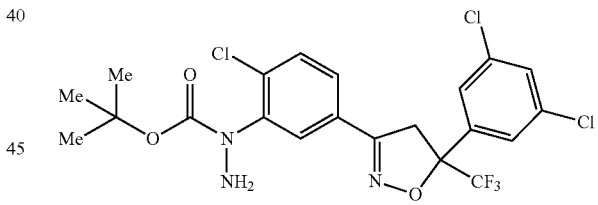

$^1$H-NMR (CDCl$_3$) δ: 7.55-7.44 (6H, m), 4.07 (1H, d, J=17.1 Hz), 3.68 (1H, d, J=17.1 Hz), 1.41 (9H, br s).

Reference Production Example 24

To a solution of 3.04 g of the compound obtained in Reference Production Example 20 and 772 mg of triethylamine in 20 mL of tetrahydrofuran was added dropwise 1.47 g of trifluoroacetic anhydride at 0° C. After stirring at the same temperature for 30 minutes, the reaction mixture was diluted with tert-butyl methyl ether. To the reaction mixture was added ethyl acetate. The organic layer was washed with 2 N hydrochloric acid and then an aqueous saturated sodium hydrogen carbonate solution, dried over anhydrous sodium sulfate and then concentrated under reduced pressure to obtain 3.63 g of a compound represented by the following formula.

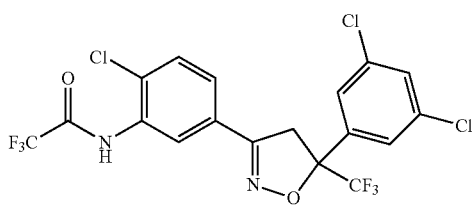

¹H-NMR (CDCl₃) δ: 8.53 (1H, d, J=2.2 Hz), 8.48 (1H, br s), 7.67 (1H, dd, J=8.5, 2.0 Hz), 7.52 (1H, d, J=8.5 Hz), 7.50 (2H, s), 7.43-7.42 (1H, m), 4.09 (1H, d, J=17.3 Hz), 3.71 (1H, d, J=17.3 Hz).

Reference Production Example 25

To a suspension of sodium hydride (60% in oil) in 15 mL of N,N-dimethylformamide was added dropwise a solution of 3.6 g of the compound obtained in Reference Production Example 24 in 15 mL of N,N-dimethylformamide at room temperature. After the mixture was stirred at the same temperature for 20 minutes, 1.52 g of methyl iodide was added thereto, followed by stirring for 1 hour. To the reaction mixture was added 2 N hydrochloric acid, followed by extraction with tert-butyl methyl ether. The organic layer was dried over anhydrous sodium sulfate and then concentrated under reduced pressure to obtain 3.73 g of a compound represented by the following formula.

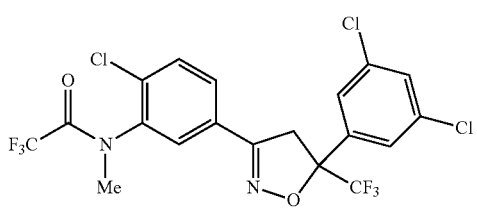 [SMILES: CN(C(=O)C(F)(F)F)c1cc(C2=NOC(c3cc(Cl)cc(Cl)c3)(C(F)(F)F)C2)ccc1Cl]

¹H-NMR (CDCl₃) δ: 7.70-7.40 (6H, m), 4.06 (1H, dd, J=17.2, 13.0 Hz), 3.73-3.64 (1H, m), 3.33-3.32 (3H, m).

Reference Production Example 26

To a solution of 3.6 g of the compound obtained in Reference Production Example 25 in 20 mL of methanol was added 1.97 g of potassium carbonate at room temperature, followed by stirring at the same temperature for 3 hours. A precipitate was filtered. To the filtrate was added water, followed by extraction with t-butyl methyl ether. The organic layer was dried over anhydrous sodium sulfate and then concentrated under reduced pressure to obtain 2.20 g of a compound represented by the following formula.

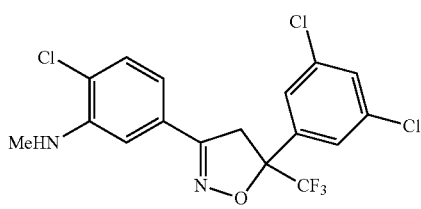 [SMILES: CNc1cc(C2=NOC(c3cc(Cl)cc(Cl)c3)(C(F)(F)F)C2)ccc1Cl]

¹H-NMR (CDCl₃) δ: 7.51 (2H, d, J=1.8 Hz), 7.42 (1H, t, J=1.8 Hz), 7.28 (1H, d, J=8.0 Hz), 6.99 (1H, d, J=2.0 Hz), 6.78 (1H, dd, J=8.0, 2.0 Hz), 4.48 (1H, d, J=5.1 Hz), 4.07 (1H, d, J=17.2 Hz), 3.67 (1H, d, J=17.2 Hz), 2.94 (3H, d, J=5.1 Hz).

Reference Production Example 27

To a solution of 2.55 g of the compound prepared in Reference Production Example 26 in 4 mL of tetrahydrofuran were added 4.5 mL of concentrated hydrochloric acid and then 5.0 mL of water. After stirring at room temperature for 10 minutes, the mixture was cooled to 0° C. and a solution of 539 mg of sodium nitrite in 5 mL of water was added dropwise thereto. The mixture was stirred at the same temperature for 1 hour, neutralized by addition of an aqueous saturated sodium hydrogen carbonate solution and then extracted with ethyl acetate. The organic layer was dried over anhydrous sodium sulfate and then concentrated under reduced pressure to obtain 2.69 g of a compound represented by the following formula.

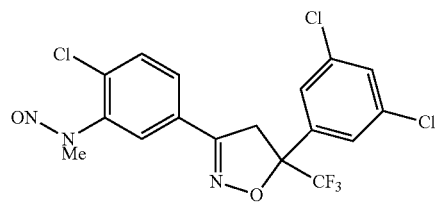

¹H-NMR (CDCl₃) δ: 7.84-7.31 (6H, m), 4.09 (1H, d, J=17.3 Hz), 3.71 (1H, d, J=17.3 Hz), 3.41 (3H, s).

Reference Production Example 28

To a solution of 2.61 g of the compound prepared, in Reference Production Example 27 in 4 mL of tetrahydrofuran were added 8 mL of ethanol, 8 mL of water and 8 mL of acetic acid at room temperature. Then, 695 mg of zinc was added to the mixture at room temperature. The mixture was stirred at room temperature for 3 hours and then filtered. To the filtrate was added anhydrous sodium hydrogen carbonate, followed by extraction with ethyl acetate. The organic layer was dried over anhydrous sodium sulfate and then concentrated under reduced pressure. The residue was subjected to silica gel column chromatography to obtain 764 mg of a compound represented by the following formula.

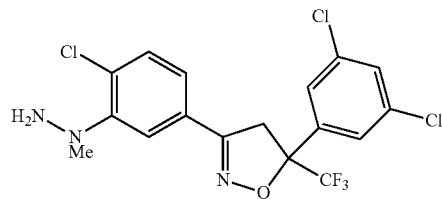

¹H-NMR (CDCl₃) δ: 7.68-7.67 (1H, m), 7.51 (2H, s), 7.42-7.40 (2H, m), 7.23-7.20 (1H, m), 4.08 (1H, d, J=17.2 Hz), 3.85 (2H, br s), 3.69 (1H, d, J=17.2 Hz), 3.06 (3H, s).

Reference Production Example 29

A solution of 4.30 g of 2-ethyl-5-hydroxyiminomethylnitrobenzene and 2.97 g of N-chlorosuccinimide in 40 ml of dimethylformamide was stirred at 60° C. for 1 hour. The reaction solution was cooled to room temperature. Thereto were added 3.5 g of 2-(3,5-dichlorophenyl)-3,3,3-trifluoro-1-propene and then 1.7 g of triethylamine, followed by stirring for 6 hours. To the reaction mixture was added water, followed by extraction with ethyl acetate. The organic layer was dried over anhydrous sodium sulfate and then concentrated under reduced pressure. The residue was subjected to silica gel column chromatography to obtain 5.74 g of a compound represented by the following formula.

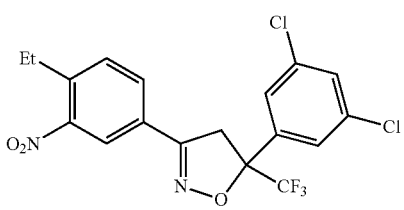

$^1$H-NMR (CDCl$_3$) δ: 8.07 (1H, d, J=1.9 Hz), 7.91 (1H, dd, J=8.0, 1.9 Hz), 7.51 (2H, d, J=1.6 Hz), 7.46 (1H, d, J=8.0 Hz), 7.44 (1H, t, J=1.6 Hz), 4.10 (1H, d, J=17.3 Hz), 3.72 (1H, d, J=17.3 Hz), 2.96 (2H, q, J=7.5 Hz), 1.30 (3H, t, J=7.5 Hz).

Reference Production Example 30

To a mixture of 0.5 ml of acetic acid, 22 ml of water and 34 ml of ethanol was added 4.33 g of iron powder at room temperature. To the mixture was added 5.60 g of the compound obtained in Reference Production Example 29 at 75° C., followed by stirring at the same temperature for 3 hours. The reaction mixture was cooled to room temperature, filtered and then washed with ethyl acetate. To the filtrate was added an aqueous saturated sodium hydrogen carbonate solution, followed by extraction with ethyl acetate. The organic layer was dried over anhydrous sodium sulfate and then concentrated under reduced pressure to obtain 5.20 g of a compound represented by the following formula.

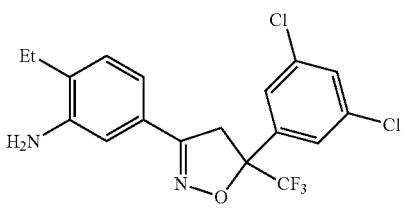 [SMILES: CCc1ccc(C2=NOC(c3cc(Cl)cc(Cl)c3)(C(F)(F)F)C2)cc1[N+](=O)[O-]]

$^1$H-NMR (CDCl$_3$) δ: 7.51 (2H, d, J=1.7 Hz), 7.41 (1H, t, J=1.7 Hz), 7.10 (1H, d, J=7.8 Hz), 7.04 (1H, d, J=1.7 Hz), 6.93 (1H, dd, J=7.8, 1.7 Hz), 4.05 (1H, d, J=17.1 Hz), 3.74 (2H, br s), 3.65 (1H, d, J=17.1 Hz), 2.52 (2H, q, J=7.5 Hz), 1.25 (3H, t, J=7.5 Hz).

Reference Production Example 31

To a solution of 1.00 g of the compound prepared in Reference Production Example 30 in 2 ml of 1,4-dioxane was added 4 mL of concentrated hydrochloric acid at room temperature. The mixture was stirred at the same temperature for 20 minutes and then cooled to 0° C. To the solution, a solution of 188 mg of sodium nitrite in 1 mL of water was added dropwise. After stirring at the same temperature for 15 minute, to the reaction solution was added dropwise a solution of 1.03 g of tin(II) chloride in 2 mL of concentrated hydrochloric acid. The reaction mixture was neutralized by addition of 2 N sodium hydroxide. The aqueous layer was extracted with chloroform. The organic layer was dried over anhydrous sodium sulfate and then concentrated under reduced pressure to obtain 1.31 g of a crude compound represented by the following formula.

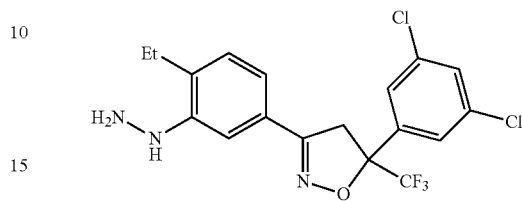

Reference Production Example 32

A solution of 2.0 g of the compound prepared in Reference Production Example 20 in 10 ml of acetic anhydride was stirred at room temperature for 0.5 hours. The reaction mixture was concentrated under reduced pressure. The concentrate was dissolved in ethyl acetate, and then washed with an aqueous saturated sodium hydrogen carbonate solution and then an aqueous saturated sodium chloride solution. The organic layer was dried over anhydrous sodium sulfate and then concentrated under reduced pressure to obtain 3.0 g of a crude compound represented by the following formula.

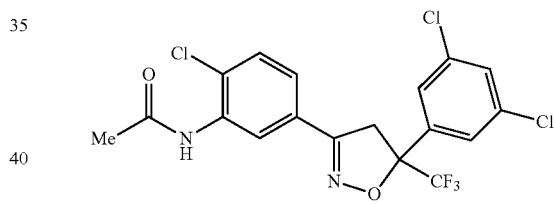

$^1$H-NMR (CDCl$_3$) δ: 8.59 (1H, br s), 7.67 (1H, br s), 7.57 (1H, dd, J=8.4, 2.1 Hz), 7.50 (2H, d, J=1.2 Hz), 7.43-7.42 (2H, m), 4.09 (1H, d, J=17.4 Hz), 3.70 (1H, d, J=17.4 Hz), 2.28 (3H, s).

Reference Production Example 33

To a solution of 2.2 g of the compound prepared in Reference Production Example 32 in 30 ml of tert-butylmethyl ether were added 14 mL of an aqueous 28% sodium hydroxide solution, 4.5 mL of ammonia water, 1.56 g of ammonium chloride and 274 mg of trioctylmethylammonium chloride. To the mixture was added dropwise 32 mL of an aqueous 5% sodium hypochlorite solution at room temperature over 20 minutes. After stirring at the same temperature for 2 hours, the organic layer was separated and the aqueous layer was extracted again with tert-butyl methyl ether. The organic layers were combined, dried over anhydrous sodium sulfate and then concentrated under reduced pressure. The residue was subjected to silica gel column chromatography to obtain 2.0 g of a compound represented by the following formula.

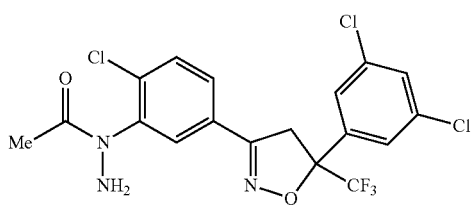 [SMILES: CC(=O)N(N)c1cc(C2=NOC(c3cc(Cl)cc(Cl)c3)(C(F)(F)F)C2)ccc1Cl]

Melting point: 92° C.

Reference Production Example 34

To a solution of 2.0 g of the compound prepared in Reference Production Example 20 in 5 ml of pyridine was added 1.4 g of benzoyl chloride at room temperature. After stirring at the same temperature for 0.5 hours, to the reaction mixture was added ethyl acetate, followed by washing with 3% hydrochloric acid. The organic layers were combined, dried over anhydrous sodium sulfate and then concentrated under reduced pressure to obtain 2.4 g of a crude compound represented by the following formula.

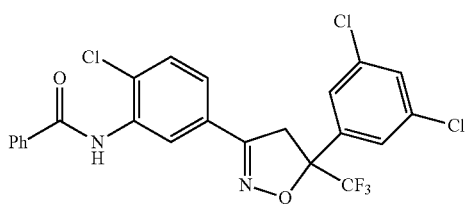 [SMILES: O=C(Nc1cc(C2=NOC(c3cc(Cl)cc(Cl)c3)(C(F)(F)F)C2)ccc1Cl)c1ccccc1]

$^1$H-NMR (CDCl$_3$) δ: 7.69-7.44 (1H, m), 7.68 (1H, dd, J=4.1, 2.0 Hz), 7.63 (1H, dd, J=5.7, 2.1 Hz), 7.58 (1H, d, J=7.8 Hz), 7.49 (2H, d, J=7.6 Hz), 7.44 (1H, t, J=2.0 Hz), 4.74 (2H, s), 4.37 (0H, s), 4.07 (1H, dd, J=17.2, 6.7 Hz), 2.42 (1H, s), 1.92 (2H, d, J=2.9 Hz).

Reference Production Example 35

To a solution of 2.4 g of the compound prepared in Reference Production Example 34 in 20 ml of tetrahydrofuran were added 14 mL of an aqueous 8% sodium hydroxide solution, 4.5 mL of ammonia water, 2.56 g of ammonium chloride and 274 mg of trioctylmethylammonium chloride. To the mixture was added dropwise 48 mL of an aqueous 5% sodium hypochlorite solution at room temperature over 1 hour. After stirring at the same temperature for 2 hours, the organic layer was separated and the aqueous layer was extracted again with tert-butyl methyl ether. The organic layers were combined, dried over anhydrous sodium sulfate and then concentrated under reduced pressure. The residue was subjected to silica gel column chromatography to obtain 1.8 g of a compound represented by the following formula.

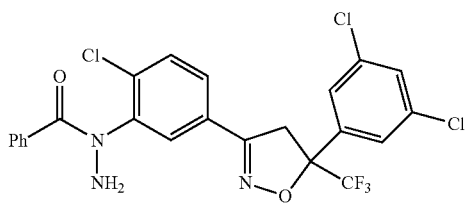 [SMILES: NN(C(=O)c1ccccc1)c1cc(C2=NOC(c3cc(Cl)cc(Cl)c3)(C(F)(F)F)C2)ccc1Cl]

Melting point: 87° C.

Specific examples of the present compound are shown below.

A compound represented by the formula (1-1):

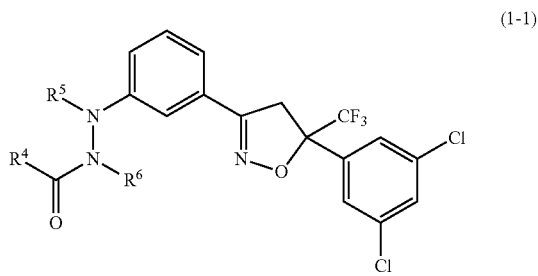

(1-1)

wherein R$^4$, R$^5$ and R$^6$ represent any one of combinations shown below.

A compound represented by the formula (1-2):

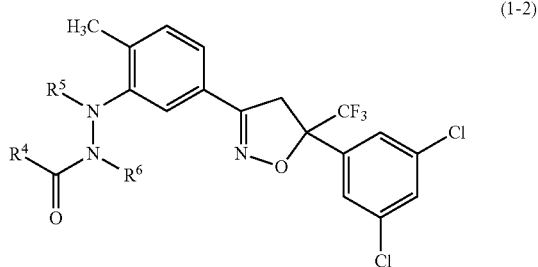

(1-2)

wherein R$^4$, R$^5$ and R$^6$ represent any one of combinations shown below.

A compound represented by the formula (1-3):

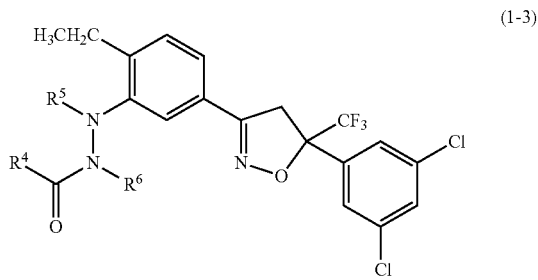

(1-3)

wherein R$^4$, R$^5$ and R$^6$ represent any one of combinations shown below.

A compound represented by the formula (1-4):

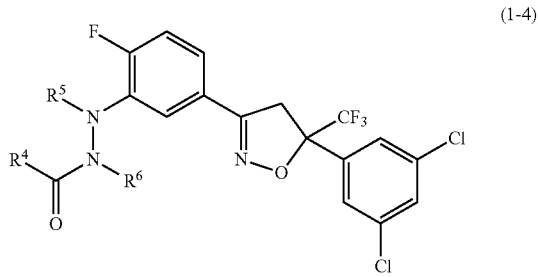

(1-4)

A compound represented by the formula (1-5):

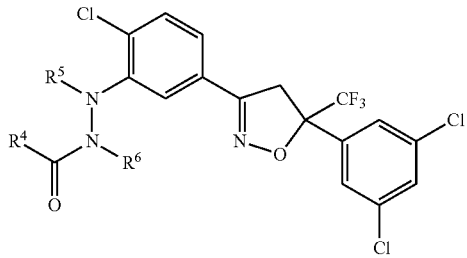

(1-5)

wherein $R^4$, $R^5$ and $R^6$ represent any one of combinations shown below.

A compound represented by the formula (1-6):

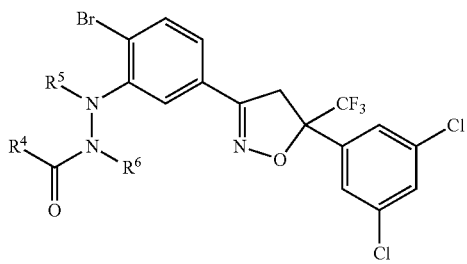

(1-6)

wherein $R^4$, $R^5$ and $R^6$ represent any one of combinations shown below.

A compound represented by the formula (1-7):

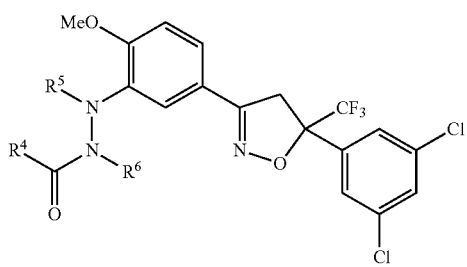

(1-7)

wherein $R^4$, $R^5$ and $R^6$ represent any one of combinations shown below.

A compound represented by the formula (1-8):

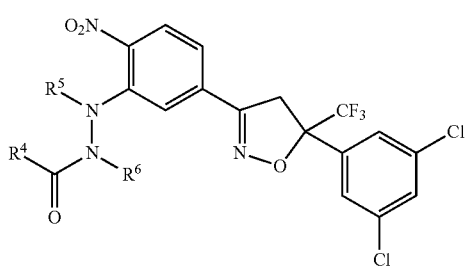

(1-8)

wherein $R^4$, $R^5$ and $R^6$ represent any one of combinations shown below.

A compound represented by the formula (1-9):

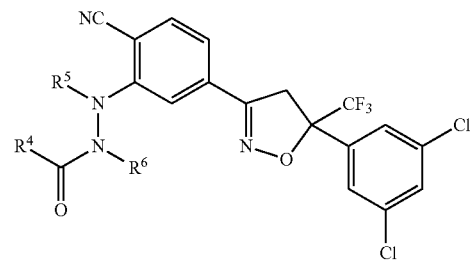

(1-9)

wherein $R^4$, $R^5$ and $R^6$ represent any one of combinations shown below.

A compound represented by the formula (1-10):

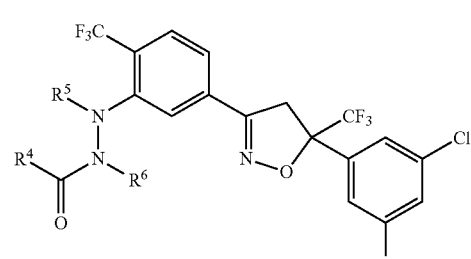

(1-10)

wherein $R^4$, $R^5$ and $R^6$ represent any one of combinations shown below.

A compound represented by the formula (1-11):

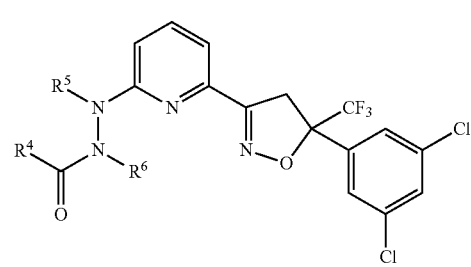

(1-11)

wherein $R^4$, $R^5$ and $R^6$ represent any one of combinations shown below.

A compound represented by the formula (1-12):

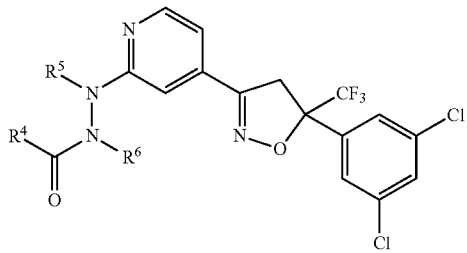

(1-12)

wherein R⁴; R⁵ and R⁶ represent any one of combinations shown below.

A compound represented by the formula (1-13):

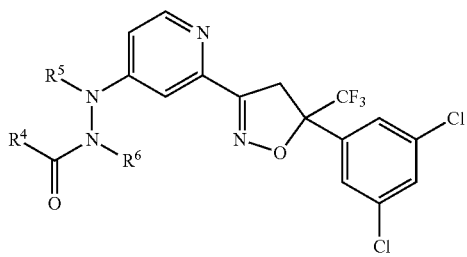

(1-13)

wherein R⁴, R⁵ and R⁶ represent any one of combinations shown below.

A compound represented by the formula (1-14):

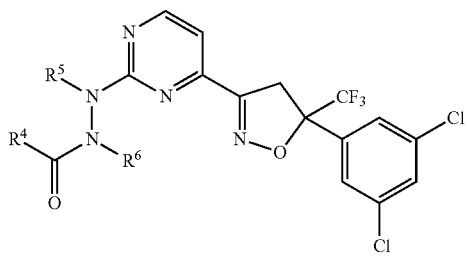

(1-14)

wherein R⁴, R⁵ and R⁶ represent any one of combinations shown below.

A compound represented by the formula (1-15):

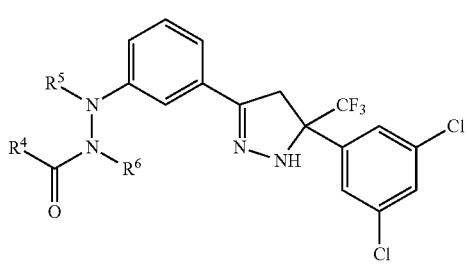

(1-15)

wherein R⁴, R⁵ and R⁶ represent any one of combinations shown below.

A compound represented by the formula (1-16):

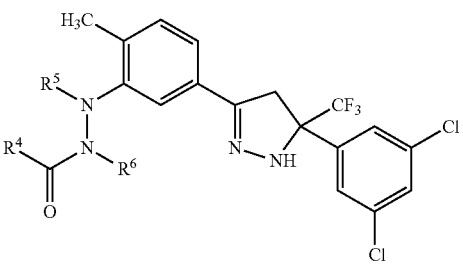

(1-16)

wherein R⁴, R⁵ and R⁶ represent any one of combinations shown below.

A compound represented by the formula (1-17):

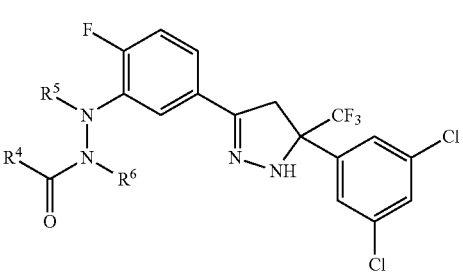

(1-17)

wherein R⁴, R⁵ and R⁶ represent any one of combinations shown below.

A compound represented by the formula (1-18):

(1-18)

wherein R⁴, R⁵ and R⁶ represent any one of combinations shown below.

A compound represented by the formula (1-19):

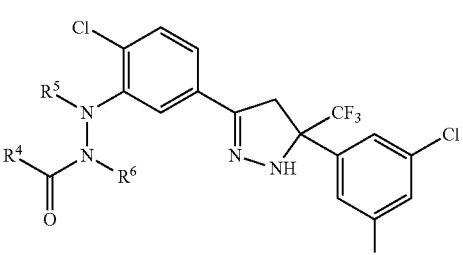

(1-19)

wherein R⁴, R⁵ and R⁶ represent any one of combinations shown below.

A compound represented by the formula (1-20):

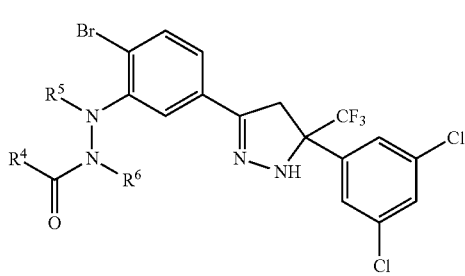

(1-20)

wherein $R^4$, $R^5$ and $R^6$ represent any one of combinations shown below.

A compound represented by the formula (1-21):

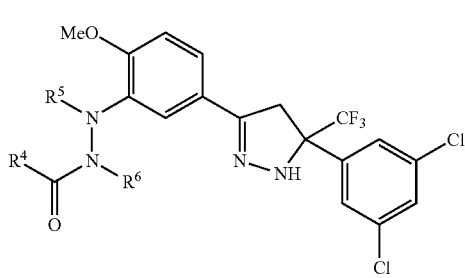

(1-21)

wherein $R^4$, $R^5$ and $R^6$ represent any one of combinations shown below.

A compound represented by the formula (1-22):

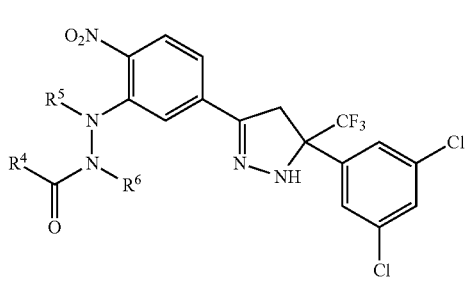

(1-22)

wherein $R^4$, $R^5$ and $R^6$ represent any one of combinations shown below.

A compound represented by the formula (1-23):

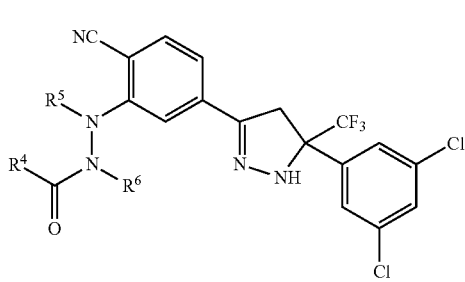

(1-23)

wherein $R^4$, $R^5$ and $R^6$ represent any one of combinations shown below.

A compound represented by the formula (1-24):

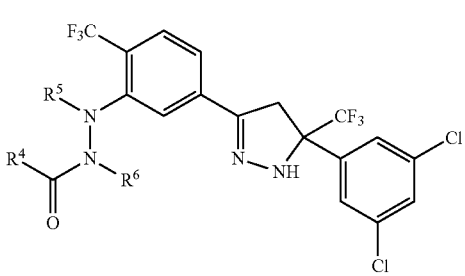

(1-24)

wherein $R^4$, $R^5$ and $R^6$ represent any one of combinations shown below.

A compound represented by the formula (1-25):

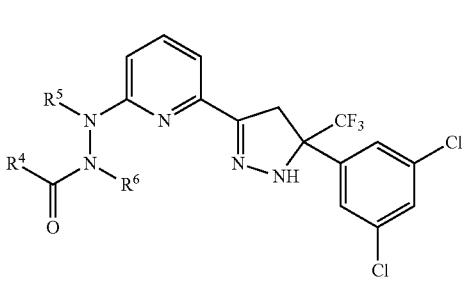

(1-25)

wherein $R^4$, $R^5$ and $R^6$ represent any one of combinations shown below.

A compound represented by the formula (1-26):

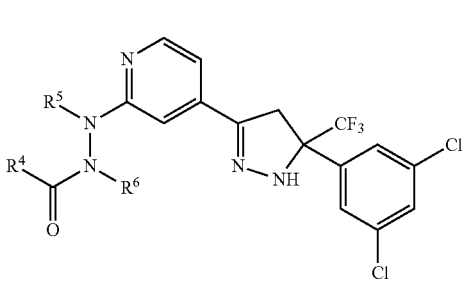

(1-26)

wherein $R^4$, $R^5$ and $R^6$ represent any one of combinations shown below.

A compound represented by the formula (1-27):

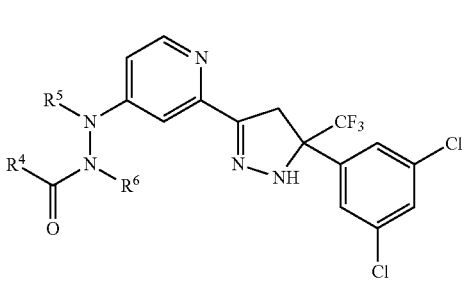

(1-27)

wherein $R^4$, $R^5$ and $R^6$ represent any one of combinations shown below.

A compound represented by the formula (1-28):

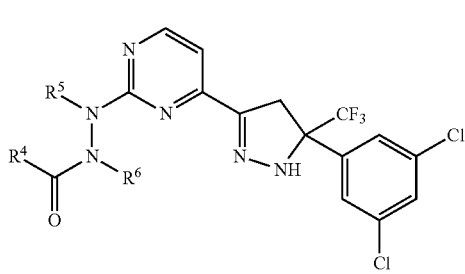

(1-28)

wherein R⁴, R⁵ and R⁶ represent any one of combinations shown below.

A compound represented by the formula (1-29):

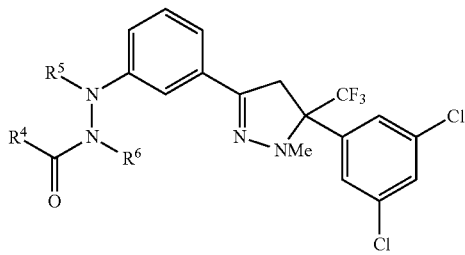

(1-29)

wherein R⁴, R⁵ and R⁶ represent any one of combinations shown below.

A compound represented by the formula (1-30):

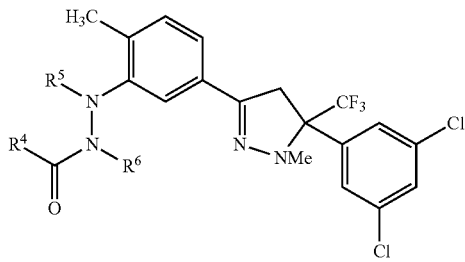

(1-30)

wherein R⁴, R⁵ and R⁶ represent any one of combinations shown below.

A compound represented by the formula (1-31):

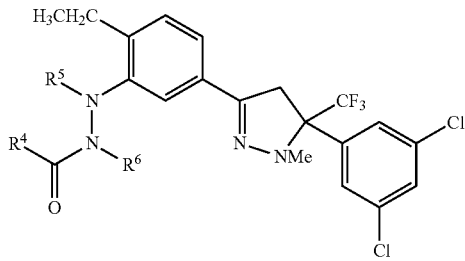

(1-31)

wherein R⁴, R⁵ and R⁶ represent any one of combinations shown below.

A compound represented by the formula (1-32):

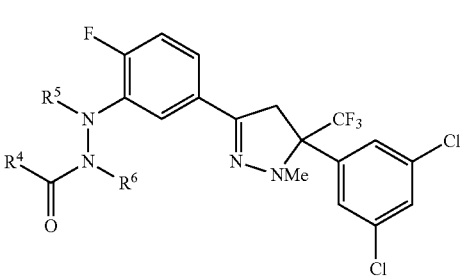

(1-32)

wherein R⁴, R⁵ and R⁶ represent any one of combinations shown below.

A compound represented by the formula (1-33):

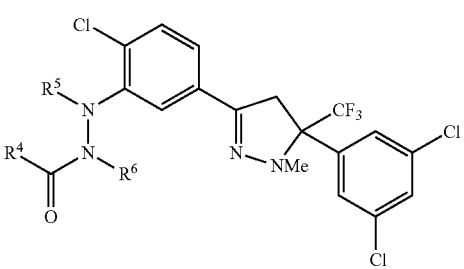

(1-33)

wherein R⁴, R⁵ and R⁶ represent any one of combinations shown below.

A compound represented by the formula (1-34):

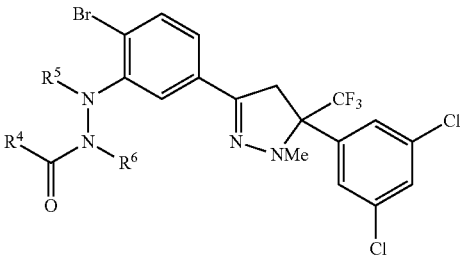

(1-34)

wherein R⁴, R⁵ and R⁶ represent any one of combinations shown below.

A compound represented by the formula (1-35):

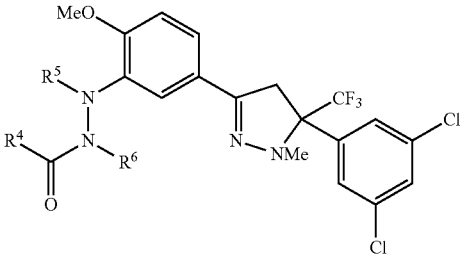

(1-35)

wherein R⁴, R⁵ and R⁶ represent any one of combinations shown below.

A compound represented by the formula (1-36):

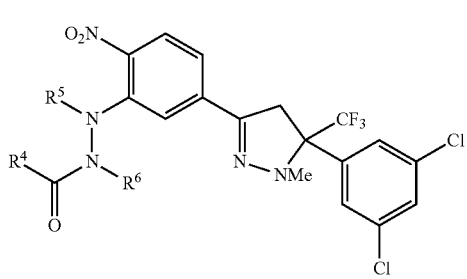

(1-36)

wherein R⁴, R⁵ and R⁶ represent any one of combinations shown below.

A compound represented by the formula (1-37):

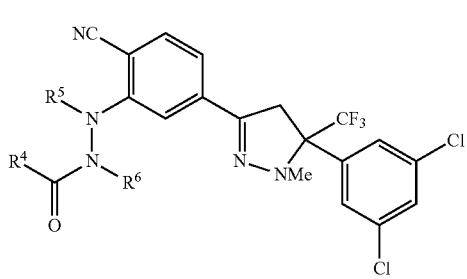

(1-37)

wherein R⁴, R⁵ and R⁶ represent any one of combinations shown below.

A compound represented by the formula (1-38):

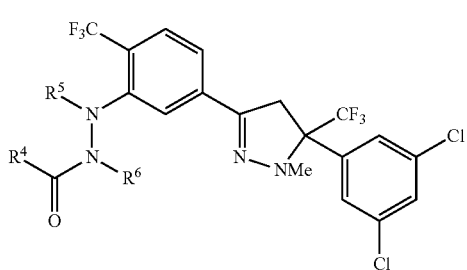

(1-38)

wherein R⁴, R⁵ and R⁶ represent any one of combinations shown below.

A compound represented by the formula (1-39):

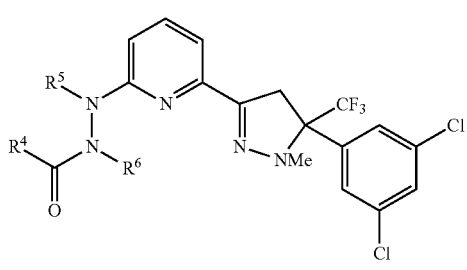

(1-39)

wherein R⁴, R⁵ and R⁶ represent any one of combinations shown below.

A compound represented by the formula (1-40):

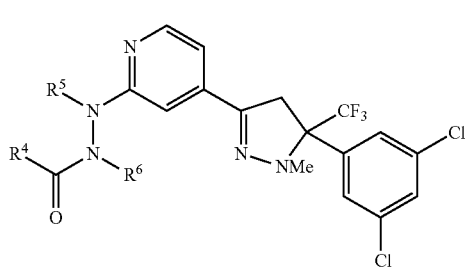

(1-40)

wherein R⁴, R⁵ and R⁶ represent any one of combinations shown below.

A compound represented by the formula (1-41):

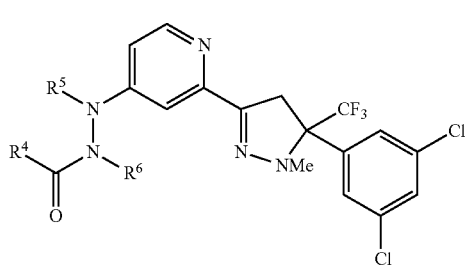

(1-41)

wherein R⁴, R⁵ and R⁶ represent any one of combinations shown below.

A compound represented by the formula (1-42):

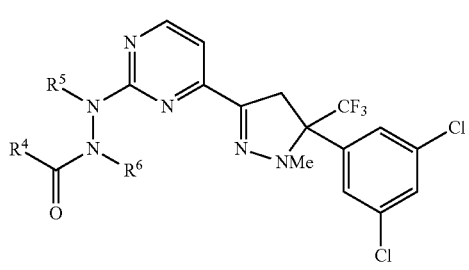

(1-42)

wherein R⁴, R⁵ and R⁶ represent any one of combinations shown below.

A compound represented by the formula (1-43):

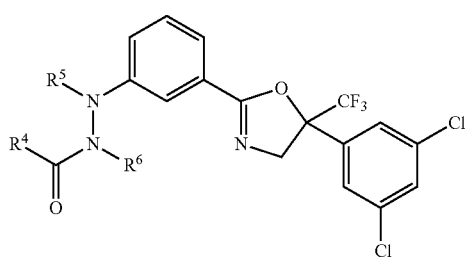

(1-43)

wherein R⁴, R⁵ and R⁶ represent any one of combinations shown below.

A compound represented by the formula (1-44):

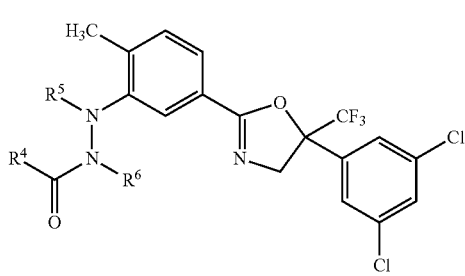

(1-44)

wherein $R^4$, $R^5$ and $R^6$ represent any one of combinations shown below.

A compound represented by the formula (1-45):

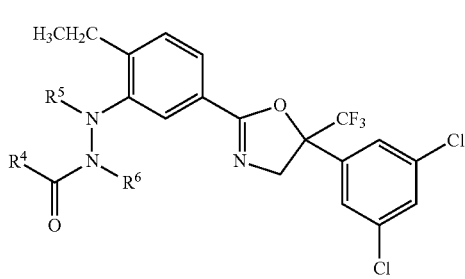

(1-45)

wherein $R^4$, $R^5$ and $R^6$ represent any one of combinations shown below.

A compound represented by the formula (1-46):

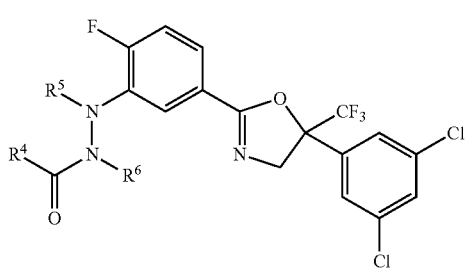

(1-46)

wherein $R^4$, $R^5$ and $R^6$ represent any one of combinations shown below.

A compound represented by the formula (1-47):

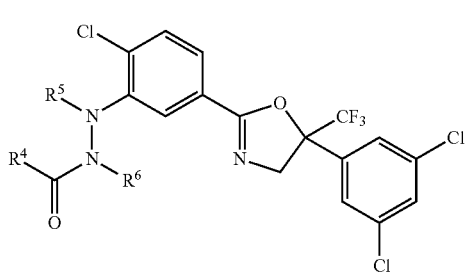

(1-47)

wherein $R^4$, $R^5$ and $R^6$ represent any one of combinations shown below.

A compound represented by the formula (1-48):

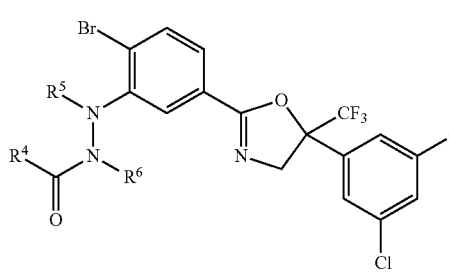

(1-48)

wherein $R^4$, $R^5$ and $R^6$ represent any one of combinations shown below.

A compound represented by the formula (1-49):

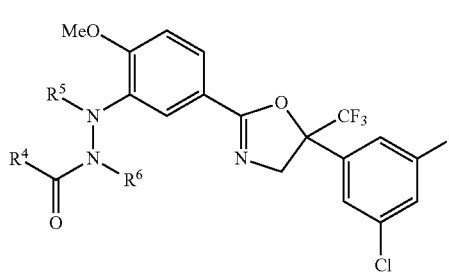

(1-49)

wherein $R^4$, $R^5$ and $R^6$ represent any one of combinations shown below.

A compound represented by the formula (1-50):

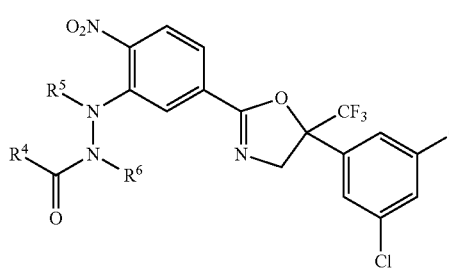

(1-50)

wherein $R^4$, $R^5$ and $R^6$ represent any one of combinations shown below.

A compound represented by the formula (1-51):

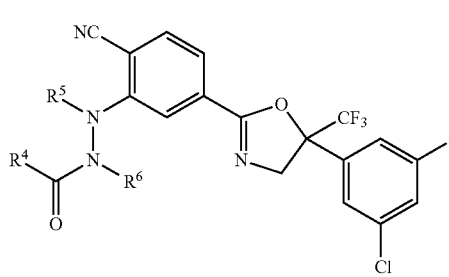

(1-51)

wherein $R^4$, $R^5$ and $R^6$ represent any one of combinations shown below.

A compound represented by the formula (1-52):

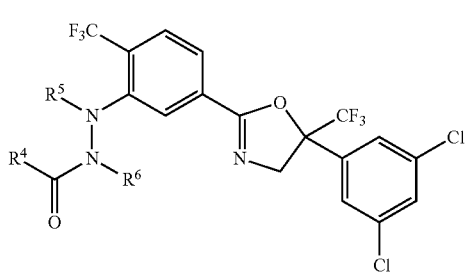
(1-52)

wherein R⁴, R⁵ and R⁶ represent any one of combinations shown below.

A compound represented by the formula (1-53):

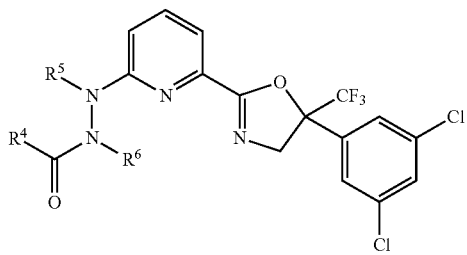
(1-53)

wherein R⁴, R⁵ and R⁶ represent any one of combinations shown below.

A compound represented by the formula (1-54):

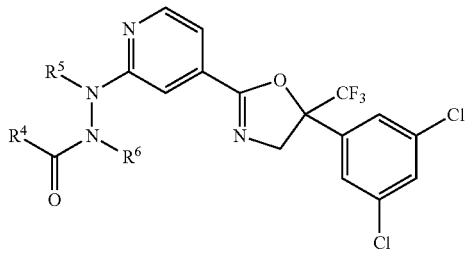
(1-54)

wherein R⁴, R⁵ and R⁶ represent any one of combinations shown below.

A compound represented by the formula (1-55):

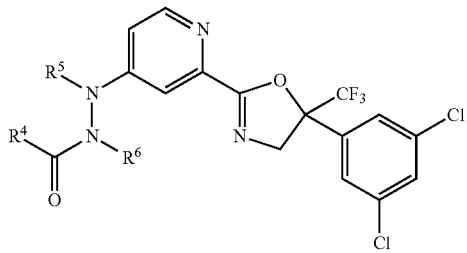
(1-55)

wherein R⁴, R⁵ and R⁶ represent any one of combinations shown below.

A compound represented by the formula (1-56):

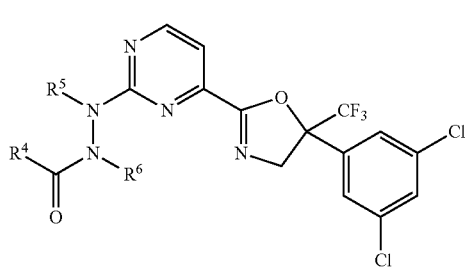
(1-56)

wherein R⁴, R⁵ and R⁶ represent any one of combinations shown below.

A compound represented by the formula (1-57):

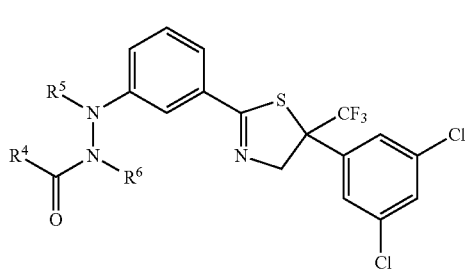
(1-57)

wherein R⁴, R⁵ and R⁶ represent any one of combinations shown below.

A compound represented by the formula (1-58):

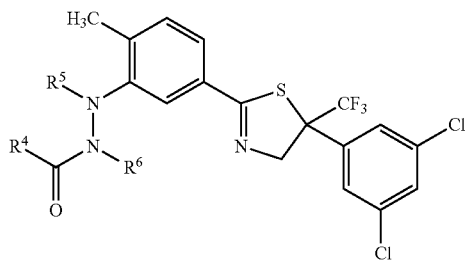
(1-58)

wherein R⁴, R⁵ and R⁶ represent any one of combinations shown below.

A compound represented by the formula (1-59):

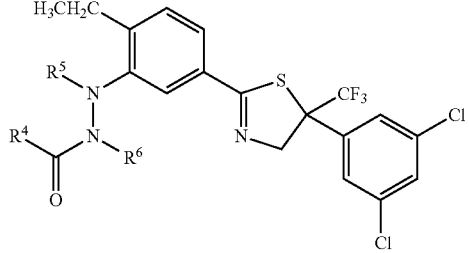
(1-59)

wherein R⁴, R⁵ and R⁶ represent any one of combinations shown below.

A compound represented by the formula (1-60):

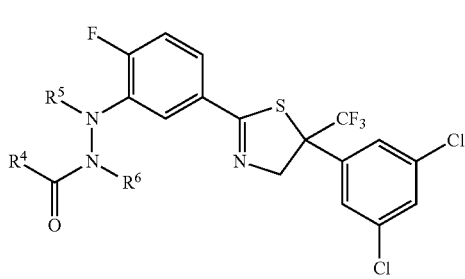

(1-60)

wherein R⁴, R⁵ and R⁶ represent any one of combinations shown below.

A compound represented by the formula (1-61):

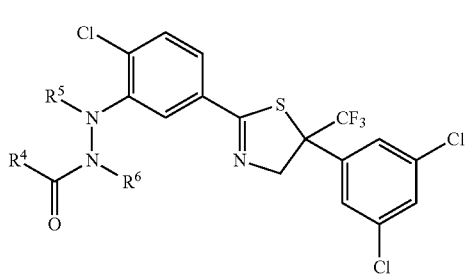

(1-61)

wherein R⁴, R⁵ and R⁶ represent any one of combinations shown below.

A compound represented by the formula (1-62):

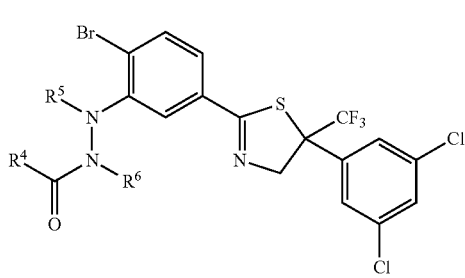

(1-62)

wherein R⁴, R⁵ and R⁶ represent any one of combinations shown below.

A compound represented by the formula (1-63):

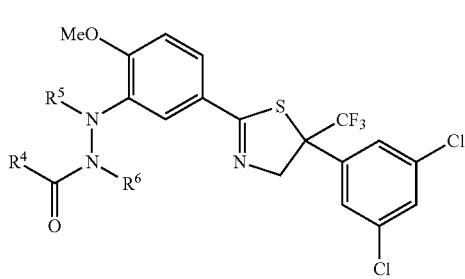

(1-63)

wherein R⁴, R⁵ and R⁶ represent any one of combinations shown below.

A compound represented by the formula (1-64):

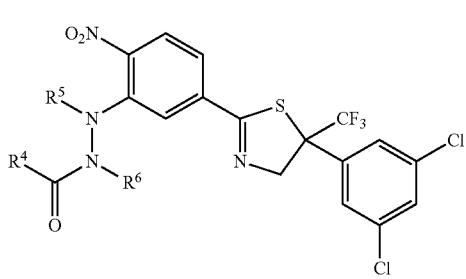

(1-64)

wherein R⁴, R⁵ and R⁶ represent any one of combinations shown below.

A compound represented by the formula (1-65):

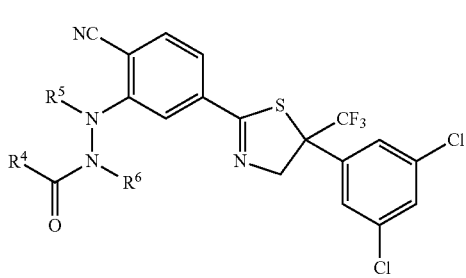

(1-65)

wherein R⁴, R⁵ and R⁶ represent any one of combinations shown below.

A compound represented by the formula (1-66):

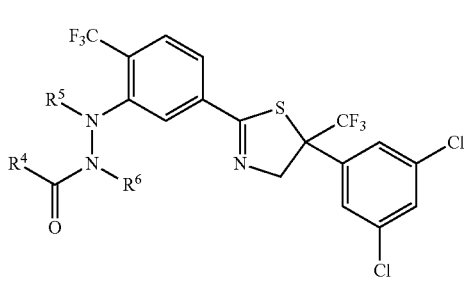

(1-66)

wherein R⁴, R⁵ and R⁶ represent any one of combinations shown below.

A compound represented by the formula (1-67):

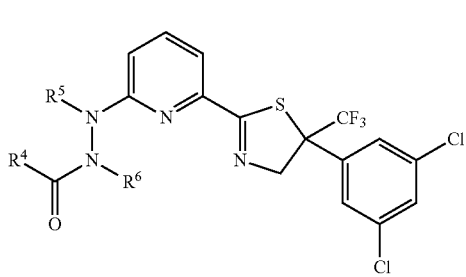

(1-67)

wherein R⁴, R⁵ and R⁶ represent any one of combinations shown below.

A compound represented by the formula (1-68):

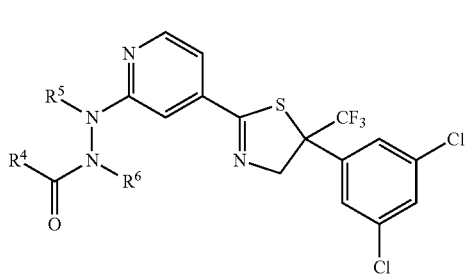
(1-68)

wherein R⁴, R⁵ and R⁶ represent any one of combinations shown below.

A compound represented by the formula (1-69):

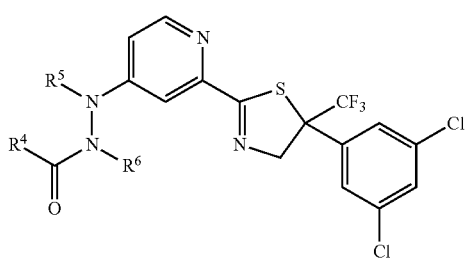
(1-69)

wherein R⁴, R⁵ and R⁶ represent any one of combinations shown below.

A compound represented by the formula (1-70):

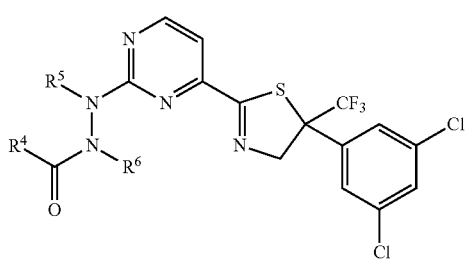
(1-70)

wherein R⁴, R⁵ and R⁶ represent any one of combinations shown below.

A compound represented by the formula (1-71):

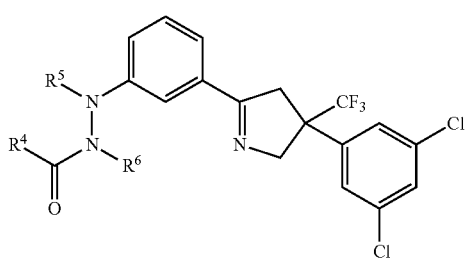
(1-71)

wherein R⁴, R⁵ and R⁶ represent any one of combinations shown below.

A compound represented by the formula (1-72):

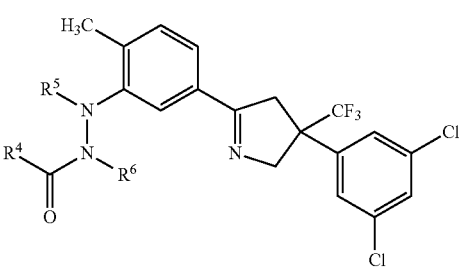
(1-72)

wherein R⁴, R⁵ and R⁶ represent any one of combinations shown below.

A compound represented by the formula (1-73):

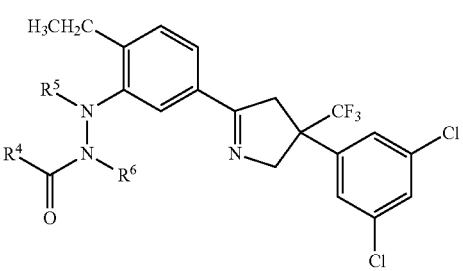
(1-73)

wherein R⁴, R⁵ and R⁶ represent any one of combinations shown below.

A compound represented by the formula (1-74):

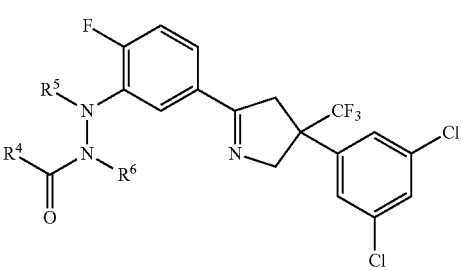
(1-74)

wherein R⁴, R⁵ and R⁶ represent any one of combinations shown below.

A compound represented by the formula (1-75):

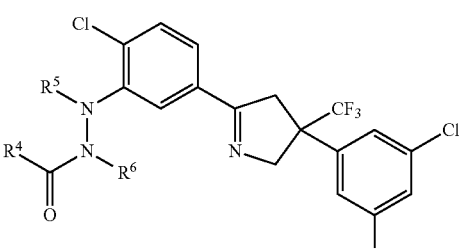
(1-75)

wherein R⁴, R⁵ and R⁶ represent any one of combinations shown below.

A compound represented by the formula (1-76):

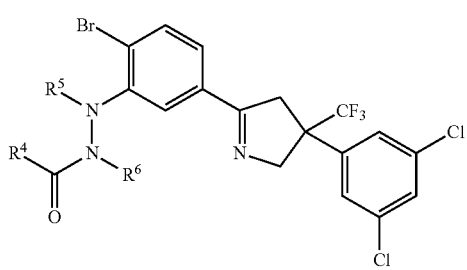
(1-76)

wherein R⁴, R⁵ and R⁶ represent any one of combinations shown below.

A compound represented by the formula (1-77):

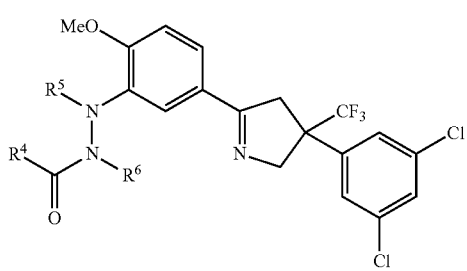
(1-77)

wherein R⁴, R⁵ and R⁶ represent any one of combinations shown below.

A compound represented by the formula (1-78):

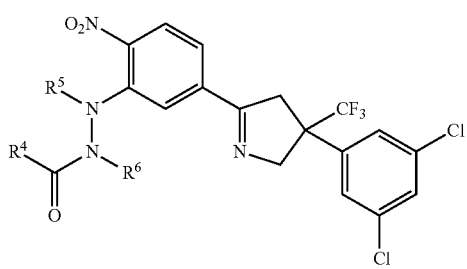
(1-78)

wherein R⁴, R⁵ and R⁶ represent any one of combinations shown below.

A compound represented by the formula (1-79):

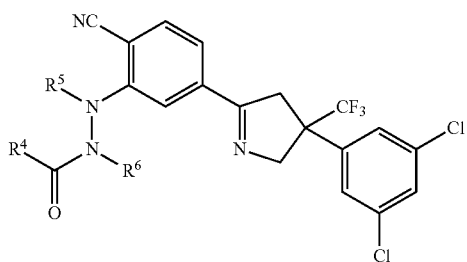
(1-79)

wherein R⁴, R⁵ and R⁶ represent any one of combinations shown below.

A compound represented by the formula (1-80):

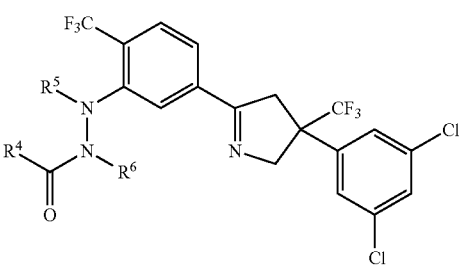
(1-80)

wherein R⁴, R⁵ and R⁶ represent any one of combinations shown below.

A compound represented by the formula (1-81):

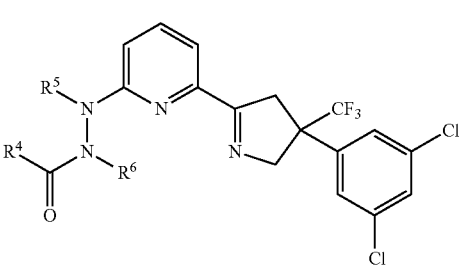
(1-81)

wherein R⁴, R⁵ and R⁶ represent any one of combinations shown below.

A compound represented by the formula (1-82):

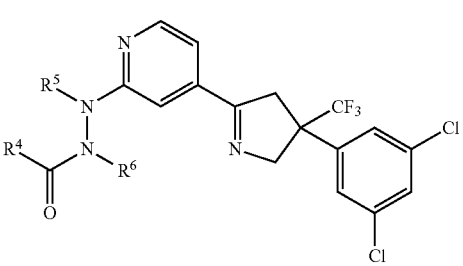
(1-82)

wherein R⁴, R⁵ and R⁶ represent any one of combinations shown below.

A compound represented by the formula (1-83):

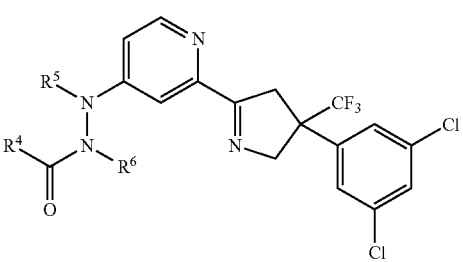
(1-83)

wherein R⁴, R⁵ and R⁶ represent any one of combinations shown below.

A compound represented by the formula (1-84):

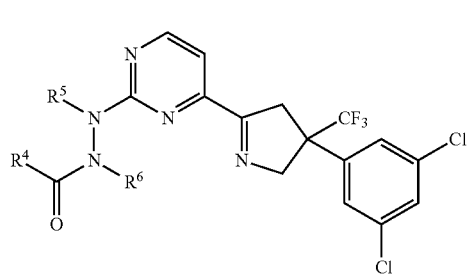
(1-84)

wherein R⁴, R⁵ and R⁶ represent any one of combinations shown below.

A compound represented by the formula (1-85):

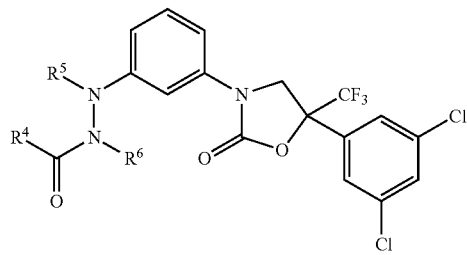
(1-85)

wherein R⁴, R⁵ and R⁶ represent any one of combinations shown below.

A compound represented by the formula (1-86):

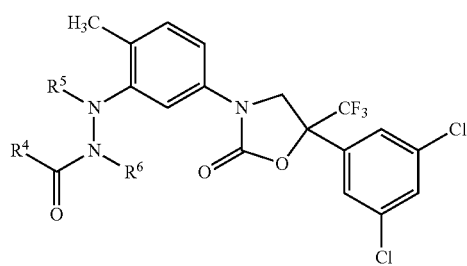
(1-86)

wherein R⁴, R⁵ and R⁶ represent any one of combinations shown below.

A compound represented by the formula (1-87):

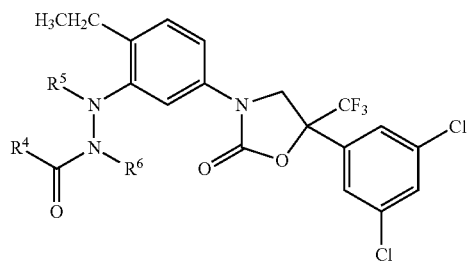
(1-87)

wherein R⁴, R⁵ and R⁶ represent any one of combinations shown below.

A compound represented by the formula (1-88):

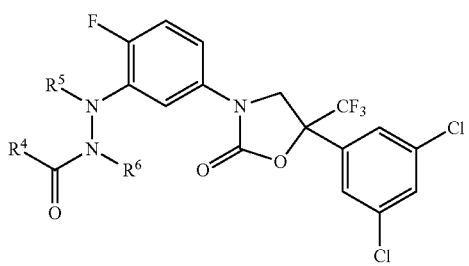
(1-88)

wherein R⁴, R⁵ and R⁶ represent any one of combinations shown below.

A compound represented by the formula (1-89):

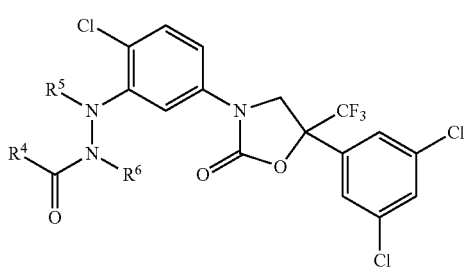
(1-89)

wherein R⁴, R⁵ and R⁶ represent any one of combinations shown below.

A compound represented by the formula (1-90):

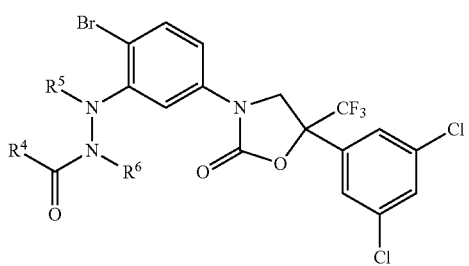
(1-90)

wherein R⁴, R⁵ and R⁶ represent any one of combinations shown below.

A compound represented by the formula (1-91):

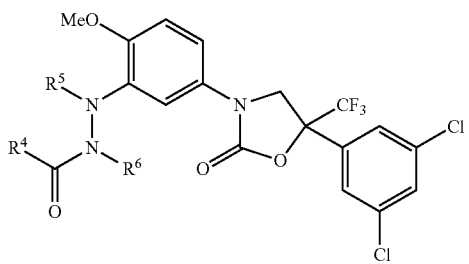
(1-91)

wherein R⁴, R⁵ and R⁶ represent any one of combinations shown below.

A compound represented by the formula (1-92):

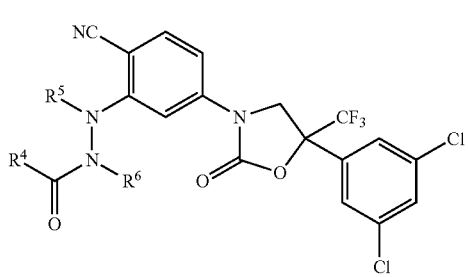
(1-92)

wherein $R^4$, $R^5$ and $R^6$ represent any one of combinations shown below.

A compound represented by the formula (1-93):

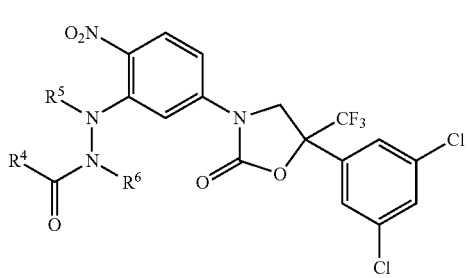
(1-93)

wherein $R^4$, $R^5$ and $R^6$ represent any one of combinations shown below.

A compound represented by the formula (1-94):

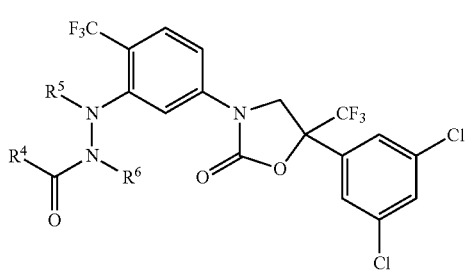
(1-94)

wherein $R^4$, $R^5$ and $R^6$ represent any one of combinations shown below.

A compound represented by the formula (1-95):

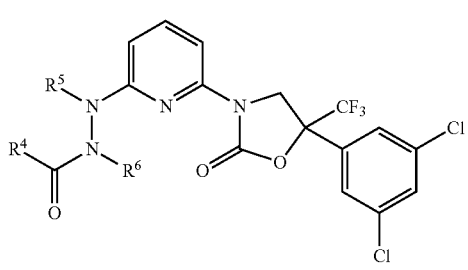
(1-95)

wherein $R^4$, $R^5$ and $R^6$ represent any one of combinations shown below.

A compound represented by the formula (1-96):

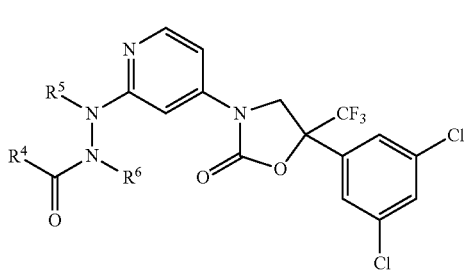
(1-96)

wherein $R^4$, $R^5$ and $R^6$ represent any one of combinations shown below.

A compound represented by the formula (1-97):

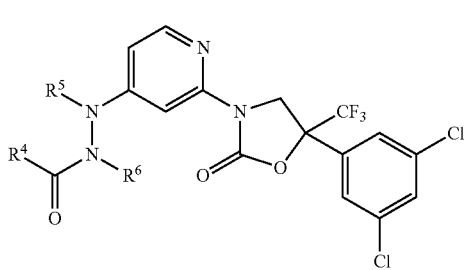
(1-97)

wherein $R^4$, $R^5$ and $R^6$ represent any one of combinations shown below.

A compound represented by the formula (1-98):

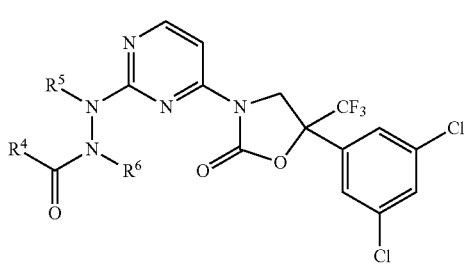
(1-98)

wherein $R^4$, $R^5$ and $R^6$ represent any one of combinations shown below.

A compound represented by the formula (1-99):

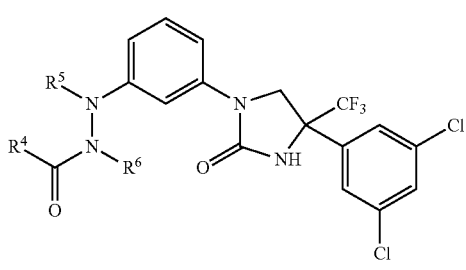
(1-99)

wherein $R^4$, $R^5$ and $R^6$ represent any one of combinations shown below.

A compound represented by the formula (1-100):

(1-100)

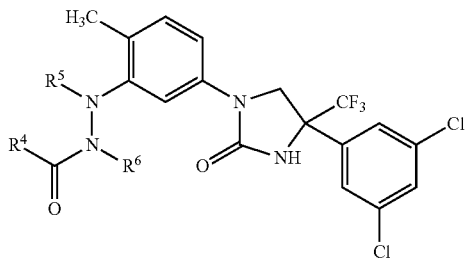

wherein $R^4$, $R^5$ and $R^6$ represent any one of combinations shown below.

A compound represented by the formula (1-101):

(1-101)

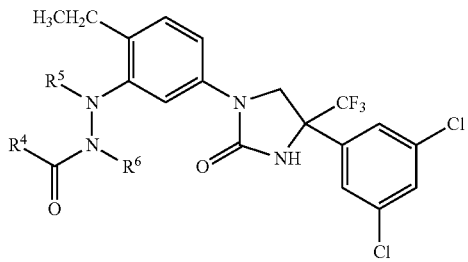

wherein $R^4$, $R^5$ and $R^6$ represent any one of combinations shown below.

A compound represented by the formula (1-102):

(1-102)

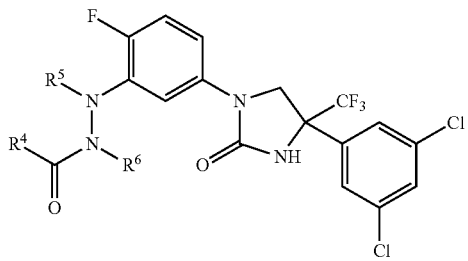

wherein $R^4$, $R^5$ and $R^6$ represent any one of combinations shown below.

A compound represented by the formula (1-103):

(1-103)

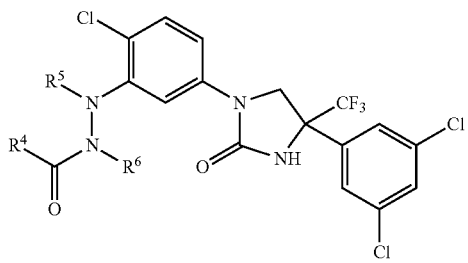

wherein $R^4$, $R^5$ and $R^6$ represent any one of combinations shown below.

A compound represented by the formula (1-104):

(1-104)

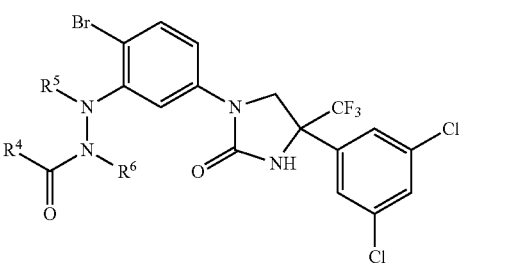

wherein $R^4$, $R^5$ and $R^6$ represent any one of combinations shown below.

A compound represented by the formula (1-105):

(1-105)

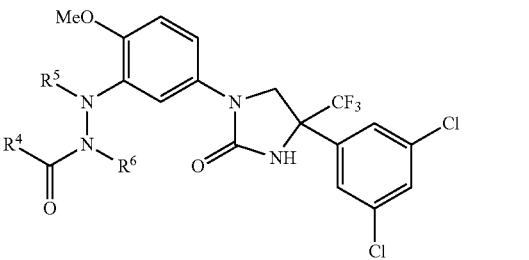

wherein $R^4$, $R^5$ and $R^6$ represent any one of combinations shown below.

A compound represented by the formula (1-106):

(1-106)

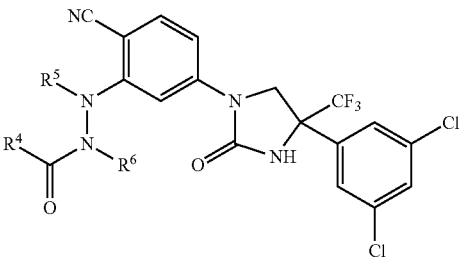

wherein $R^4$, $R^5$ and $R^6$ represent any one of combinations shown below.

A compound represented by the formula (1-107):

(1-107)

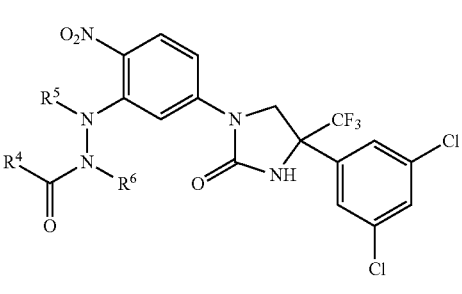

wherein $R^4$, $R^5$ and $R^6$ represent any one of combinations shown below.

A compound represented by the formula (1-108):

(1-108)

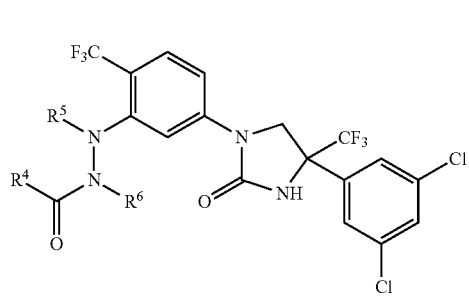

wherein R⁴, R⁵ and R⁶ represent any one of combinations shown below.

A compound represented by the formula (1-109):

(1-109)

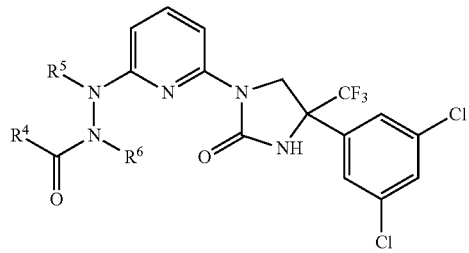

wherein R⁴, R⁵ and R⁶ represent any one of combinations shown below.

A compound represented by the formula (1-110):

(1-110)

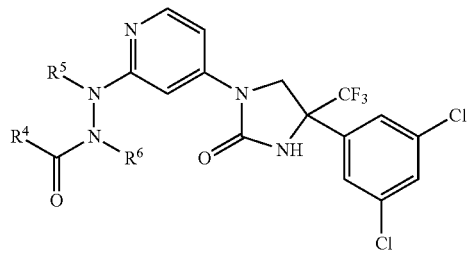

wherein R⁴, R⁵ and R⁶ represent any one of combinations shown below.

A compound represented by the formula (1-111):

(1-111)

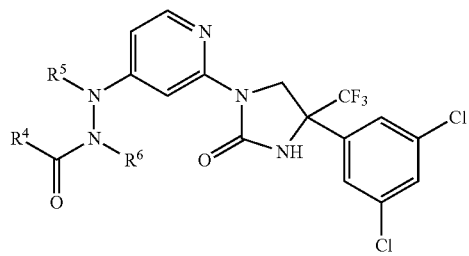

wherein R⁴, R⁵ and R⁶ represent any one of combinations shown below.

A compound represented by the formula (1-112):

(1-112)

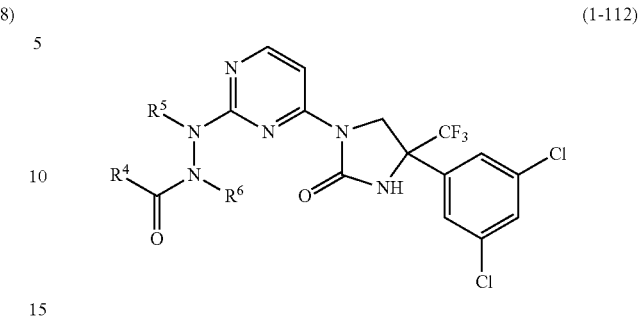

wherein R⁴, R⁵ and R⁶ represent any one of combinations shown below.

A compound represented by the formula (1-113):

(1-113)

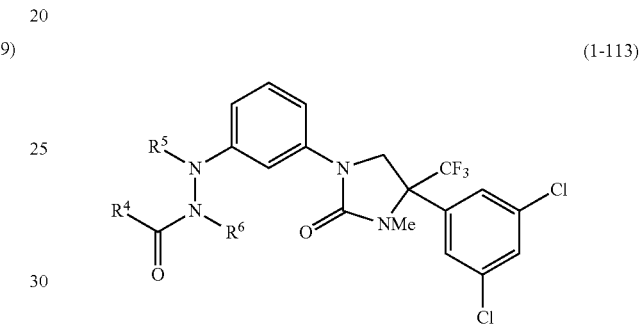

wherein R⁴, R⁵ and R⁶ represent any one of combinations shown below.

A compound represented by the formula (1-114):

(1-114)

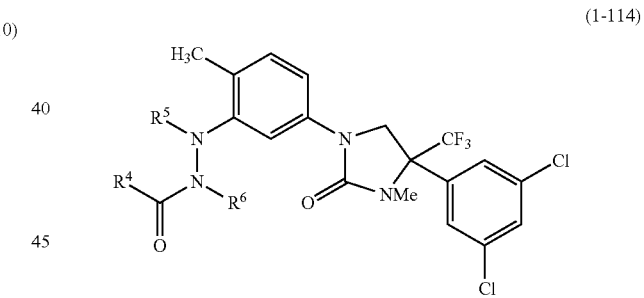

wherein R⁴, R⁵ and R⁶ represent any one of combinations shown below.

A compound represented by the formula (1-115):

(1-115)

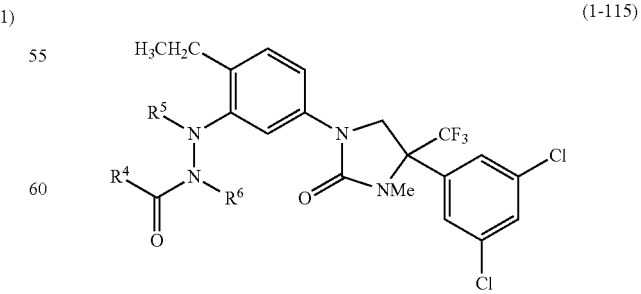

wherein R⁴, R⁵ and R⁶ represent any one of combinations shown below.

A compound represented by the formula (1-116):

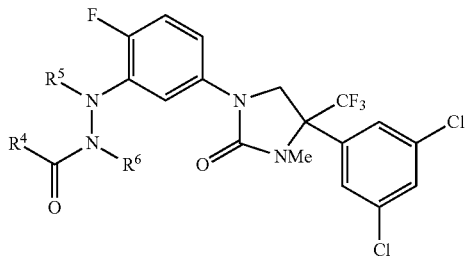

(1-116)

wherein R⁴, R⁵ and R⁶ represent any one of combinations shown below.

A compound represented by the formula (1-117):

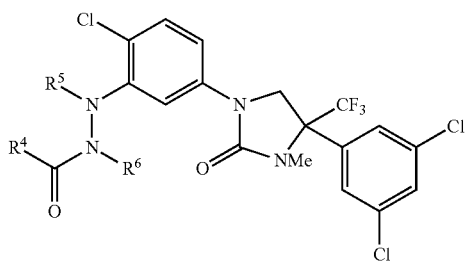

(1-117)

wherein R⁴, R⁵ and R⁶ represent any one of combinations shown below.

A compound represented by the formula (1-118):

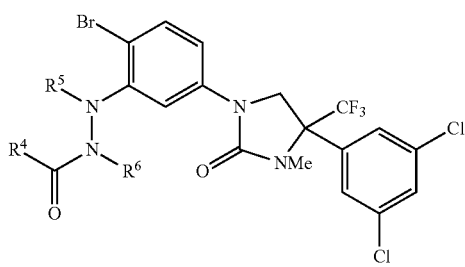

(1-118)

wherein R⁴, R⁵ and R⁶ represent any one of combinations shown below.

A compound represented by the formula (1-119):

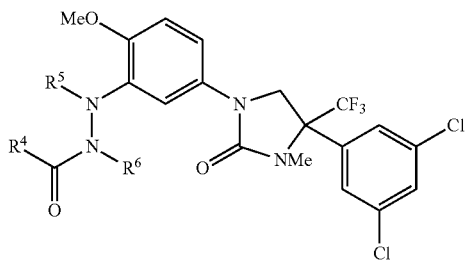

(1-119)

wherein R⁴, R⁵ and R⁶ represent any one of combinations shown below.

A compound represented by the formula (1-120):

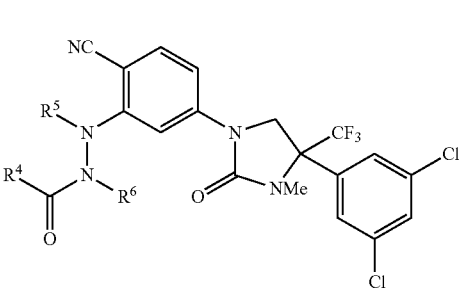

(1-120)

wherein R⁴, R⁵ and R⁶ represent any one of combinations shown below.

A compound represented by the formula (1-121):

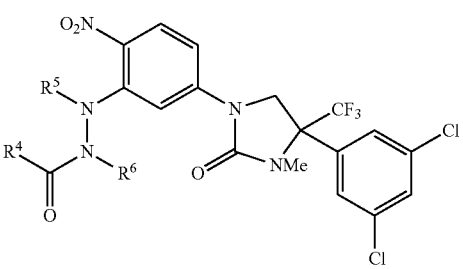

(1-121)

wherein R⁴, R⁵ and R⁶ represent any one of combinations shown below.

A compound represented by the formula (1-122):

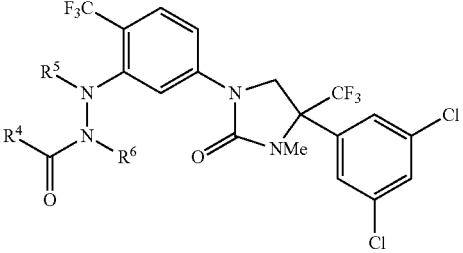

(1-122)

wherein R⁴, R⁵ and R⁶ represent any one of combinations shown below.

A compound represented by the formula (1-123):

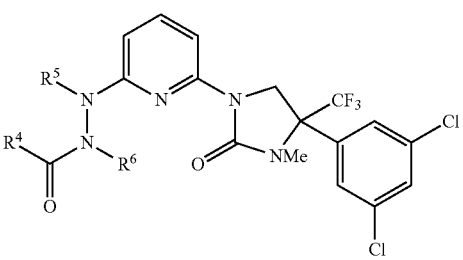

(1-123)

wherein R⁴, R⁵ and R⁶ represent any one of combinations shown below.

A compound represented by the formula (1-124):

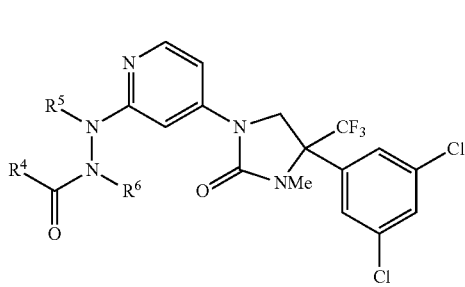

(1-124)

wherein $R^4$, $R^5$ and $R^6$ represent any one of combinations shown below.

A compound represented by the formula (1-125):

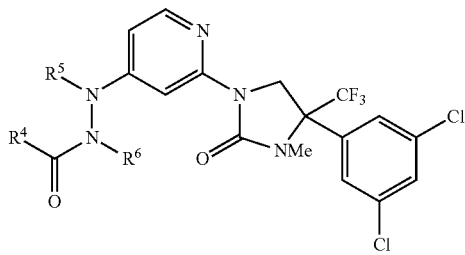

(1-125)

wherein $R^4$, $R^5$ and $R^6$ represent any one of combinations shown below.

A compound represented by the formula (1-126):

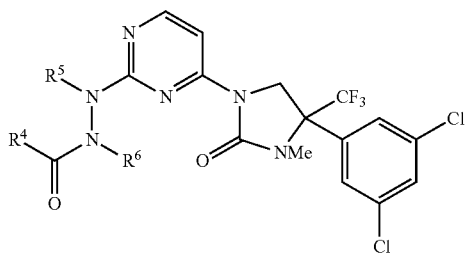

(1-126)

wherein $R^4$, $R^5$ and $R^6$ represent any one of combinations shown below.

A compound represented by the formula (1-127):

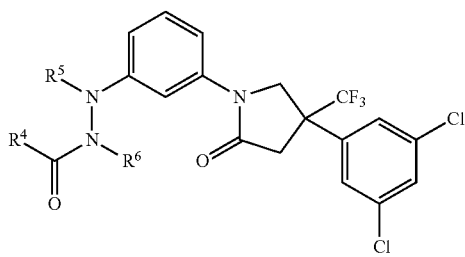

(1-127)

wherein $R^4$, $R^5$ and $R^6$ represent any one of combinations shown below.

A compound represented by the formula (1-128):

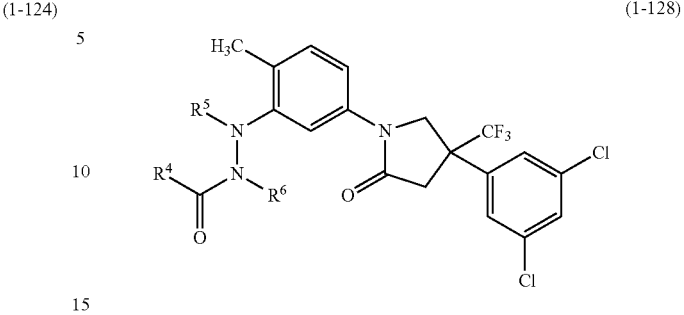

(1-128)

wherein $R^4$, $R^5$ and $R^6$ represent any one of combinations shown below.

A compound represented by the formula (1-129):

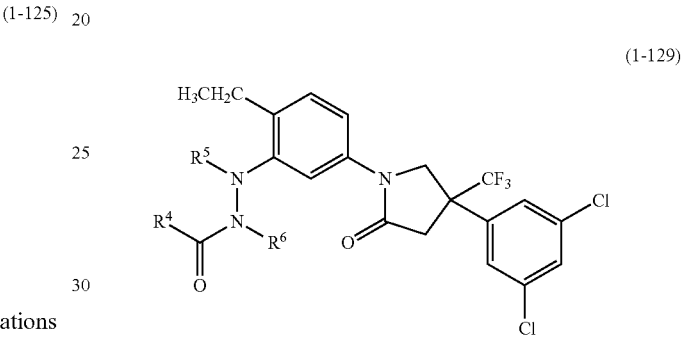

(1-129)

wherein $R^4$, $R^5$ and $R^6$ represent any one of combinations shown below.

A compound represented by the formula (1-130):

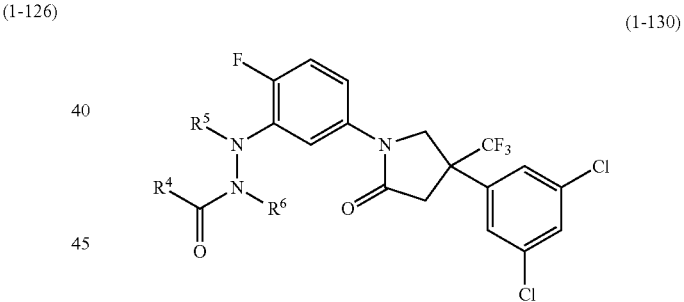

(1-130)

wherein $R^4$, $R^5$ and $R^6$ represent any one of combinations shown below.

A compound represented by the formula (1-131):

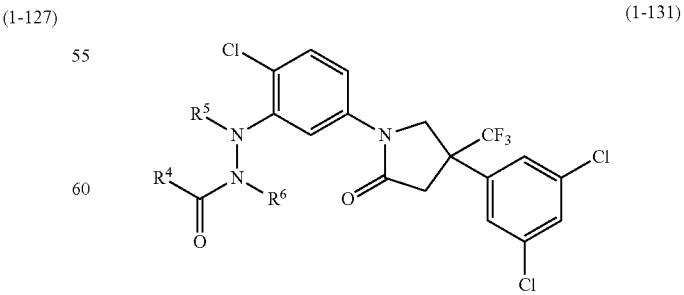

(1-131)

wherein $R^4$, $R^5$ and $R^6$ represent any one of combinations shown below.

A compound represented by the formula (1-132):

(1-132)

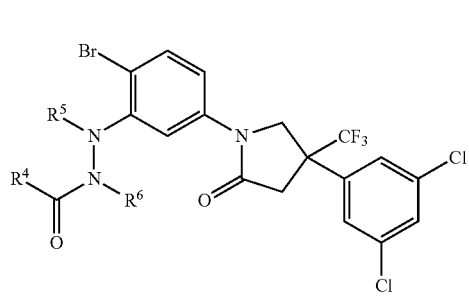

wherein R⁴, R⁵ and R⁶ represent any one of combinations shown below.

A compound represented by the formula (1-133):

(1-133)

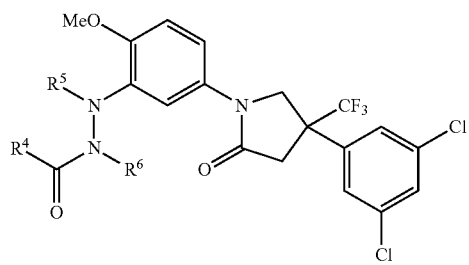

wherein R⁴, R⁵ and R⁶ represent any one of combinations shown below.

A compound represented by the formula (1-134):

(1-134)

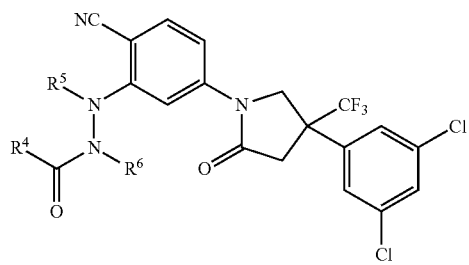

wherein R⁴, R⁵ and R⁶ represent any one of combinations shown below.

A compound represented by the formula (1-135):

(1-135)

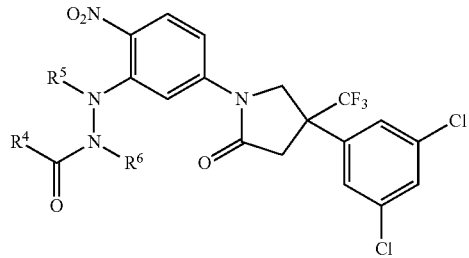

wherein R⁴, R⁵ and R⁶ represent any one of combinations shown below.

A compound represented by the formula (1-136):

(1-136)

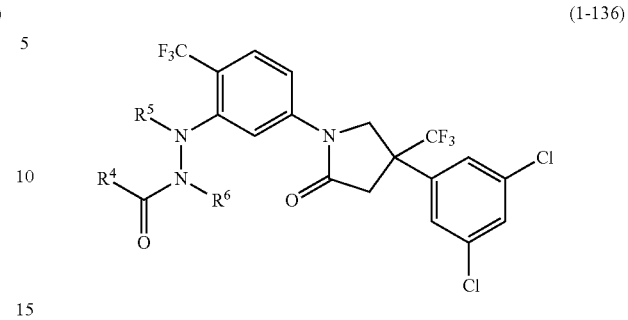

wherein R⁴, R⁵ and R⁶ represent any one of combinations shown below.

A compound represented by the formula (1-137):

(1-137)

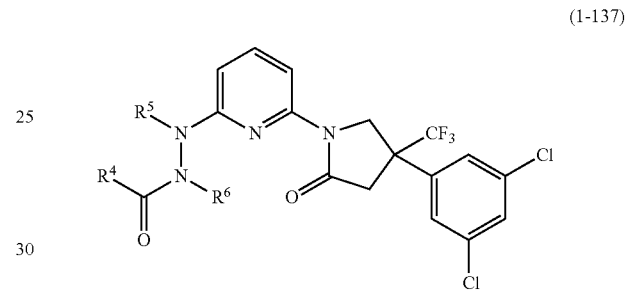

wherein R⁴, R⁵ and R⁶ represent any one of combinations shown below.

A compound represented by the formula (1-138):

(1-138)

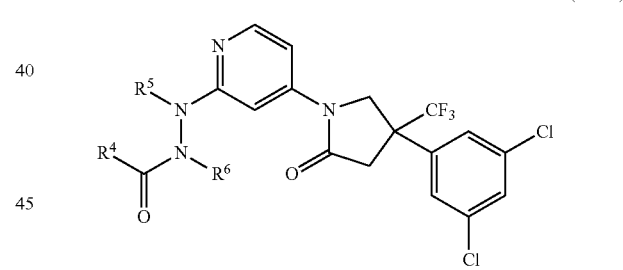

wherein R⁴, R⁵ and R⁶ represent any one of combinations shown below.

A compound represented by the formula (1-139):

(1-139)

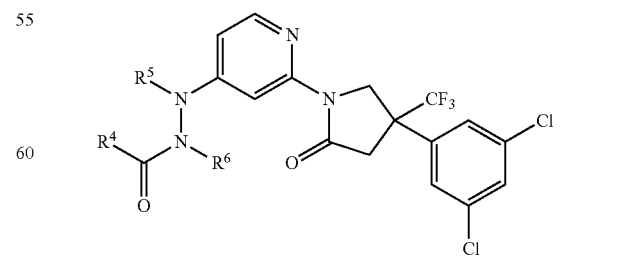

wherein R⁴, R⁵ and R⁶ represent any one of combinations shown below.

A compound represented by the formula (1-140):

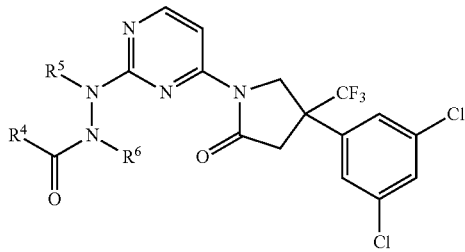

(1-140)

wherein R⁴, R⁵ and R⁶ represent any one of combinations shown below.

Combinations of A, R¹, R², R¹ᵃ, R²ᵃ, and n in the formula (1-1) to the formula (1-140) are shown below. In brackets, a branch number, a group represented by R⁴, a group represented by R⁵ and a group represented by R⁶ are shown in this order. [branch number, R⁴, R⁵, R⁶]=[1, H, H, H], [2, CH₃, H, H], [3, CH₂CF₃, H, H], [4, CH=CH₂, H, H], [5, CH=CHPh, H, H], [6, CH₂C≡CH, H, H], [7, CH₂CN, H, H], [8, CH₂NO₂, H, H], [9, CH₂N(CH₃)₂, H, H], [10, CH₂OCH₃, H, H], [11, CH₂OPh, H, H], [12, CH₂C(=O)OCH₃, H, H], [13, CH₂C(=O)CH₃, H, H], [14, CH₂Ph, H, H], [15, A1, H, H], [16, A2, H, H], [17, A3, H, H], [18, A4, H, H], [19, A5, H, H], [20, A6, H, H], [21, Ph, H, H], [22, A7, H, H], [23, A8, H, H], [24, A9, H, H], [25, A10, H, H], [26, OCH₃, H, H], [27, OPh, H, H], [28, NHCH₃, H, H], [29, N(CH₃)₂, H, H], [30, NHPh, H, H], [31, A11, H, H], [32, H, H, CH₃], [33, CH₃, H, CH₃], [34, CH₂CF₃, H, CH₃], [35, CH=CH₂, H, CH₃], [36, CH=CHPh, H, CH₃], [37, CH₂C≡CH, H, CH₃], [38, CH₂CN, H, CH₃], [39, CH₂NO₂, H, CH₃], [40, CH₂N(CH₃)₂, H, CH₃], [41, CH₂OCH₃, H, CH₃], [42, CH₂OPh, H, CH₃], [43, CH₂C(=O)OCH₃, H, CH₃], [44, CH₂C(=O)CH₃, H, CH₃], [45, CH₂Ph, H, CH₃], [46, A1, H, CH₃], [47, A2, H, CH₃], [48, A3, H, CH₃], [49, A4, H, CH₃], [50, A5, H, CH₃], [51, A6, H, CH₃], [52, Ph, H, CH₃], [53, A7, H, CH₃], [54, A8, H, CH₃], [55, A9, H, CH₃], [56, A10, H, CH₃], [57, OCH₃, H, CH₃], [58, OPh, H, CH₃], [59, NHCH₃, H, CH₃], [60, N(CH₃)₂, H, CH₃], [61, NHPh, H, CH₃], [62, A11, H, CH₃], [63, H, H, C(=O)CH₃], [64, CH₃, H, C(=O)CH₃], [65, CH₂CF₃, H, C(=O)CH₃], [66, CH=CH₂, H, C(=O)CH₃], [67, CH=CHPh, H, C(=O)CH₃], [68, CH₂C≡CH, H, C(=O)CH₃], [69, CH₂CN, H, C(=O)CH₃], [70, CH₂NO₂, H, C(=O)CH₃], [71, CH₂N(CH₃)₂, H, C(=O)CH₃], [72, CH₂OCH₃, H, C(=O)CH₃], [73, CH₂OPh, H, C(=O)CH₃], [74, CH₂C(=O)OCH₃, H, C(=O)CH₃], [75, CH₂C(=O)CH₃, H, C(=O)CH₃], [76, CH₂Ph, H, C(=O)CH₃], [77, A1, H, C(=O)CH₃], [78, A2, H, C(=O)CH₃], [79, A3, H, C(=O)CH₃], [80, A4, H, C(=O)CH₃], [81, A5, H, C(=O)CH₃], [82, A6, H, C(=O)CH₃], [83, Ph, H, C(=O)CH₃], [84, A7, H, C(=O)CH₃], [85, A8, H, C(=O)CH₃], [86, A9, H, C(=O)CH₃], [87, A10, H, C(=O)CH₃], [88, OCH₃, H, C(=O)CH₃], [89, OPh, H, C(=O)CH₃], [90, NHCH₃, H, C(=O)CH₃], [91, N(CH₃)₂, H, C(=O)CH₃], [92, NHPh, H, C(=O)CH₃], [93, A11, H, C(=O)CH₃], [94, H, CH₃, H], [95, CH₃, CH₃, H], [96, CH₂CF₃, CH₃, H], [97, CH=CH₂, CH₃, H], [98, CH=CHPh, CH₃, H], [99, CH₂C≡CH, CH₃, H], [100, CH₂CN, CH₃, H], [101, CH₂NO₂, CH₃, H], [102, CH₂N(CH₃)₂, CH₃, H], [103, CH₂OCH₃, CH₃, H], [104, CH₂OPh, CH₃, H], [105, CH₂C(=O)OCH₃, CH₃, H], [106, CH₂C(=O)CH₃, CH₃, H], [107, CH₂Ph, CH₃, H], [108, A1, CH₃, H], [109, A2, CH₃, H], [110, A3, CH₃, H], [111, A4, CH₃, H], [112, A5, CH₃, H], [113, A6, CH₃, H], [114, Ph, CH₃, H], [115, A7, CH₃, H], [116, A8, CH₃, H], [117, A9, CH₃, H], [118, A10, CH₃, H], [119, OCH₃, CH₃, H], [120, OPh, CH₃, H], [121, NHCH₃, CH₃, H], [122, N(CH₃)₂, CH₃, H], [123, NHPh, CH₃, H], [124, A11, CH₃, H][125, H, CH₃, CH₃], [126, CH₃, CH₃, CH₃], [127, CH₂CF₃, CH₃, CH₃][128, CH=CH₂, CH₃, CH₃], [129, CH=CHPh, CH₃, CH₃], [130, CH₂C≡CH, CH₃, CH₃], [131, CH₂CN, CH₃, CH₃], [132, CH₂NO₂, CH₃, CH₃], [133, CH₂N(CH₃)₂, CH₃, CH₃], [134, CH₂OCH₃, CH₃, CH₃], [135, CH₂OPh, CH₃, CH₃], [136, CH₂C(=O)OCH₃, CH₃, CH₃], [137, CH₂C(=O)CH₃, CH₃, CH₃], [138, CH₂Ph, CH₃, CH₃], [139, A1, CH₃, CH₃], [140, A2, CH₃, CH₃][141, A3, CH₃, CH₃], [142, A4, CH₃, CH₃], [143, A5, CH₃, CH₃], [144, A6, CH₃, CH₃], [145, Ph, CH₃, CH₃], [146, A7, CH₃, CH₃], [147, A8, CH₃, CH₃], [148, A9, CH₃, CH₃], [149, A10, CH₃, CH₃], [150, OCH₃, CH₃, CH₃], [151, OPh, CH₃, CH₃], [152, NHCH₃, CH₃, CH₃], [153, N(CH₃)₂, CH₃, CH₃], [154, NHPh, CH₃, CH₃], [155, A11, CH₃, CH₃], [156, H, CH₃, C(=O)CH₃], [157, CH₃, CH₃, O(=O)CH₃], [158, CH₂CF₃, CH₃, C(=O)CH₃], [159, CH=CH₂, CH₃, C(=O)CH₃], [160, CH=CHPh, CH₃, C(=O)CH₃], [161, CH₂C≡CH, CH₃, C(=O)CH₃], [162, CH₂CN, CH₃, C(=O)CH₃], [163, CH₂NO₂, CH₃, C(=O)CH₃], [164, CH₂N(CH₃)₂, CH₃, C(=O)CH₃], [165, CH₂OCH₃, CH₃, C(=O)CH₃], [166, CH₂OPh, CH₃, C(=O)CH₃], [167, CH₂C(=O)OCH₃, CH₃, C(=O)CH₃], [168, CH₂C(=O)CH₃, CH₃, C(=O)CH₃], [169, CH₂Ph, CH₃, C(=O)CH₃], [170, A1, CH₃, C(=O)CH₃], [171, A2, CH₃, C(=O)CH₃], [172, A3, CH₃, C(=O)CH₃], [173A4, CH₃, C(=O)CH₃], [174, A5, CH₃, C(=O)CH₃], [175, A6, CH₃, C(=O)CH₃], [176, Ph, CH₃, C(=O)CH₃], [177, A7, CH₃, C(=O)CH₃], [178, A8, CH₃, C(=O)CH₃], [179, A9, CH₃, C(=O)CH₃], [180, A10, CH₃, C(=O)CH₃], [181, OCH₃, CH₃, O(=O)CH₃], [182, OPh, CH₃, C(=O)CH₃], [183, NHCH₃, CH₃, C(=O)CH₃], [184, N(CH₃)₂, CH₃, C(=O)CH₃], [185, NHPh, CH₃, C(=O)CH₃], [186, A11, CH₃, C(=O) CH₃], [187, H, C(=O)CH₃, H], [188, CH₃, C(=O)CH₃, H], [189, CH₂CH₃, C(=O)CH₃, H], [190, CH=CH₂, C(=O)CH₃, H], [191, CH=CHPh, C(=O)CH₃, H], [192, CH₂C≡CH, C(=O)CH₃, H], [193, CH₂CN, C(=O)CH₃, H], [194, CH₂NO₂, C(=O)CH₃, H], [195, CH₂N(CH₃)₂, C(=O)CH₃, H], [196, CH₂OCH₃, C(=O)CH₃, H], [197, CH₂OPh, C(=O)CH₃, H], [198, CH₂C(=O)OCH₃, C(=O)CH₃, H], [199, CH₂C(=O)CH₃, C(=O)CH₃, H], [200, CH₂Ph, C(=O)CH₃, H], [201, A1, C(=O)CH₃, H], [202, A2, C(=O)CH₃, H], [203, A3, C(=O)CH₃, H], [204, A4, C(=O)CH₃, H], [205, A5, C(=O)CH₃, H], [206, A6, C(=O)CH₃, H], [207, Ph, C(=O) CH₃, H], [208, A7, C(=O)CH₃, H], [209, A8, C(=O)CH₃, H], [210, A9, C(=O)CH₃, H], [211, A10, C(=O)CH₃, H], [212, OCH₃, C(=O)CH₃, H], [213, OPh, C(=O)CH₃, H], [214, NHCH₃, C(=O)CH₃, H], [215, N(CH₃)₂, C(=O) CH₃, H], [216, NHPh, C(=O)CH₃, H], [217, A11, C(=O)CH₃, H], [218, H, C(=O)CH₃, CH₃], [219, CH₃, C(=O)CH₃, CH₃], [220, CH₂CF₃, C(=O)CH₃, CH₃], [221, CH=CH₂, C(=O)CH₃, CH₃], [222, CH=CHPh, C(=O)CH₃, CH₃], [223, CH₂C≡CH, C(=O)CH₃, CH₃], [224, CH₂CN, C(=O)CH₃, CH₃], [225, CH₂NO₂, C(=O)CH₃, CH₃], [226, CH₂N(CH₃)₂, C(=O)CH₃, CH₃], [227, CH₂OCH₃, C(=O) CH₃, CH₃], [228, CH₂OPh, C(=O)CH₃, CH₃], [229, CH₂C(=O)OCH₃, C(=O)CH₃, CH₃], [230, CH₂C(=O)CH₃, C(=O)CH₃, CH₃], [231, CH₂Ph, C(=O)CH₃, CH₃], [232, A1, C(=O)CH₃, CH₃], [233, A2, C(=O)CH₃, CH₃], [234, A3, C(=O)CH₃, CH₃], [235, A4, C(=O)CH₃, CH₃], [236, A5, C(=O)CH₃, CH₃], [237, A6, C(=O)CH₃, CH₃], [238, Ph, C(=O)CH₃, CH₃], [239, A7, C(=O)CH₃, CH₃], [240, A8, C(=O)CH₃, CH₃], [241, A9, C(=O)CH₃, CH₃], [242, A10, C(=O)CH₃, CH₃], [243, OCH₃, C(=O)CH₃, CH₃], [244, OPh, C(=O)CH₃, CH₃], [245, NHCH₃, C(=O)CH₃, CH₃], [246, N(CH₃)₂, C(=O)CH₃, CH₃], [247, NHPh, C(=O)CH₃, CH₃], [248, A11, C(=O)CH₃, CH₃], [249, H, C(=O)CH₃, C(=O)CH₃], [250, CH₃, C(=O)CH₃, C(=O)CH₃], [251, CH₂CF₃, C(=O)CH₃, C(=O)CH₃], [252, CH=CH₂, C(=O)CH₃, C(=O)CH₃], [253, CH=CHPh, C(=O)CH₃, C(=O)CH₃], [254, CH₂C≡CH, C(=O)CH₃, C(=O)CH₃], [255, CH₂CN, C(=O)CH₃, C(=O)CH₃], [256, CH₂NO₂, C(=O)CH₃, C(=O)CH₃], [257, CH₂N(CH₃)₂, C(=O)CH₃, C(=O)CH₃], [258, CH₂OCH₃, C(=O)CH₃, C(=O)CH₃], [259, CH₂OPh, C(=O)CH₃, C(=O)CH₃], [260, CH₂C(=O)OCH₃, C(=O)CH₃, C(=O)CH₃], [261, CH₂C(=O)CH₃, C(=O)CH₃, C(=O)CH₃], [262, CH₂Ph, C(=O)CH₃, C(=O)CH₃], [263, A1, C(=O)CH₃, C(=O)CH₃], [264, A2, C(=O)CH₃, C(=O)CH₃], [265, A3, C(=O)CH₃, C(=O)CH₃], [266, A4, C(=O) CH₃, C(=O)CH₃], [267, A5, C(=O)CH₃, C(=O)CH₃], [268, A6, C(=O)CH₃, C(=O)CH₃], [269, Ph, C(=O)CH₃, C(=O)CH₃], [270, A7, C(=O)CH₃, C(=O)CH₃], [271, A8, C(=O)CH₃, C(=O)CH₃], [272, A9, C(=O)CH₃, C(=O)CH₃], [273, A10, C(=O)CH₃, C(=O)CH₃], [274, OCH₃, C(=O)CH₃, C(=O)CH₃], [275, OPh, C(=O)CH₃, C(=O)CH₃], [276, NHCH₃, C(=O)CH₃, C(=O)CH₃], [277, N(CH₃)₂, C(=O)CH₃, C(=O)CH₃], [278, NHPh, C(=O)CH₃, C(=O)CH₃], [279, A11, C(=O)CH₃, C(=O)CH₃].

Wherein, A1 to A11 represent the following groups:

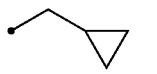

A1

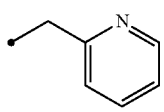

A2

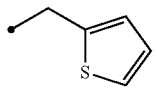

A3

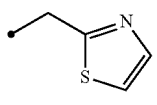

A4

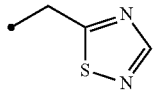

A5

A6

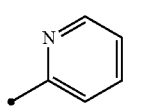

A7

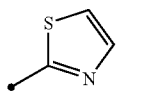

A8

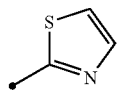

A9

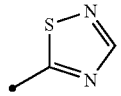

A10

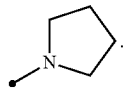

A11

Formulation Examples are be shown below. The term "part(s)" means part(s) by weight.

Formulation Example 1

Nine parts of any one of the present compounds (1) to (63) is dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 2

To 40 parts of anyone of the present compounds (1) to (63) is added 5 parts of SORPOL 5060 (registered trade name for TOHO Chemical Industry Co., LTD.) and mixed thoroughly. The mixture is mixed with 32 parts of CARPLEX #80 (registered trade name for Shionogi & Co., Ltd., synthetic hydrous silicon oxide fine powder) and 23 parts of 300 mesh diatomaceous earth by using a juice mixer to obtain a wettable powder.

Formulation Example 3

Three parts of anyone of the present compounds (1) to (63), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 4

Four point five parts of any one of the present compounds (1) to (63), 1 part of synthetic hydrous silicon oxide fine powder, 1 part of Dorires B (manufactured by Sankyo) as a flocculant, and 7 parts of clay are mixed thoroughly in a mortar, and then mixed by stirring by using a juice mixer. To the resultant mixture 86.5 parts of cut clay is added and mixed by stirring thoroughly to obtain a dust.

Formulation Example 5

Ten parts of any one of the present compounds (1) to (63), 35 parts of a mixture (weight ratio of 1:1) of a polyoxyethylene alkylether sulfate ammonium salt and white carbon, and 55 parts of water are mixed and then finely-divided by a wet grinding method to obtain a formulation.

Formulation Example 6

Zero point five part of any one of the present compounds (1) to (63) is dissolved in 10 parts of dichloromethane. This solution is mixed with 89.5 parts of Isopar M (isoparaffin: registered trade name for Exxon Chemical) to obtain an oil solution.

Formulation Example 7

Zero point one part of any one of the present compounds (1) to (63) and 49.9 parts of NEO-THIOZOL (ChuoKasei Co., Ltd.) are placed in an aerosol can. An aerosol valve is fitted to the can. The can is charged with 25 parts of dimethyl ether and 25 parts of LPG. The aerosol can is shaken. An actuator is fitted to the can to obtain an oily aerosol.

Formulation Example 8

Zero point six parts of any one of the present compounds (1) to (63), 0.01 part of BHT, 5 parts of xylene, 3.39 parts of a deodorized kerosine and 1 part of an emulsifying agent [Atmos 300 (registered trade name for Atmos Chemical Ltd.)] are mixed to obtain a solution. An aerosol container is charged with the obtained solution and 50 parts of distilled water. A valve part is attached to the container and the container is then charged with 40 parts of a propellant (LPG) through the valve under increased pressure to obtain an aqueous aerosol.

The following Test Examples demonstrate that the compound of the present invention is effective as an active ingredient of a pest-controlling composition. The compounds of the present invention are designated by their compound numbers shown above.

Test Example 1

Formulations of some compounds of the present invention were obtained according to Formulation Example 5. The formulation was diluted with water to prepare a test solution having 500 ppm of the active ingredient.

A filter paper having a diameter of 5.5 cm was spread on the bottom of a polyethylene cup having a diameter of 5.5 cm and 0.7 ml of the test solution was added dropwise onto the filter paper. As a bait, 30 mg of sucrose was uniformly placed on the filter paper. Into the polyethylene cup, 10 female imagoes of *Musca domestica* were released and the cup was sealed with a lid. After 24 hours, the number of surviving or dead *Musca domestica* was counted and a pest death rate was calculated according to the following equation.

Pest death rate(%)=(Number of dead imagoes/Number of tested imagoes)×100

As a result, the treatment with any one of the present compounds (1), (7), (8), (10), (11), (15), (17) to (20), (23), (28) to (32), (36), (38), (40) and (42) to (44) showed a pest death rate of 100%.

Test Example 2

Formulations of some compounds of the present invention were obtained according to Formulation Example 5. The formulation was diluted with water to prepare a test solution having 500 ppm of the active ingredient.

Into 100 ml of ion-exchanged water, 0.7 ml of the test solution was added (the active ingredient concentration: 3.5 ppm). Into the solution, 20 last instar larvae of *Culex pipiens pallens* were released. After 8 days, the number of surviving or dead *Culex pipiens pallens* was counted and a pest death rate was calculated according to the following equation.

Pest death rate(%)=(Number of dead larvae/Number of tested larvae)×100

As a result, the treatment with any one of the present compounds (1) to (13), (15) to (23), (25) to (32), (34), (36), (38), (40) to (45), (47) to (56) and (59) showed a pest death rate of 90% or more.

Test Example 3

Formulations of some compounds of the present invention were obtained according to Formulation Example 5. The formulation was diluted with water to prepare a test solution having 500 ppm of the active ingredient.

On cabbage (*Brassicae olercea*) at the 3rd to 4th leaf stage, 20 ml of the test solution was sprayed. After the test solution was dried, the above-ground part of the cabbage was cut off and then put in a polyethylene cup (volume: 100 mL) together with 5 second instar larvae of *Plutella xylostella*. After the polyethylene cup was stored at 25° C. for 5 days, the number of surviving or dead *Plutella xylostella* was counted and a pest death rate was calculated according to the following equation.

Pest death rate(%)=(Number of dead larvae/Number of tested larvae)×100

As a result, the treatment with any one of the present compounds (1) to (13), (15) to (23), (25), (28) to (32), (34), (36), (38), (40), (42) to (44), (47) to (51), (53) to (55), (57) and (61) showed a pest death rate of 80% or more.

Test Example 4

Formulations of some compounds of the present invention were obtained according to Formulation Example 5. The formulation was diluted with water to prepare a test solution having 500 ppm of the active ingredient.

A filter paper having a diameter of 5.5 cm was spread on the bottom of a polyethylene cup having a diameter of 5.5 cm. Insecta LF (manufactured by NOSAN CORPORATION), an artificial diet, was sliced to 6 mm in thickness, cut into half, and then placed on the filter paper. Then, 2 mL of the test solution was poured into the polyethylene cup. After the test solution was air-dried, 5 fourth instar larvae of *Spodoptela litura* were released into the polyethylene cup and the cup was sealed with a lid. After 6 days, the number of surviving or dead *Spodoptela litura* was counted and a pest death rate was calculated according to the following equation.

Pest death rate(%)=(Number of dead larvae/Number of tested larvae)×100

As a result, the treatment with any one of the present compounds (1), (5), (7) to (11), (15) to (20) to (23), (26), (28) to (32), (34), (36), (38), (40), (42) to (44), (48) to (51), (53) and (57) showed a pest death rate 80% or more.

Test Example 5

Formulations of some compounds of the present invention were obtained according to Formulation Example 5. The formulation was diluted with water to prepare a test solution having 500 ppm of the active ingredient.

A filter paper having a diameter of 5.5 cm was spread on the bottom of a polyethylene cup having a diameter of 5.5 cm. Silkmate 2S (manufactured by NOSAN CORPORATION), an artificial diet, was sliced to 2 mm in thickness, and then placed on the filter paper. Then, 1 mL of the test solution was poured into the polyethylene cup. After the test solution was air-dried, a filter paper having a diameter of 5.5 cm was placed on the artificial diet, and tehreon 30 first instar larvae of *Adoxophyes orana* were placed. The cup was sealed with a lid. After 7 days, the number of surviving or dead *Adoxophyes orana* was counted and a pest death rate was calculated according to the following equation.

Pest death rate(%)=(Number of dead larvae/Number of tested larvae)×100

As a result, the treatment with any one of the present compounds (1) to (5), (7) to (13), (15) to (23), (25) to (32), (34), (36), (38), (40), (42) to (44), (47) to (59) and (61) showed a pest death rate of 90% or more.

INDUSTRIAL APPLICABILITY

The compound of the present invention has a controlling effect on pests, and is therefore useful as an active ingredient of an pest-controlling composition.

The invention claimed is:
1. A hydrazide compound represented by the formula (1):

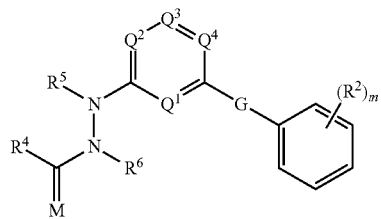

wherein,
G represents a 5-membered heterocyclic group represented by the following formula G-1, G-2 or G-3:

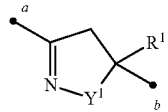

G-1

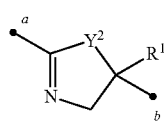

G-2

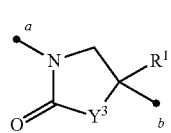

G-3 wherein a •——— and b •——— each represent a bond and the b •——— is linked to the moiety

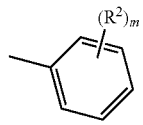

in formula (1),
$R^1$ represents a C1-C4 haloakyl group,
$Y^1$ represents an oxygen atom, a sulfur atom or an $NR^7$ group,
$Y^2$ represents an oxygen atom, a sulfur atom, an $NR^7$ group or a methylene group,
$Y^3$ represents an oxygen atom, a sulfur atom, an $NR^7$ group or a methylene group,
$R^7$ represents a C1-C6 alkyl group, a C2-C6 alkenyl group, a C2-C6 alkynyl group, a C3-C6 cycloalkyl group, a C4-C7 cycloalkylalkyl group, a C2-C6 alkylcarbonyl group, a C2-C6 alkoxycarbonyl group, a C2-C6 alkylaminocarbonyl group, a C3-C9 dialkylaminocarbonyl group, a phenyl group, a cyano group, a formyl group or a hydrogen atom,
M represents an oxygen atom or a sulfur atom,
$Q^1$, $Q^2$, $Q^3$, and $Q^4$ independently represent a nitrogen atom or a $CR^3$ group,
$R^3$ represents an optionally halogenated C1-C6 alkyl group, an optionally halogenated C1-C6 alkoxy group, a nitro group, a cyano group, a halogen atom or a hydrogen atom,
m represents an integer of 0 to 5,
$R^2$ represents an optionally halogenated C1-C6 alkyl group, an optionally halogenated C1-C6 alkoxy group, a C1-C6 alkylthio group, a C1-C6 alkylsulfinyl group, a C1-C6 alkylsulfonyl group, a nitro group, a cyano group or a halogen atom,
provided that when m is an integer of 2 to 5, $R^2$'s may be the same or different from each other,
$R^5$ and $R^6$ independently represent a C1-C12 chain hydrocarbon group optionally substituted with a group selected from Group E1, a benzoyl group optionally substituted with a group selected from Group E2, a C2-C6 alkylcarbonyl group, a C2-C6 alkoxycarbonyl group, a C3-C12 cycloalkyl group, a formyl group or a hydrogen atom,
$R^4$ represents a C1-C12 chain hydrocarbon group optionally substituted with a group selected from Group E1, a C3-C12 cyclic hydrocarbon group optionally substituted with a group selected from Group E2, a 5- to 6-membered heterocyclic group optionally substituted with a group selected from Group E2, an $OR^8$ group, an $N(R^9)R^{10}$ group or a hydrogen atom,
$R^8$ represents a C1-C12 chain hydrocarbon group optionally substituted with a group selected from Group E1, a C3-C12 cyclic hydrocarbon group optionally substituted with a group selected from Group E2, or a 5- to 6-membered heterocyclic group optionally substituted with a group selected from Group E2,
$R^9$ represents a C1-C12 chain hydrocarbon group optionally substituted with a group selected from Group E1, or a C3-C12 cyclic hydrocarbon group optionally substituted with a group selected from Group E2,
$R^{10}$ represents a C1-C12 chain hydrocarbon group optionally substituted with a group selected from Group E1, or a hydrogen atom, or
$R^9$ and $R^{10}$ are combined at their ends to represent a C2-C9 alkanediyl group, Group E1 consists of a C3-C12 cyclic hydrocarbon group optionally substituted with a group selected from Group E2, a 5- to 6-membered heterocyclic group optionally substituted with a group selected from Group E2, a phenoxy group optionally substituted with a group selected from Group E2, a phenylamino group optionally substituted with a group selected from Group E2, a C2-C6 alkylcarbonyl group, a C2-C6 alkoxycarbonyl group, a C1-C6 alkoxy group, a C1-C6 alkylamino group, a C2-C12 dialkylamino group, a nitro group, a cyano group, a formyl group and a halogen atom, and Group E2 consists of an optionally halogenated C1-C6 alkyl group, an optionally halogenated C1-C6 alkoxy group, a C2-C6 alkylcarbonyl group, a C2-C6 alkoxycarbonyl group, a C1-C6 alkylamino group, a C2-C12 dialkylamino group, a nitro group, a cyano group, a formyl group and a halogen atom.

2. A pest-controlling composition comprising the hydrazide compound according to claim 1 as an active ingredient.

3. A method for controlling a pest which comprises applying an effective amount of the hydrazide compound according to claim 1 to the pest or a habitat of the pest.

4. A hydrazine compound represented by the formula (2):

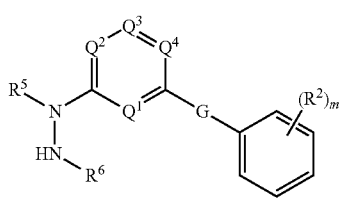

wherein,

G represents a 5-membered heterocyclic group represented by the following formula G-1, G-2 or G-3:

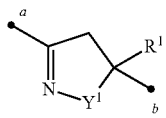

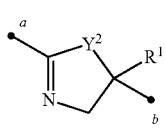

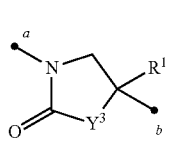

wherein a •—— and b •—— each represent a bond and the b •—— is linked to the moiety

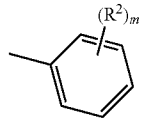

in formula (1), $R^1$ represents a C1-C4 haloakyl group, $Y^1$ represents an oxygen atom, a sulfur atom or an $NR^7$ group, $Y^2$ represents an oxygen atom, a sulfur atom, an $NR^7$ group or a methylene group, $Y^3$ represents an oxygen atom, a sulfur atom, an $NR^7$ group or a methylene group, $R^7$ represents a C1-C6 alkyl group, a C2-C6 alkenyl group, a C2-C6 alkynyl group, a C3-C6 cycloalkyl group, a C4-C7 cycloalkylalkyl group, a C2-C6 alkylcarbonyl group, a C2-C6 alkoxycarbonyl group, a C2-C6 alkylaminocarbonyl group, a C3-C9 dialkylaminocarbonyl group, a phenyl group, a cyano group, a formyl group or a hydrogen atom, $Q^1$, $Q^2$, $Q^3$ and $Q^4$ independently represent a nitrogen atom or a $CR^3$ group, $R^3$ represents an optionally halogenated C1-C6 alkyl group, an optionally halogenated C1-C6 alkoxy group, a nitro group, a cyano group, a halogen atom or a hydrogen atom, m represents an integer of 0 to 5, $R^2$ represents an optionally halogenated C1-C6 alkyl group, an optionally halogenated C1-C6 alkoxy group, a C1-C6 alkylthio group, a C1-C6 alkylsulfinyl group, a C1-C6 alkylsulfonyl group, a nitro group, a cyano group or a halogen atom, provided that when m is an integer of 2 to 5, $R^2$'s may be the same or different from each other, $R^5$ and $R^6$ independently represent a C1-C12 chain hydrocarbon group optionally substituted with a group selected from Group E1, a benzoyl group optionally substituted with a group selected from Group E2, a C2-C6 alkylcarbonyl group, a C2-C6 alkoxycarbonyl group, a C3-C12 cycloalkyl group, a formyl group or a hydrogen atom, Group E1 consists of a C3-C12 cyclic hydrocarbon group optionally substituted with a group selected from Group E2, a 5- to 6-membered heterocyclic group optionally substituted with a group selected from Group E2, a phenoxy group optionally substituted with a group selected from Group E2, a phenylamino group optionally substituted with a group selected from Group E2, a C2-C6 alkylcarbonyl group, a C2-C6 alkoxycarbonyl group, a C1-C6 alkoxy group, a C1-C6 alkylamino group, a C2-C12 dialkylamino group, a nitro group, a cyano group, a formyl group and a halogen atom, and Group E2 consists of an optionally halogenated C1-C6 alkyl group, an optionally halogenated C1-C6 alkoxy group, a C2-C6 alkylcarbonyl group, a C2-C6 alkoxycarbonyl group, a C1-C6 alkylamino group, a C2-C12 dialkylamino group, a nitro group, a cyano group, a formyl group and a halogen atom.

5. The hydrazide compound according to claim 1, which is

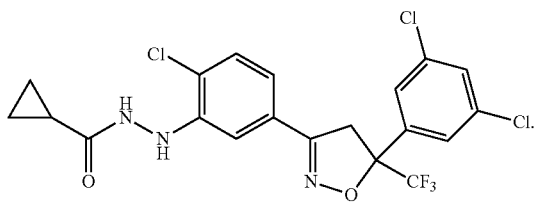 [SMILES: O=C(NNc1cc(C2=NOC(c3cc(Cl)cc(Cl)c3)(C(F)(F)F)C2)ccc1Cl)C1CC1]

6. The hydrazide compound according to claim 1, which is

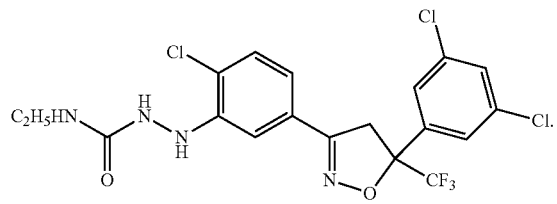

7. The hydrazide compound according to claim 1, which is

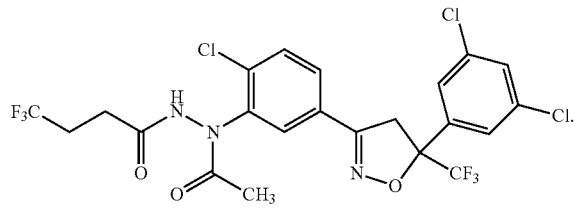 [SMILES: CC(=O)N(NC(=O)CCC(F)(F)F)c1cc(C2=NOC(c3cc(Cl)cc(Cl)c3)(C(F)(F)F)C2)ccc1Cl]

8. The hydrazide compound according to claim 1, which is

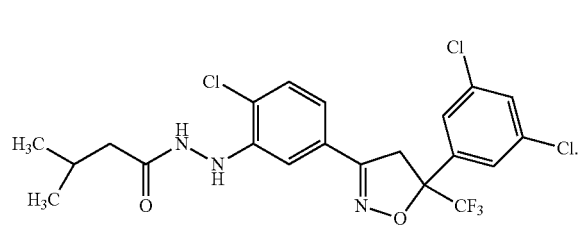 [SMILES: CC(C)CC(=O)NNc1cc(C2=NOC(c3cc(Cl)cc(Cl)c3)(C(F)(F)F)C2)ccc1Cl]

9. The hydrazide compound according to claim 1, which is

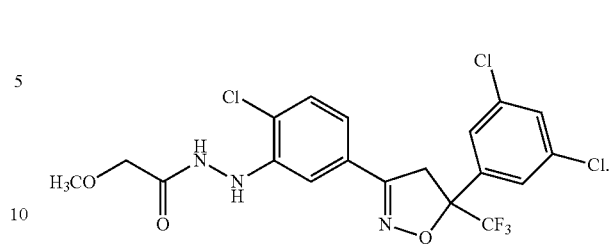

10. The hydrazide compound according to claim 1, which is

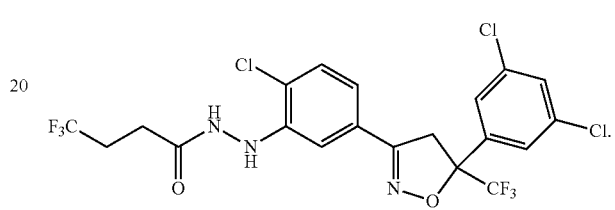

11. The hydrazide compound according to claim 1, which is

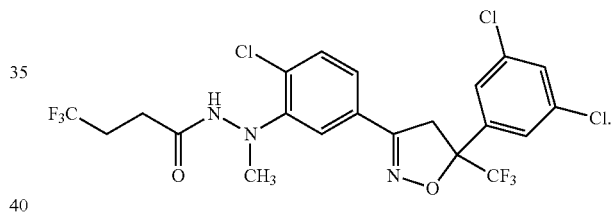

* * * * *